United States Patent [19]

Salyers et al.

[11] Patent Number: 5,674,733
[45] Date of Patent: Oct. 7, 1997

[54] METHOD AND MATERIALS FOR INTRODUCING DNA INTO *PREVOTELLA RUMINICOLA*

[75] Inventors: Abigail A. Salyers; Nadja B. Shoemaker, both of Champaign; Mikeljon P. Nikolich, Urbana, all of Ill.

[73] Assignee: Biotechnology Research and Development Corporation, Peoria, Ill.

[21] Appl. No.: 161,999

[22] Filed: Dec. 2, 1993

Related U.S. Application Data

[62] Division of Ser. No. 718,535, Jun. 5, 1991, Pat. No. 5,322,784.

[51] Int. Cl.⁶ .............................. C12N 15/63; C12N 1/21; C12N 15/74
[52] U.S. Cl. .................................... 435/252.3; 435/172.3; 435/320.1; 536/23.7; 536/24.1
[58] Field of Search .............................. 435/252.3, 172.3, 435/320.1; 530/350; 536/23.17, 24.1

[56] References Cited

U.S. PATENT DOCUMENTS 5,322,784 6/1994 Salyers et al. ..................... 435/172.3

OTHER PUBLICATIONS

Shoemaker et al. (1989), J. Bacteriol. 171(3): 1294–1302.
Smith (1987), J. Bacteriol. 169(10): 4589–4596.
Weaver et al., Genetics (Wm. C. Brown Publishers, Dubuque, Iowa, 1989), pp. 451–457.
Thomson et al. (1989), FEMS Microbiol. Letters 61: 101–104.
Abraham, et al., *Plasmid*, 19:113–120 (1988).
Anderson et al., "Development of Techniques for the Genetic Manipulation of *Bacteroides ruminicola*," Abstract, University of Illinois, Jun. 1990.
Burdett, *J. Bacteriol.*, 165:564–569 (1989).
Devereaux, et al., *Nucl. Acids Res.*, 12:387–395 (1985).
DeVries, et al., *Proc. Nat. Acad. Sci. USA*, 57:1010–1012 (1967).
Flint, et al., *Appl. Environ. Microbiol.*, 54:855–860 (1988).
Guiney, et al., *J. Bacteriol.*, 172:495–497 (1990).
Henikoff, *Gene*, 28:351 (1984).
Jacquet, et al., *The EMBO J.*, 7:2861–2867 (1988).
Jurnak, *Science*, 230:32–36 (1985).
Lacks, et al., *J. Mol. Biol.*, 192:753–765 (1986).
LeBlanc et al., *J. Bacteriol.*, 170:3618–3626 (1988).
Lederberg, et al., *J. Bacteriol.*, 119:1072–1074 (1974).
Manavathu, et al., *Antimicrob. Agents Chemother.*, 34:71–77 (1990).
Manavathu, et al., *Gene*, 62:17–26 (1988).
Martin, et al., *Nucl. Acids Res.*, 14:7047–7058 (1986).
Meyer, et al., *J. Bacteriol.*, 143:1362–1373 (1980).
Odelson, et al., *Plasmid*, 17:87–109 (1987).
Rigby, et al., *J. Mol. Biol.*, 113:237–251 (1977).
Salyers, et al., *CRC Critical Reviews in Microbiology*, 14:49–71 (1987).
Sancar, et al., *J. Bacteriol.*, 137:692–693 (1979).
Sanchez–Pescador, et al., *Nucl. Acids Res.*, 16:1216–1218 (1988).
Shah, et al., *Intl. J. Syst. Bacteriol.*, 40:205–208 (1990).
Shoemaker, et al., *Appl. Environ. Microbiol.*, 57:2114–2120 (1991).
Shoemaker, et al., *J. Bacteriol.*, 172:1694–1702 (1990).
Shoemaker, et al., *J. Bacteriol.*, 166:959–965 (1986).
Shoemaker, et al., *J. Bacteriol.*, 170:1651–1657 (1988).
Shoemaker, et al., *J. Bacteriol.*, 162:626–632 (1985).
Simon, et al., *Bio/Technology*, 1:784–791 (1983).
Smith, *J. Bacteriol.*, 164:294–301 (1985).
Sougakoff, et al., *FEMS Microbiol. Lett.*, 44:153–159 (1987).
Speer, et al., *J. Bacteriol.*, 170:1423–1429 (1988).
Stevens, et al., *J. Bacteriol.*, 172:4271–4279 (1990).
Thomson, et al., *Current Microbiology*, 24:49–54 (1992).
Valentine, et al., *J. Bacteriol.*, 170:1319–1324 (1988).
Whitehead, et al., *Appl. Environ. Microbiol.*, 55:893–896 (1989).

*Primary Examiner*—Mindy Fleisher
*Assistant Examiner*—Nancy J. Degen
*Attorney, Agent, or Firm*—Brinks Hofer Gilson & Lione

[57] ABSTRACT

A method of introducing expressible heterologous DNA into *Prevotella ruminicola* is provided. The method involves conjugal transfer of a shuttle vector comprising the heterologous DNA operatively linked to a promoter functional in *P. ruminicola*. The invention also provides shuttle vectors for use in the method and *P. ruminicola* produced by the method. The invention further provides a tetracycline resistance gene of the TetQ class, or fragments thereof that confer tetracycline resistance, and a protein of the TetQ class that provides resistance to tetracycline by protecting ribosomes from tetracycline, or active fragments thereof. Finally, the invention provides a promoter functional in *P. ruminicola* and an engineered *P. ruminicola* comprising expressible foreign DNA.

10 Claims, 13 Drawing Sheets

Fig. 6A

```
           0          *
Bat-TetQ   MNIINLGILA  HIDAGKTSVT  ENLLFASGAT  EKCGCVDNGD  TITDSMDIEK
Caj-TetO   MKIINLGILA  HVDAGKTTLT  ESLLYTSGAI  AELGSVDEGT  TRTDTMNLER
Stp-TetM   MKIINIGVLA  HVDAGKTTLT  ESLLYNSGAI  TELGSVDRGT  TKTDNTLLER
Consensus  MkIINlGiLA  HvDAGKTtlT  EsLLy.SGAi  .elGsVD.Gt  T.TD.m.lEr
           $ +         $ $+$$++    +           +           $ 50                     *
Bat-TetQ   RRGITVRAST  TSIIWNGVKC  NIIDTPGHMD  FIAEVERTFK  MLDGAVLILS
Caj-TetO   QRGITIQTAV  TSFQWEDVKV  NIIDTPGHMD  FLAEVYRSLS  VLDGAVLLVS
Stp-TetM   QRGITIQTAI  TSFQWKNTKV  NIIDTPGHMD  FLAEVYRSLS  VLDGAILLIS
Consensus  qRGITiqta.  TSfqW..vKv  NIIDTPGHMD  FlAEVyRsls  vLDGAvLl.S
           $+$$$       +           +++$+$$$ $  + ++ ++     ++$+$+$ 100                    *                       *
Bat-TetQ   AKEGIQAQTK  LLFNTLQKLQ  IPTIIFINKI  DRAGVNLERL  YLDIKANLSQ
Caj-TetO   AKDGIQAQTR  ILFHALQIMK  IPTIFFINKI  DQEGIDLPMV  YREMKAKLSS
Stp-TetM   AKDGVQAQTR  ILFHALRKIG  IPTIFFINKI  DQNGIDLSTV  YQDIKEKLSA
Consensus  AKdGiQAQTr  iLFHaLqk..  IPTIfFINKI  Dq.GidL..v  Y.diKakLs.
           $ $         +           + + $$ $$   $  +        +

```
                  150                                                    199
Bat-TetQ    DVLFMQNVVD  GSVYPVCSQT  YIKEEYKEFV  CNHDDNILER  YLADSEISPA
Caj-TetO    EIIVKQKVGQ  HPHINVTDND  DMEQ..WDAV  IMGNDELLEK  YMSGKPFKMS
Stp-TetM    EIVIKQKVEL  HPNMRVMNFT  ESEQ..WDMV  IEGNDYLLEK  YTSGKLLEAL
Consensus   ei..kQkV..  hp....V...t  ..eq..wd.V  i.gnD.lLEk  Y.sgk.....
                +                       ++         ++         +    +

200                                                    249
Bat-TetQ    DYWNTIIALV  AKAKVYPVLH  GSAMFNIGIN  ELLDAITS.F  ILPPASVSNR
Caj-TetO    ELEQEENRRF  QNGTLFPVYH  GSAKNNLGTR  QLIEVIASKF  YSSTPEGQSE
Stp-TetM    ELEQEESIRF  HNCSLFPVYH  GSAKNNIGID  NLIEVITNKF  YSSTHRGQSE
Consensus   eleqee..rf  .n..lfPVyH  GSAknNiGi.  .LievitskF  ysst..gqse
               +++         ++         +++  +         +          +

250                                                    299
Bat-TetQ    LSSYLYKIEH  DPKGHKRSFL  KIIDGSLRLR  DVVRINDSEK  FIKIKNLKTI
Caj-TetO    LCGQVFKIEY  SEKRRRFVYV  RIYSGTLHLR  DVIRISEKEK  .IKITEMYVP
Stp-TetM    LCGKVFKIEY  SEKRQRLAYI  RLYSGVLHLR  DPVRISEKEK  .IKITEMYTS
Consensus   Lcg.vfkIEy  seKr.r..y.  riysG.LhLR  DvvRIsekEK  .IKitemyt.
              $  ++$      +  ++$        + ++$         +
```

```
            300                                                      349
Bat-TetQ    NQGREINVDE  VGANDIAIVE  DMDDFRIGNY  LGAEPCLIQG  ..LSHQHPAL
Caj-TetO    TNGELYSSDT  ACSGDIVILP  N.DVLQLNSI  LGNEILLPQR  KFIENPLPMI
Stp-TetM    INGELCKIDK  AYSGEIVILQ  N.EFLKLNSV  LGDTKLLPQR  ERIENPLPLL
Consensus   .nGel...D.  a.sgdivil.  n.d.l.lns.  LG.e.llpQr  ..ienplp.l
                           +           +           +           +
```

Fig. 6D

```
                350                                                                           399
Bat-TetQ    KSSVRPDRPE  ERSKVISALN  TLWIEDPSLS  FSINSYSDEL  EISLYGLTQK
Caj-TetO    QTTIAVKKSE  QREILLGALT  EISDCDPLLK  YVVDTTTHEI  ILSFLGNVQM
Stp-TetM    QTTVEPSKPQ  QREMLLDALL  EISDSDPLLR  YVVDSATHEI  ILSFLGKVQM
Consensus   qttv.p.kpe  qRe.ll.AL.  eisd.DPlL.  yyvds.thEi  ilsflG.vQm
                 +         ++          ++                      +

400                                                                           449
Bat-TetQ    EIQTLLEER   FSVKVHFDEI  KTIYKERPVK  KVNKIIQIEV  PPNPYWATIG
Caj-TetO    EVICAILEEK  YHVEAEIKEP  TVIYMERPLR  KAEYTIHIEV  PPNPFWASVG
Stp-TetM    EVTCALLQEK  YHVEIEIKEP  TVIYMERPLK  KAEYTIHIEV  PPNPFWASIG
Consensus   EvicalleEk  yhVe.eikEp  tvIYmERPlk  KaeytihiEv  PPNPfWAsiG
                +           +          + +         +

450                                                                           499
Bat-TetQ    LTLEPLPLGT  GLQIESDISY  GYLNHSFQNA  VFEGIRMSCQ  SGLHGWEVTD
Caj-TetO    LSIEPLPIGS  GVQYESRVSL  GYLNQSFQNA  VMEGVLYGCE  QGLYGWKVTD
Stp-TetM    LSVAPLPLGS  GVQYESSVSL  GYLNQSFQNA  VMEGIRYGCE  QGLYGWNVTD
Consensus   Ls.ePLPlGs  GvQyES.vSl  GYLNqSFQNA  VmEGirygCe  qGLyGW.VTD
                +           +          +           +            ++
```

```
            500                                                                                    549
Bat-TetQ    LKVTFTQAEY  YSPVSTPADF  RQLTPYVFRL  ALQQSGVDIL  EPMLYFELQI
Caj-TetO    CKICFEYGLY  YSPVSTPADF  RLLSPIVLEQ  ALKKAGTELL  EPYLHFEIYA
Stp-TetM    CKICFKYGLY  YSPVSTPADF  RMLAPIVLEQ  VLKKAGTELL  EPYLSFKIYA
Consensus   cKicF.yqlY  YSPVSTPADF  R.L.PiVleq  aLkkaGtelL  EpyL:Feiya
             +    +       +           +           +          ++

550                                                                                    599
Bat-TetQ    PQAASSKAIT  DLQKMMSEIE  DISCNNEWCH  IKGKVPLNTS  KDYASEVSSY
Caj-TetO    PQEYLSRAYH  DAPRYCADIV  STQIKNDEVI  LKGEIPARCI  QEYRTDLTYF
Stp-TetM    PQEYLSRAYN  DAPKYCANIV  DTQLKNNEVI  LSGEIPARCI  QEYRSDLTFF
Consensus   PQeylSrAy.  Dapkyca.Iv  dtq.kN.evi  lkGeiParci  qeYrsdlt.f
             +            +           +           +          +

600                                                                                    645
Bat-TetQ    TKGLGIFMVK  PCGYQITKGG  YSDNIRMNEK  ..DKLLFMFQ  KSMSSK
Caj-TetO    TNGQGVCLTE  LKGYQPAIGK  FICQPRRPNS  RIDKVRHMFT  S
Stp-TetM    TNGRSVCLTE  LKGYHVTTGE  PVCQPRRPNS  RIDKVRYMFN  KIT
Consensus   TnG.gvclte  lkGYq.t.G.  ..cqpRrpns  riDKvr.MF.  k
             +            +           +           +
```

Fig. 7A

```
                                              2Δ1
                                             (R/R)
                                              |
tetQ   1  CTCAAATGCCAAACTAAAGAAGATATATTGGCCAAAATAAACGCTATACCGAGAGAGAAACT  60 tetQ  61  TGATTTTTCAACTTCCCTAAAACAGTGTTGTTCAAACATTTCTACTTATTGTACTTACCA   120

2Δ2
                                                        (R/I)
                                                         |
tetQ 121  GTTGAACCTACGTTTCCCCTAATAAAAATGTCTATGGTAAAAAGTTAAAAAATCCTCCTACT  180
tetO      ttgcacttttattataggggcttagttttttgtac
tetM      atgtcctttttaggagggcttagttttttgtac
```

```
                                      — TO FIG. 7A — tetQ    TTTGTTAGATATATTTTTTTGTGTAATTTTTGTAATCGTTATGGGCAGTAATAATATACA
        181                   +              +              +              + 240
tetO    ccagtttaagaatactttatcatgtaATTtTA...TATgCccgaaaAcA.TATaaGt.T
tetM    ccagtttaagaatacctttatcatgtgATTcTAaagTATcCCg....AcAaTATctGtaT 2Δ3
                                       (R/S)
                                         |
tetQ    TATTAATACGAGTTATTAATCCCTGTAGTTCTCATATGCTACGAGGAGGTATTAAAAGGTG
        241                   +              +              +              + 300
tetO    GtTTT.ggggCtatTGGagtTTATtca......CCCAgTGATAggAGTATTTATCACTGG
tetM    GcTTTgtatgCcctaTGG..TTATgcataaaatCCCAgTGATAagAGTATTTATCACTGG

— TO FIG. 7C —
```

```
                                                             2Δ6
                                 2Δ5                         (S/S)
                                 (S/S)                         | MetAsnIleIleAsn>
                          2Δ4   |  -10                         |
                          (I/S)  |                             |
         -35             |       |                             |
tetQ   CGTTTCGACAATGCATCTATTGTAGTATATTATTGCTTAATCCAAATGAATATTATAAAT    + 360
301    +          +           +          +           +           +
tetO   GtATTTTTATGCCCttTTTTGGG.TgTTGAtaGGAgGAGGAAAATCACATG
tetM   G.ATTTTTATGCCC..TTTTGGGtTTTTGAatGGAgGAGGAAAATCACATG
```

METHOD AND MATERIALS FOR INTRODUCING DNA INTO *PREVOTELLA RUMINICOLA*

This application is a division of application Ser. No. 07/718,535 filed Jun. 5, 1991, now U.S. Pat. No. 5,322,784.

FIELD OF THE INVENTION

This invention relates generally to methods and materials for the genetic manipulation of *Prevotella ruminicola*. This invention also relates to a novel class of tetracycline resistance genes.

BACKGROUND OF THE INVENTION

A. Bacteroides and Prevotella

Bacteroides is a genus of Gram negative, obligately anaerobic bacteria found in the gastrointestinal tracts of humans and animals. These bacteria function in metabolizing a wide range of carbohydrates. In humans, Bacteroides account for approximately 25% of the bacteria in the colon.

*Prevotella ruminicola* is a species of Gram negative, obligately anaerobic bacteria found in the rumen of cattle. *P. ruminicola* ferment carbohydrates such as hemicellulose, cellobiose, and starch and aid digestion and degradation of polysaccharides. *P. ruminicola* was previously classified as a member of the genus Bacteroides (*Bacteroides ruminicola*) because it has some characteristics associated with human colonic Bacteroides species. However, recent investigations showed that *P. ruminicola* shared less than 5% DNA-DNA homology with the colonic Bacteroides species. More detailed biochemical analyses also suggested that it belonged in a separate genus, Prevotella [See Shah, et al., *Intl. J. Syst. Bacteriol.*, 40:205–208 (1990)].

Some progress has been made in connection with genetic manipulation of obligately anaerobic Bacteroides from the human colon. For example, shuttle vectors have been developed for use with some colonic Bacteroides which contain DNA from cryptic Bacteroides plasmids which are able to replicate in a number of different Bacteroides species [See Odelson, et al., *Plasmid*, 17:87–109 (1987); Salyers, et al., *Crit. Rev. Microbiol.*, 14:49–71 (1987); Valentine, et al., *J. Bacteriol.*, 170:1319–1324 (1988)]. These vectors also contain sequences which allow them to replicate in *E. coli* and be mobilized out of *E. coli* by IncP plasmids. The IncP plasmids R751 and RP4 have been shown to mobilize DNA from *E. coli* to a variety of other species, including colonic Bacteroides species [See Salyers, et al., *Crit, Rev. Microbiol,*, 14:49–71 (1987); Shoemaker, et al., *J. Bacteriol.*, 166:959–965 (1986)]. One such *E. coli*-Bacteroides shuttle vector is pVAL-1 which contains cryptic Bacteroides plasmid pB8-51 [Valentine, et al., *J. Bacteriol.*, 170:1319–1324 (1988)].

Certain colonic Bacteroides strains have been found to harbor large self-transmissible elements carrying a tetracycline resistance ("Tc$^r$") gene which are referred to as "conjugal elements" or "Tc$^r$ elements." Some of these Tc$^r$ elements also carry a clindamycin-erythromycin resistance ("Em$^r$") gene and are referred to as "Tc$^r$Em$^r$ elements." These elements are not plasmids, but are integrated into the host chromosome.

The Tc$^r$ and Em$^r$ genes from a conjugal Tc$^r$Em$^r$ strain of Bacteroides, *Bacteroides thetaiotaomicron* DOT, have been cloned, along with regions of the element that include transfer genes [Shoemaker, et al., *J. Bacteriol.*, 171:1294–1302 (1989)]. The Tc$^r$Em$^r$ element from *B. thetaiotaomicron* DOT has been designated "Tc$^r$Em$^r$-DOT."

2

These conjugal elements are able to transfer themselves from one colonic Bacteroides strain to another and to mobilize co-resident plasmids, not only from Bacteroides to Bacteroides, but also from Bacteroides to *E. coli* [See Odelson, et al., *Plasmid*, 17:87–109 (1987); Salyers, et al., *Crit. Rev. Microbiol.*, 14:49–71 (1987); Thomson, et al., *FEMS Microbiol. Letters*, 61:101–104 (1989); Stevens, et al., *J. Bacteriol.*, 172:4271–4279 (1990)]. Thus, the Tc$^r$ and Tc$^r$Em$^r$ conjugal elements found in the colonic Bacteroides strains appear to be able to mediate mating pair formation between diverse genera of bacteria.

The conjugal element, Tc$^r$Em$^r$ 12256, has been found to mobilize co-resident plasmids at high frequencies [See Valentine, et al., *J. Bacteriol.*, 170:1319–1324 (1988)]. Furthermore, the Tc$^r$Em$^r$ 12256 element appears to exhibit constitutive transfer, as opposed to other Tc$^r$ and Tc$^r$Em$^r$ elements which require pre-exposure to tetracycline to obtain maximum transfer frequencies.

Plasmid DNA has been introduced into some colonic Bacteroides using transformation techniques [See Salyers, et al., *CRC Clinical Reviews in Microbiology*, 14:49–71 (1987); Odelson, et al., *Plasmid*, 17:87–109 (1987); Smith, *J. Bacteriol.*, 164:294–301 (1985)]. For instance, one colonic Bacteroides species has been transformed by electroporation [Thomson, et al., *FEMS Microbiol. Letters*, 61:101–104 (1989)]. An *E. coli* colonic Bacteroides shuttle vector, pDP1, was isolated from *Bacteroides uniformis* and electroporated into *B. uniformis* at a frequency of $10^6$ transporants per microgram of DNA. However, the same plasmid, when isolated from *E. coli* EM24, gave only $10^3$ transporants per microgram of DNA.

Standard methods, however, appear to be inadequate in several respects for the transformation of the colonic Bacteroides. For example, large plasmids are difficult to introduce into these species by transformation techniques. Best results are obtained when the plasmid DNA is less that 5 kbp in size. Also, to obtain good rates of transformation, the donor plasmid must be isolated from the same strain used as the recipient. The difficulties encountered in crossing species lines are believed to be due to the presence of restriction barriers. Also, successful transformation of many species of colonic Bacteroides has been sporadic [See Odelson, et al., *Plasmid*, 17:102 (1987)]. Clearly, much improvement is needed in transformation methods for colonic Bacteroides.

Despite progress in understanding the genetics of colonic Bacteroides, *P. ruminicola* is not well understood genetically. There have been some biochemical studies of polysaccharide utilization by *P. ruminicola*, and a xylanase gene from *P. ruminicola* has been cloned and expressed in *E. coli* [See Whitehead, et al., *Appl. Environ. Microbiol.*, 55:893–896 (1989)].

Recently, a naturally-occurring plasmid carrying a gene coding for tetracycline resistance has been identified ("pRRI4") in *P. ruminicola* 223/M2/7. The pRRI4 plasmid was shown to transfer from *P. ruminicola* 223/M2/7 into *P. ruminicola* F101, but not into *P. ruminicola* 23, by conjugation [Flint, et al., *Appl. Environ. Microbiol.*, 54:855–860 (1988)].

It has also been reported that the pRRI4 plasmid can be introduced into *P. ruminicola* F101 by electroporation, but not into *P. ruminicola* 118B, M384, GA33 by this method [Thomson and Flint, *FEMS Microbiol. Letters*, 61:101–104 (1989)]. This article also reports that pRRI4 isolated from *P. ruminicola* could not be introduced into *B. uniformis*, a colonic Bacteroides, by electroporation. Thomson and Flint also discloses that the *E. coli*-colonic Bacteroides shuttle vector pDP1 could not be introduced into *P. ruminicola* by electroporation. This was true whether pDP1 was extracted from *B. uniformis* or *E. coli*.

From the above discussion, it is clear that, prior to the present invention, the genetic manipulation of *P. ruminicola* was not possible. Little was known about the genetics of *P. ruminicola*, making the use of vectors that could be manipulated and amplified in a known host, such as *E. coli*, highly desirable. However, no shuttle vectors were known that could be used in *P. ruminicola*. Transformation and conjugal transfer of pRRI4 was possible, but pRRI4 cannot be used as a shuttle vector due to its relatively large size (19.5 kbp) and its inability to replicate in *E. coli*.

B. Tetracycline Resistance

Many bacteria, including strains of Bacteroides and Prevotella, possess tetracycline resistance genes. Three types of tetracycline resistance have been described and subdivided into classes defined by DNA-DNA hybridization.

The first type, tetracycline efflux, is mediated by a 40–50 kDa membrane protein which transports tetracycline out of the cell. Examples of this mode of resistance have been found in Gram-negative enterics [classes TetA-G; Aoki, *Micro. Sci.*, 5:219–223 (1988); Levy, *ASM News*, 54:418–421 (1988)] and some Gram-positive bacteria [classes TetK and TetL; Lacks, et al., *J. Mol. Biol.*, 192:753–765 (1986); McMurry, et al., *Antimicrob. Agents Chemother.*, 32:1646–1650 (1987)].

The second type of tetracycline resistance, ribosome protection, is mediated by a 72–75 kDa cytoplasmic protein which interacts with ribosomes and prevents inhibitory binding of tetracycline. Examples of this mode of resistance have been found in many Gram-positive and some Gram-negative bacteria [classes TetM and TetO; Burdett, *J. Bacteriol.*, 165:564–569 (1986); Manavathu, et al., *Gene*, 62:17–26 (1988); Sougakoff, et al., *FEMS Microbiol. Lett.*, 44:153–159 (1987)].

The third type of resistance, tetracycline modification, is mediated by a 44 kDa cytoplasmic protein which chemically inactivates tetracycline. The only known representative of this mode of resistance, class TetX, was orginally found in *B. fragilis* [Speer and Salyers, *J. Bacteriol.*, 170:1423–1429 (1988)].

Two other Tc$^r$ genes are known. TetN is an unsequenced streptococcal Tc$^r$ which is reported to confer ribosome protection type resistance [Burdett, *J. Bacteriol.*, 165:564–569 (1986)]. TetP is an uncharacterized Tc$^r$ determinant from *Clostridium prefringens* [Abraham, et al., *Plasmid*, 19:113–120 (1988)].

SUMMARY OF THE INVENTION

The invention provides for the first time a method for the genetic manipulation of *Prevotella ruminicola*. In particular, the present invention provides a method for introducing heterologous DNA into *P. ruminicola*. The method comprises transforming *E. coli* with a shuttle vector comprising: a mobilization region which permits transfer of the shuttle vector from *E. coli* to a colonic Bacteroides species; a mobilization region which permits transfer of the shuttle vector from the colonic Bacteroides species to a *P. ruminicola*; and heterologous DNA operatively linked to a promoter functional in *P. ruminicola*. After transformation of the *E. coli* with the shuttle vector, the *E. coli* is contacted with the colonic Bacteroides species under conditions sufficient so that the shuttle vector is transferred from the *E. coli* to the colonic Bacteroides species. Finally, the colonic Bacteroides species containing the shuttle vector is contacted with the *P. ruminicola* under conditions sufficient so that the shuttle vector is transferred from the colonic Bacteroides species to the *P. ruminicola*.

The invention also comprises *P. ruminicola* produced by this method and a shuttle vector useful for transferring heterologous DNA to *P. ruminicola* by conjugation. The shuttle vector comprises: a mobilization region which permits transfer of the shuttle vector from *E. coli* to a colonic Bacteroides species; a mobilization region which permits transfer of the shuttle vector from the colonic Bacteroides species to a *P. ruminicola*; and heterologous DNA operatively linked to a promoter functional in the *P. ruminicola*. These shuttle vectors are particularly advantageous because they can be amplified and manipulated in *E. coli* before they are used to introduce heterologous DNA *P. ruminicola*.

The invention further provides a tetracycline resistance gene of the TetQ class, or fragments thereof, that confer tetracycline resistance. The TetQ class is a new class of tetracycline resistance genes which confers tetracycline resistance by ribosome protection. The complete DNA sequence of one such gene has been determined and is presented below. The invention also comprises proteins of the TetQ class, or active fragments thereof, that provide tetracycline resistance by ribosome protection.

Finally, the invention provides a promoter functional in *P. ruminicola* and an engineered *P. ruminicola* comprising expressible foreign DNA.

BRIEF DESCRIPTION OF THE DRAWINGS

FIG. 5A is an autoradiogram of a polyapolyacrylamide SDS gel of in transcription-translation products. Lane 1 contains products from the vector control, pFD160. Shown also are products from Tc$^s$ deletion derivatives pNFD13-2ΔRV (lane 2) and pNFD13-2Δ5 (lane 3), reduced Tc$^r$ deletion derivative pNFD13-2Δ4 (lane 4), Tc$^r$ deletion derivatives pNFD13-14 2Δ3 (lane 5) and pNFD13-2Δ1 (lane 6), and intact pNFD13-2 (lane 7). The arrows in the right margin mark the two bands that were consistently unique to the SstI clone in maxicells. FIG. 5B shows an autoradiogram of soluble and membrane fractions from maxicells containing pNFD13-2: Lane 1, soluble fraction; Lane 2, membrane fraction.

FIG. 6 shows the deduced amino acid sequence of TetQ aligned with representatives of TetO (*Campylobacter jejuni*) and TetM (*Streptococcus faecalis*). The consensus of the sequenced ribosomal protection Tc$^r$ genes is displayed below these sequences. Upper case denotes conservation among the ribosome protection Tc$^r$ proteins. The four barred regions are regions of conservation in GTP-binding proteins [Halliday, *J. Nucleotide Prot. Phosphoryl. Res.*, 9:435–448 (1984)]. Positions marked (*) were found to be involved directly in GTP binding and are invariant in all GTP-binding proteins [Jurnak, *Science*, 230:32–36 (1985)].

FIG. 7 shows the upstream sequence of tetQ. The endpoints of the pNFD13-2 deletions shown in FIG. 4 are indicated by numbers above the sequence. Only the last three characters of the deletion designations are given. The first letter in parenthesis at each deletion denotes Tc$^r$ expression in *E. coli* (R=resistant; I=intermediate; S=sensitive). The letter following the slash denotes Tc$^r$ expression in Bacteroides. The *E. coli* consensus –35 and –10 sequences are indicated by lines above the tetQ sequence. Below the tetQ upstream sequence is shown the upstream consensus of the tetM sequences from *Staphylococcus aureus*, *Streptococcus faecalis*, and *Ureaplasma urealyticum* and the tetO sequences from *Campylobacter coli*, *Campylobacter jejuni*, and *Streptococcus*. Upper case letters denote bases that are conserved in all tetM and tetO sequences. Lower case letters denote bases that are not conserved in all cases, but are the consensus for that position. If data were not available for all six upstream sequences at a position, a lower case letter was used at that position.

DETAILED DESCRIPTION OF THE PRESENTLY PREFERRED EMBODIMENTS

Figure 1:
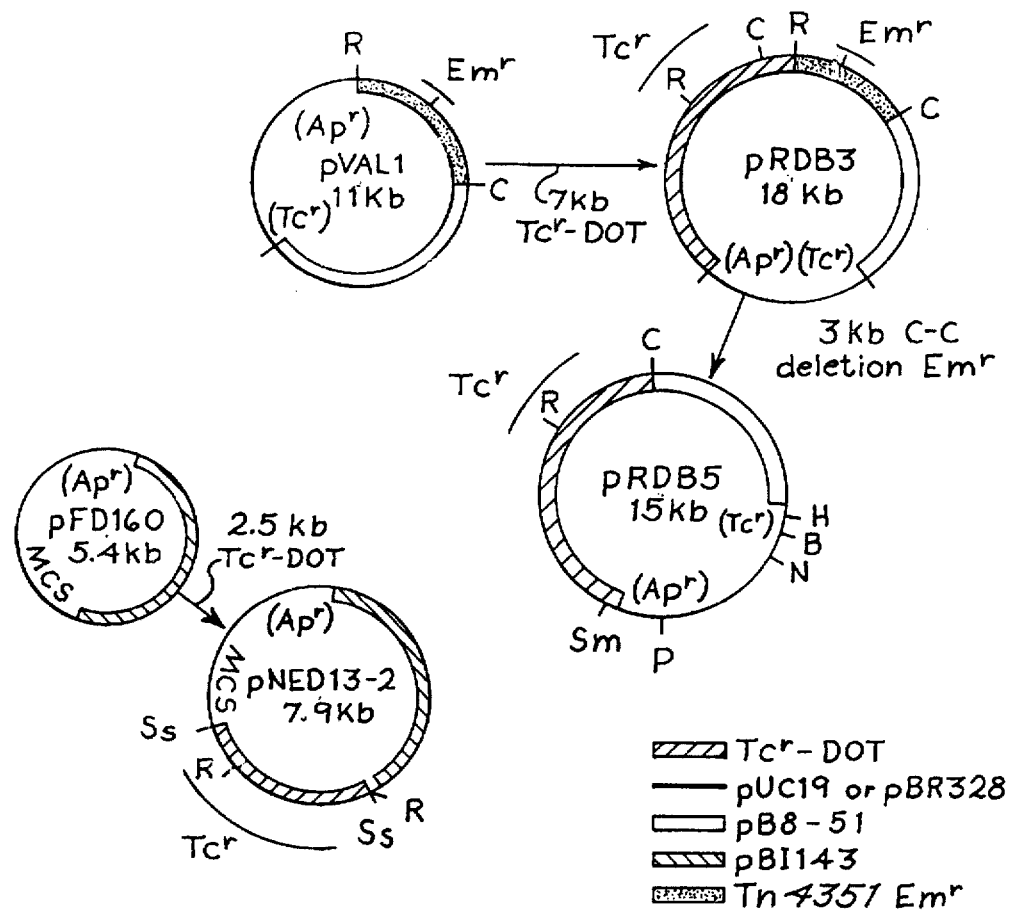
FIG. 1: A map of pVAL1 and a schematic diagram of the construction of pRDB3, pRDB5 and pNFD13-2. A partial map of the Tc$^r$Em$^r$ DOT element is indicated at the bottom of the figure, and the regions of this element which were cloned into the vectors are indicated by brackets under the map. Abbreviations for restriction sites are: R, EcoRI and C, ClaI. Only relevant restriction sites are shown: Ap$^r$= ampicillin resistance; Tc$^r$=tetracycline resistance; Em$^r$= erythromycin resistance.
Figure 1:
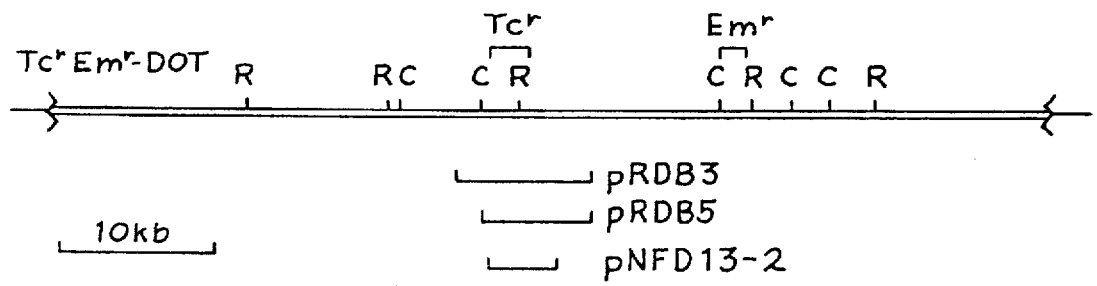

The method of the present invention involves conjugal transfer of shuttle vectors *Prevotella ruminicola*. As explained in the Background section, *Prevotella ruminicola* are strains of bacteria previously classified as *Bacteroides ruminicola*. The criteria for determining whether a bacterium should be classified as *B. ruminicola* have been loose in the past. Examples of very authentic *B. ruminicola* (now *P. ruminicola*) strains having characteristics quite different than the colonic Bacteriodes are B$_1$4, GA33, 23 and 118B. The degree of homology of 16S ribosomal RNA will probably be used as the standard to classify Bacteroides and Prevotella in the near future. Based on this standard, it is expected that B$_1$4, GA33, 23, 118B and bacteria whose 16S ribosomal RNA is at least 70% homologous with that of these strains will be classified as *P. ruminicola*.

The first step of the method of the invention is to transform an *E. coli* with a shuttle vector. Methods of transforming *E. coli* are well known in the art. Any strain of *E. coli* may be used, and numerous strains of *E. coli* are publicly available from such public depositories as the American Type Culture Collection (ATCC). The *E. coli* must have, or be engineered to have, a mobilization element which functions to transfer the shuttle vector from *E. coli* to a recipient colonic Bacteroides species. These elements may be introduced into *E. coli* using methods known in the art. Preferably, the mobilization element is an IncP plasmid, and most preferably the IncP plasmid R751. IncP plasmids such as R751 may be introduced into the *E. coli* by conjugation methods known in the art. Alternatively, *E. coli* strains, such as S17-1, are available which have the IncP plasmid inserted in their chromosomes.

Next, the *E. coli* is contacted with a species of colonic Bacteroides under conditions sufficient so that the shuttle vector is transferred from the *E. coli* to the colonic Bacteroides species. Methods of mating *E. coli* and colonic Bacteroides are known and include those described in Shoemaker, et al., *J. Bacteriol.*, 166:959–965 (1986) and Thomson and Flint, *FEMS Microbiol. Letters*, 61:101–104 (1989).

Any species of colonic Bacteroides may be used, and many species are available from public depositories, including the ATCC and the Virginia Polytechnic Institute (VPI) Anaerobe Collection (Blacksburg, Va.). The colonic Bacteroides species must contain, or be engineered to contain, a mobilization element which functions to transfer the shuttle vector from the colonic Bacteroides to *P. ruminicola*. These elements may be introduced into the colonic Bacteroides using methods known in the art such as conjugation. The mobilization element is preferably the conjugal element Tc$^r$Em$^r$ 12256. The Tc$^r$Em$^r$ 12256 element comprises approximately 120 kb of additional DNA not found in other Bacteroides conjugal elements. Although this segment of DNA has not been fully characterized, it is believed that it may enhance or increase efficiency of transfer. Most preferably, the colonic Bacteroides is *Bacteroides uniformis* containing the Tc$^r$Em$^r$ 12256 element.

The colonic Bacteroides species is then contacted with a strain of *P. ruminicola* under conditions sufficient so that the shuttle vector is transferred from the colonic Bacteroides species to the *P. ruminicola*. Many suitable species of *P. ruminicola* are available from public depositories, including the ATCC and the VPI Anaerobe Collection. A preferred *P. ruminicola* is B$_1$4.

Since *P. ruminicola* is extremely sensitive to oxygen, conjugation must take place under anaerobic conditions. Further, the use of a modifed E (ME) medium has been found critical to obtaining transconjugants. The composition of ME medium is given in Example 1 below.

The present invention also comprises shuttle vectors suitable for transferring heterologous DNA into *P. ruminicola*. A shuttle vector is a vector which contains one or more replicons which allow it to replicate in more than one type of organism. In particular, the shuttle vectors of the present invention must be able to replicate in *E. coli* and colonic Bacteroides. They my also be able to replicate in *P. ruminicola*, or the shuttle vectors, or fragments thereof, may integrate into the *P. ruminicola* chromosome.

Suitable *E. coli* replicons are well-known and include the pUC and pBR series of plasmids. Replicons suitable for use in colonic Bacteroides include pB8-51, pBFTM10, and pBI143 [Salyers, et al., *CRC Critical Reviews in Microbiology*, 14:49–71 (1987); Odelson, et al., *Plasmid*, 17:87–109 (1987); Smith, *J. Bacteriol.*, 164:294–301 (1985)]. It has been found that the pB8-51 replicon also functions in *P. ruminicola*. Other *P. ruminicola* replicons can be identified using the teachings herein and, e.g., the TetQ gene of the invention which is known to be expressed in *P. ruminicola*.

The shuttle vectors of the invention must also be capable of being transferred from *E. coli* to a colonic Bacteroides species. Accordingly, they must contain a mobilization region which permits this transfer. The mobilization region must be one which is acted on by the mobilization element present in the *E. coli* to effect the transfer. Suitable mobilization regions are known. They include those on pBFTM10 (pDP1, pCG30), pB8-51 (pEG920, pVAL1), and pBI143 (pFD160) which are mobilized by IncP plasmids [Salyers, et al., *CRC Critical Reviews in Microbiology*, 14:49–71 (1987); Odeleon, et al., *Plasmid*, 17:87–109 (1987); Shoemaker, et al., *J. Bacteriol.*, 166:959–965 (1986)].

The shuttle vectors must also be capable of being transferred from the colonic Bacteroides species to *P. ruminicola*, and they must contain a mobilization region which permits this transfer. The mobilization region must be one which is acted on by the mobilization element present in the colonic Bacteroides to effect the transfer. Suitable mobilization regions include the mobilization region of pB8-51 which is mobilized by Tc$^r$Em$^r$ 12256. Other mobilization regions can be identified using the teachings herein.

The shuttle vector also comprises heterologous DNA sought to be transferred *P. ruminicola* "Heterologous DNA" is defined herein to mean DNA from a source other than the *P. ruminicola* strain which is to receive the heterologous DNA. The heterologous DNA may include DNA encoding enzymes involved in the fermentation of carbohydrates in the rumen, enzymes involved in the degradation of polysaccharides (such as xylanase or polysaccharases), other enzymes involved in rumen metabolism, and enzymes or groups of enzymes that synthesize substances that are beneficial to growth of cattle such as antibiotics. By transferring heterologous DNA to *P. ruminicola*, new and useful traits may be imparted to the recipient *P. ruminicola*. These traits can include those which will lead to more economical beef production.

The heterologous DNA is operatively linked to a promoter functional in *P. ruminicola*. A preferred promoter is a promoter of a TetQ gene (see discussion of TetQ genes below). Another preferred promoter is from the Tc$^r$m$^r$ DOT element. A particularly preferred promoter comprises the sequence:

transformed *E. coli* from untransformed *E. coli* and to distinguish transconjugant colonic Bacteroides and *P. ruminicola* from non-transconjugants. It is also necessary to include selection markers that distinguish donor from recipient in mating mixtures. Many suitable selection markers are known and include antibiotic resistance, amino acid or other nutrient requirements, pH, and combinations of these. Preferred selection markers for *P. ruminicola* are TetQ tetracycline resistance genes. Especially preferred is the TetQ tetracycline resistance gene isolated from the Tc$^r$Em$^r$-DOT element whose sequence is given below.

The various components of the shuttle vector may be isolated or synthesized and then assembled using techniques that are well known in the art. Indeed, one the most important aspects of the present invention is that it allows for the engineering of DNA that is to be introduced *P. ruminicola*.

A preferred shuttle vector is pRDB5. The chimeric pRDB5 construct contains sequences from the plasmid pBR328, a cryptic colonic Bacteroides plasmid, pB8-51, and a colonic Bacteroides Tc$^r$ gene isolated from the Tc$^r$Em$^r$-DOT conjugal element. The restriction map of pRDB5 is shown in FIG. 1. Plasmid pRDB5 replicates in *E. coli*, colonic Bacteroides and *P. ruminicola*. Although it is not known whether pRDB5 replicates in, or transfers to, all colonic Bacteroides and *P. ruminicola*, this plasmid has a broad host range, and it is likely it can be used in many colonic Bacteroides and *P. ruminicola*.

In a preferred embodiment of the method of the present invention, *E. coli* were transformed with pRDB5. Then pRDB5 was mobilized from *E. coli* into *B. uniformis* by the IncP plasmid R751 which was present in the *E. coli*. Next, pRDB5 was conjugally transferred from *B. uniformis* to *P. ruminicola* B$_1$4 by the conjugal element Tc$^r$Em$^r$ 12256 present in the *B. uniformis*. A combination of in vitro selections was utilized to identify *P. ruminicola* B$_1$4 transconjugants. First, the *P. ruminicola* B$_1$4 recipient used was a rifampicin resistant mutant (rif$^r$) produced by growing *P. ruminicola* B$_1$4 on increasing levels of rifampicin to produce a spontaneous mutant. The rif$^r$ *P. ruminicola* B$_1$4 transconjugants could then be selected against donor *B. uniformis*, a species that is rifampicin sensitive. *B. uniformis* 1100 was chosen as a donor because it is a thymidine auxotroph, and the lack of thymidine in the selection medium could be used to select against that donor after matings with *P. ruminicola* B$_1$4. *B. uniformis* is also known to grow in medium containing vitamin K, whereas *P. ruminicola* B$_1$4 has no vitamin K requirement. Thus, vitamin K was also omitted from the selection medium. Finally, pH

```
AAAAATCCTC  CTACTTTTGT  TAGATATATT  TTTTTGTGTA  ATTTTGTAAT   50
CGTTATGCGG  CAGTAATAAT  ATACATATTA  ATACGAGTTA  TTAATCCTGT  100
AGTTCTCATA  TGCTACGAGG  AGGTATTAAA  AGGTGCGTTT  CGACAATGCA  150
TCTATTGTAG  TATATTATTG  CTTAATCCAA,                         180
                           [seq id no 1]
``` or active variants thereof. This promoter is the promoter region of the Tc$^r$ gene of the Tc$^r$Em$^r$ element of *B. thetaiotaomicron* DOT and my be isolated from that gene or may be prepared by chemical synthesis. This promoter region is also strongly believed to be sufficient to initiate transcription in *P. ruminicola*. "Active variants" are promoters which have deletions, additions and/or substitutions of nucleotides as compared to the above sequence, but which are still able to initiate transcription in *P. ruminicola*.

The shuttle vector will also include one or more selection markers. Selection markers must be used to distinguish was used in the selection method because *P. ruminicola* B$_1$4 grows well at pH 6.2, whereas *B. uniformis* does not grow well at pH values lower than 6.8. The combination of selection for antibiotic resistance, lack of thymidine and vitamin K, and low pH provided a relatively clean background for selecting *P. ruminicola* B$_1$4 transconjugants. The transconjugants were distinguished from non-transconjugant *P. ruminicola* B$_1$4 because they were tetracycline resistant due to the expression of the foreign Tc$^r$ gene on pRDB5. The *P. ruminicola* B$_1$4 transconjugants were also tested for other traits that characterize *P. rumini-* cola B₁4 and differentiate that strain from the donor *B. uniformis*. The results of the tests demonstrated that true *P. ruminicola* transconjugants containing pRDB5 were produced by the method of the invention.

The present invention also comprises transconjugant *P. ruminicola* prepared by the method of the invention and containing the shuttle vectors of the invention. A particularly preferred transconjugant is *P. ruminicola* containing pRDB5.

The invention further comprises a tetracycline resistance gene of the TetQ class, or fragments thereof that confer tetracycline resistance. The TetQ class is a new class of tetracycline resistance genes which confers tetracycline resistance by coding for proteins which protect ribosomes from the inhibitory binding of tetracyline.

The invention also comprises the proteins encoded by the TetQ genes (hereinafter "TetQ class of proteins"), or active fragments thereof. "Active fragments" of these proteins are fragments which are still capable of conferring tetracycline resistance. The DNA sequence of one TetQ gene (isolated from the Bacteroides conjugal element Tc$^r$Em$^r$-DOT) has been determined and is presented below in Example 2, along with the amino acid sequence of the protein encoded by the gene. The invention also comprises other DNA sequences which encode this same protein.

Hybridization studies using a portion of the sequenced gene indicates that TetQ genes are widespread in colonic Bacteroides. Given the stringency used in these experiments, it is estimated that the Tc$^r$ genes found in other Bacteroides Tc$^r$ strains share at least 80% identity with the sequenced gene. Also, the Tc$^r$ gene on the *P. ruminicola* plasmid pRRI4 appears to be a TetQ gene.

TetQ genes may be isolated from Bacteroides and Prevotella Tc$^r$ strains using known techniques. Alternatively, genes, or gene fragments, may be prepared using chemical synthesis.

Finally, the invention provides an engineered *P. ruminicola* containing expressible foreign DNA. "Foreign DNA" is used herein to mean DNA from a source other than *P. ruminicola*. Thus, "foreign DNA" is more narrow than "heterologous DNA," and heterologous DNA includes foreign DNA. "Engineered" is used to mean *P. ruminicola* not found in nature.

EXAMPLES

The restriction enzymes used in the following examples were obtained from Bethesda Research Laboratory, Gaithersburg, Md. They were used according to the manufacturer's instructions.

Example 1

A. Construction Of Shuttle Vectors

Four shuttle vectors were constructed. They were pRDB5, pVAL1, pRDB3, and pNFD13-2, shown in FIG. 1.

The vector pVAL1 carries the erythromycin resistance (Em$^r$) gene from the colonic Bacteroides transposon Tn4351 linked to portions of pBR328 (an *E. coli* replicon) and the cryptic Bacteroides plasmid pB8-51 (a colonic Bacteroides replicon). It was prepared as described in Valentine, et al., *J. Bacteriol*, 170:1319–1324 (1988). Briefly, pBR328 (available from Boehringer Mannheim) was digested with EcoRI. The EcoRI fragment of Tn4351 [preparation from pBF4 described in Shoemaker, et al., *J. Bacteriol.*, 162:626–632 (1985)] was ligated to the EcoRI-digested pBR328 to produce pTB1. Plasmid pB8-51 was isolated from *Bacteroides eggerthi* by standard plasmid isolation techniques [See Maniatis, et al., *Molecular Cloning: A Laboratory Manual*, (Cold Spring Harbor, N.Y. 1982)]. It was then partially digested with TagI. Next, ClaI digests of pTB1 were mixed with the TagI digests of pB8-51 and ligated with T4 DNA ligase to produce pVAL1.

Vector pRDB3 was prepared by cloning a 7 kbp HincII fragment from a cosmid clone of the Tc$^r$Em$^r$-DOT element into pVAL1. The cosmid clone was prepared as described in Shoemaker, et al., *J. Bacteriol.*, 171:1294–1302 (1989). Then the cosmid clone was digested with HincII, and the resulting 7 kbp fragment containing the Tc$^r$ gene was ligated to PvuII-digested pVAL1 to produce pRDB3.

Next, pRDB3 was digested with ClaI and religated to produce pRDB5. The result of this manipulation was to remove the Tn4351Em$^r$ gene.

The vector pNFD13-2 comprises pFD160 having a 2.7 kbp fragment containing the Tc$^r$ gene from Tc$^r$Em$^r$-DOT cloned into the SstI site. Plasmid pFD160 was prepared as described in Smith, *J. Bacteriol.*, 164:294–301 (1985). It consists of HaeII-cleaved pBI143 (a colonic Bacteroides replicon) ligated to NdeI-digested pUC19 (an *E. coli* replicon). The 2.7 kbp fragment containing the Tc$^r$ gene was prepared as follows. Tn1000 insertions into pRDB3 were used to create convenient restriction sites. Transposon mutagenesis was performed by transforming an *E. coli* strain carrying the F plasmid on which Tn1000 resides with pRDB3. Tn1000 causes cointegrates to form between pRDB3 and the F plasmid. During conjugation, F::pRDB3 cointegrates are transferred to a recipient. In the recipient, the cointegrates resolve, leaving the F plasmid and pRDB3 with a Tn1000 insertion.

Restriction digests of the resulting pRDB3::Tn1000 isolates were screened by standard techniques (Maniatis, et al., supra), and the smallest clone that would express Tc$^r$ in colonic Bacteroides was identified. This clone was the 2.7 kbp fragment containing the Tc$^r$ gene and was excised with SstI.

B. Transformation Of *E. coli*

*E. coli* donor strains were constructed by introducing pRDB5, pVAL1, or pNFD13-2 into *E. coli* DH5αMCR [obtained from Bethesda Research Laboratory] or S17-1 [obtained from R. Simon, Universitat Bielefeld, Postfach 86-40, D-4800 Bielefeld 1, FRG; described in Simon, et al., *Bio/Technology*, 1:784–791 (1983)]. The plasmids were introduced into the *E. coli* strains by transformation techniques previously described [See Maniatis, et al., supra]. The IncP mobilizing plasmid R751 [See Meyer, et al., *J. Bacteriol.*, 143:1362–1373 (1980)] was introduced into *E. coli* DH5αMCR by conjugation as described in Shoemaker, et al., *J. Bacteriol.*, 171:1294–1302 (1989); Thomson, et al., *FEMS Microbiol. Letters*, 61:101–104 (1989). *E. coli* S17-1 had a copy of the IncP plasmid RP4 already inserted in its chromosome. Both R751 and RP4 mobilize pRDB5, pVAL1, and pNFD13-2 from *E. coli* to *B. uniformis* at frequencies of 10⁻⁴ per recipient.

C. Preparation Of Colonic Bacteroides Donors

*B. uniformis* donor strains containing Tc$^r$m$^r$ element 12256 and pRDB5 (Tc$^r$) or pNFD13-2 (Tc$^r$) were constructed by first introducing the plasmid pRDB5 or pNFD13-2 into *B. uniformis* 1100 [obtained from the VPI Anaerobe Laboratory, Blacksburg, Va.], as described previously [Shoemaker, et al., *J. Bacteriol.*, 166:959–965 (1986); Thomson, et al., *FEMS Microbiol. Letters*, 61:101–104 (1989)], and selecting for tetracycline resistance. Transconjugants carrying the Tc$^r$ plasmid were used as recipients in a mating with *B. uniformis* 1008 (Tc$^r$Em$^r$) [obtained from the VPI Anaerobe Laboratory] to transfer the Tc$^r$Em$^r$ element 12256, with selection for Tc$^r$ and Em$^r$. The resulting strains were designated *B. uniformis* 1108 (pRDB5) and *B. uniformis* 1108 (pNFD13-2).

Similarly, to construct *B. uniformis* carrying the Tc$^r$Em$^r$ element 12256 and pVAL1 (Em$^r$), pVAL1 was first transferred from *E. coli* to *B. uniformis* 1100 by conjugation, with selection for Em$^r$. Then, the Tc$^r$Em$^r$ 12256 element was introduced by conjugation from *B. uniformis* 1008 to *B. uniformis* 1100 (pVAL1), with selection for Tc$^r$ and Em$^r$. The final strain was designated *B. uniformis* 1108 (pVAL1).

D. Mating With *P. ruminicola*

Next, the recipient, *P. rumimnicola* B$_1$4 (obtained from Marvin Bryant, Dept. of Animal Sciences, University of Illinois, Urbana, Ill.), was mated with *E. coli* or *B. uniformis*. *E. coli* donor strains were grown in Luria broth (LB) to an O.D. (650 mm) of 0.15–0.20. *B. uniformis* 1108 strains were grown in TYG-Thy-K broth in 80% nitrogen-20% carbon dioxide to an O.D. (650 nm) of 0.15–0.20. Optical densities were measured in 18 mm diemeter culture tubes in a Spectronic 20 spectrophotometer (Milton Roy Co., Rochester, N.Y.). TYG-Thy-K broth is tryptlcase-yeast extract-glucose broth [composition given in Holdeman, et al., *Anaerobe Laboratory Manual* (4th ed., Virginia Polytechnic Institute, Blacksburg, Va. 1977)] containing 100 μg/ml thymidine and 1 μg/ml vitamin K$_3$, with a final pH of 7.0–7.3.

*P. ruminicola* B$_1$4 was grown in MM10 broth at 80% nitrogen-20% carbon dioxide to an O.D. (650 mm) of 0.25–0.30. MM10 is similar to M10 medium previously described [*Anaerobe Laboratory Manual*, supra], except the concentration of trypticase and yeast extract was increased ten-fold and amylopectin was present as the carbohydrate source. Also, titanium citrate (0.15M) was added drop-wise until the resazurin became colorless (approximately 0.2–0.3 ml per liter of medium) prior to the addition of cysteine. The pH of this medium was 6.5–6.6. This medium, as were all media used for culturing *P. ruminicola*, was made in glass tubes sealed with a rubber stopper.

The *E. coli* or *B. uniformis* donor (30 ml) was centrifuged in a Sorvall GLC28 bench top centrifuge (SP/X rotor; Dupont Instruments, Wilmington, Del.) at 3,000 rpm for 15 minutes at room temperature to pellet the bacteria. The bacteria were then washed in 5 ml potassium phosphate buffer (0.1M, pH 7.0) and resuspended in 1 ml of TYG-Thy-K medium. Manipulations of *E. coli* or *B. uniformis* were performed under aerobic conditions.

*P. ruminicola* B$_1$4 (10 ml) was centrifuged in sealed culture tubes at 3,000 rpm for 15 minutes at room temperature as described above, and the supernatant fluid was removed with a sterile syringe.

The resuspended donor (*E. coli* or *B. uniformis*) (1 ml) and 5 ml of anaerobic 0.1M potassium phosphate buffer (pH 7.0) were injected into the tube. Anaerobic phosphate buffer was prepared by boiling phosphate buffer and cooling under a stream of oxygen-free carbon dioxide. After vortexing the tubes to dislodge the pelleted recipient, the bacterial mixture was centrifuged again in the sealed tubes, and the wash solution was withdrawn with a syringe. TYG-Thy-K medium (1.5 ml) and MM10 medium (1.5 ml) were injected into the tube, and the tube was vortexed to resuspend the bacteria. The resuspended mixture was injected into a sealed anaerobic tube containing a slant of modified E agar medium ("ME"), pH 6.8, for the mating. ME is the same as Sweet E medium previously described (*Anaerobe Laboratory Manual*, supra), except it contains glucose, as the only carbohydrate, and 100 ug/ml thymidine. Agar was added to a final concentration of 2%. The tubes were then centrifuged as described above to pellet the bacteria on the slants. The tubes were inverted gently, and the supernatant fluid removed with a syringe. The tubes were then incubated upside down at 37° C. for 15–18 hours.

After incubation, 1 ml of MM10 (pH 6.6), containing no thymidine or vitamin K was added to the slant tubes, and the tubes were vortexed. Next, resuspended bacteria were removed with a sterile syringe which had been gassed out with nitrogen-carbon dioxide.

To select for transconjugants, 0.1–0.2 ml of resuspended cells, or 0.1–0.2 ml of a 1:10 dilution, were inoculated into a roll tube containing MM10-Rif-Tc or MM10-Rif-Em selection medium. MM10-Rif (pH 6.2) medium consisted of MM10 containing 2% agar and 40 ug/ml rifampicin. For selection of transconjugants, either tetracycline (final concentration of 5 ug/ml) or erythromycin (final concentration of 5 ug/ml) was added to the MM10-Rif medium to produce MM10-Rif-Tc and MM10-Rif-Em, respectively.

To enumerate the total number of *B. uniformis* donors, 0.1 ml of a $10^{-6}$ dilution of the resuspended cells was plated on TYG-Thy-K agar plates and incubated in a GasPak jar. To enumerate the *E. coli* donors, 0.1 ml of a $10^{-6}$ dilution was plated on LB agar and incubated aerobically. To enumerate the *P. runinicola* B$_1$4 recipients, 0.1 ml of a $10^{-6}$ and a $10^{-8}$ dilution were inoculated into an MM10-Rif roll tube. All incubations were done at 37° C. for 3–4 days.

E. Results Of *E. coli-P. ruminicola* Matings

When the transfer of plasmids pVAL1, pNFD13-2, and pRDB5 from *E. coli* to *P. ruminicola* was attempted, no Tc$^r$ or Em$^r$ *P. ruminicola* transconjugants were detected. As a result, *B. uniformis* was used as an intermediate donor for *P. ruminicola* as described in the next section.

F. Results Of *B. uniformis-E. coli* Matings

*B. uniformis* 1108 (pRDB5), *B. uniformis* 1108 (pVAL1), or *B. uniformis* 1108 (pNFD13-2), prepared as described above, were mated with *E. coli* HB101 or EM24 to determine whether the *B. uniformis* recipients carrying a conjugal Tc$^r$Em$^r$ 12256 element and a plasmid were capable of mobilizing the plasmid at high frequency. The procedure for the *B. uniformis-E. coli* mating has been described previously [See Shoemaker, et al., *J. Bacteriol.*, 166:959–965 (1986); Thomson, et al., *FEMS Microbiol. Letters*, 61:101–104 (1989)]. Mobilization of these plasmids from *B. uniformis* to *E. coli* occurred at frequencies of $10^{-4}$–$10^{-5}$ per recipient (see Table 1 below).

G. Results Of *B. uniformis-P. ruminicola* Matings

To test for transfer of the plasmids from *B. uniformis* to *P. ruminicola* B$_1$4, a selective medium allowing growth of *P. ruminicola* abut not B. uniformis had to be developed. Being able to detect transfer frequencies as low as $10^{-9}$ per recipient was the criterion.

First, the antibiotic sensitivity of *P. ruminicola* B$_1$4 was tested. Minimal inhibitory concentrations for various antibiotics were determined by inoculating MM10 containing different concentrations of antibiotic and incubating for 48 hours. Antibiotic concentrations tested were 5, 10, 20, 50, 100 and 200 ug/ml. In the case of tetracycline and erythromycin, resistance levels on MM10 agar medium were also determined.

*P. ruminicola* B$_1$4 was found susceptible to rifampicin (10 ug/ml), tetracycline (2 ug/ml), erythromycin (1 ug/ml), gentamicin (20 ug/ml), and ampicillin (5 ug/ml). It was resistant to chloramphenicol (10 ug/ml), kanamycin (50 ug/ml), trimethoprim (200 ug/ml), and nalidixic acid (100 ug/ml).

*P. ruminicola* B₁4 was susceptible to all of the antibiotics which inhibited growth of *B. uniformis* except chloramphenicol. Accordingly, chloramphenicol was first used to select for *P. ruminicola* B₁4 and against the donor. Mixtures of *B. uniformis* and *P. ruminicola* B₁4 were plated on MM10 agar containing 10 ug/ml chloramphenicol. Donor *B. uniformis* colonies were still able to grow enough to obscure true transconjugants. Therefore, another resistance for selecting *P. ruminicola* recipients was required.

A spontaneous rifampicin resistant (Rif$^r$) mutant of *P. ruminicola* B₁4 was isolated by inoculating the bacteria into MM10 broth medium containing progressively higher concentrations of rifampicin. By growing *P. ruminicola* B₁4 on successively higher concentrations, a spontaneous mutant of *P. ruminicola* B₁4 was obtained which would grow in rifampicin concentrations as high as 60 ug/ml. The spontaneous Rif$^r$ mutant was determined to be a derivative of *P. ruminicola* B₁4 by comparing its NotI digest pattern with that of the original B₁4 strain. The restriction enzyme digest patterns were identical. This Rif$^r$ strain was used in matings to provide a selection for the *P. ruminicola*. This method of producing the rifampicin mutant is a well known method of producing antibiotic resistant mutants of bacteria, and other suitable *P. ruminicola* rifampicin resistant mutants can be produced in this manner.

However, using the Rif$^r$ derivative, *P. ruminicola* B₁4R, as a recipient and selecting for rifampicin resistance did not allow for the detection of transfer frequencies as low as $10^{-9}$ per recipient because spontaneous Rif$^r$ mutants of *B. uniformis* 1108 occurred at a frequency of $10^{-7}$.

Accordingly, a combination of selections had to be used. First, the *P. ruminicola* B₁4 rifampicin resistant mutant was used. *B. uniformis* 1100 was chosen as a donor because it is a thymidine auxotroph, and the lack of thymidine in the selection medium could be used to select against that donor after matings with *P. ruminicola* B₁4. However, spontaneous reversion to wild type occurs at relatively high frequencies ($10^{-6}$). *B. uniformis* is also known to grow in medium containing vitamin K, whereas *P. ruminicola* B₁4 has no vitamin K requirement. Thus, vitamin K was also omitted from the selection medium. Finally, pH was used in the selection method because *P. ruminicola* B₁4 grows well at pH 6.2, whereas *B. uniformis* does not grow well at pH values lower than 6.8. The combination of selection for antibiotic resistance, lack of thymidine and vitamin K, and low pH provided a relatively clean background for selecting *P. ruminicola* B₁4 transconjugants.

Using this selection medium and using a donor to recipient ratio of 1.5–3.0:1.0, Tc$^r$ transconjugants were detected in a mating between *B. uniformis* 1108 (pRDB5) and *P. ruminicola* B₁4 (Rif$^r$) at frequencies of $10^{-6}$–$10^{-7}$ per recipient (see Table 1). No transconjugants were detected in matings in which the donor was *B. uniformis* 1108 (pNFD13-2) or *B. uniformis* 1108 (pVAL1).

The ability of the transconjugants to grow in various media was tested to rule out the possibility that the apparent transconjugants were spontaneous Rif$^r$ or Rif$^r$Thy$^+$ mutants of the *B. uniformis* donor. Growth on TYG, no growth on TYG-Thy, no growth in MM10 containing gentamicin, and growth in MM10 containing xylan instead of glucose was observed. These phenotypic characteristics indicated that the transconjugants were of *P. ruminicola* origin rather than *B. uniformis*.

DNA analysis of *P. ruminicola* B₁4 transconjugants was performed. Plasmids were isolated from *P. ruminicola* B₁4 transconjugants by the Ish-Horowitz modification of the Birnbom and Doly procedure as described in Maniatis, et al., *Molecular Cloning: A Laboratory Manual* (Cold Spring Harbor Laboratory, Cold Spring Harbor, N.Y. 1982). Southern blots were also performed as described in Maniatis, et al., supra. Total DNA was prepared by standard methods as described in Saito, et al. *Biochem. Biophys. Acta*, 72:619–629 (1963); Shoemaker, et al., *J. Bacteriol.*, 171:1294–1302 (1989); Shoemaker, et al., *J. Bacteriol.*, 166:959–965 (1986).

Plasmid preparations made *P. ruminicola* from B₁4R had a background staining material that made it difficult to see plasmid DNA unambigiously. However, when a plasmid preparation was used to transform *E. coli* and pRDB5 was recovered in *E. coli*, the restriction profile of this plasmid was identical to that of the original pRDB5.

Figure 2A:
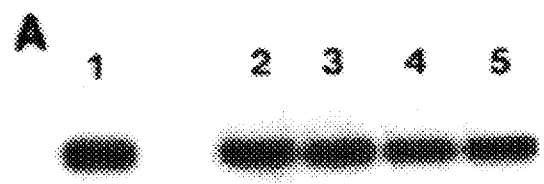
FIG. 2: Total DNA from the *B. uniformis* 1108 donor containing pRDB5 (lane 1), and four *P. ruminicola* B$_1$4 Tc$^r$ transconjugants (lanes 2–5) was digested with EcoRI. The Southern blot was probed with pFD160 which cross-hybridizes with pRDB5 but not with *P. ruminicola* B$_1$4 DNA.
FIG. 2B: Total DNA from the *P. ruminicola* B$_1$4R recipient (lane 2), the *B. uniformis* 1108 donor (lane 3) and one of the *P. ruminicola* B$_1$4 transconjugants (lane 4) was digested with EcoRI and HindIII. The Southern blot was probed with XBU4422::pEG920. This probe hybridizes not only with pBR328 sequences on pRBD5 but also with the Tc$^r$Em$^r$ 12256 element in the donor. The two bands corresponding to pRDB5 are indicated in lane 3 by arrows. Lane 1 contains DNA size standards. The largest four standards are 23.1 kb, 9.4 kb, 6.7 kb and 4.4 kb, respectively.

Additionally, total DNA (plasmid plus chromosome) was isolated from apparent *P. ruminicola* transconjugants, digested with EcoRI and subjected to Southern blot analysis. EcoRI cuts once in pRDB5 to produce a 15 kb linear segment. The DNA digests were separated on a 1.0% agarose gel and blotted onto Optibind (Schleicher and Schuell). The digests were then probed with $^{32}$P-labelled pFD160. The pFD160 plasmid hybridizes with the pBR328 sequences in pRDB5, but not with the Tc$^r$ gene. All of the putative transconjugants contained a single band of the correct size which hybridized with the probe (see FIG. 2A).

Figure 2B:
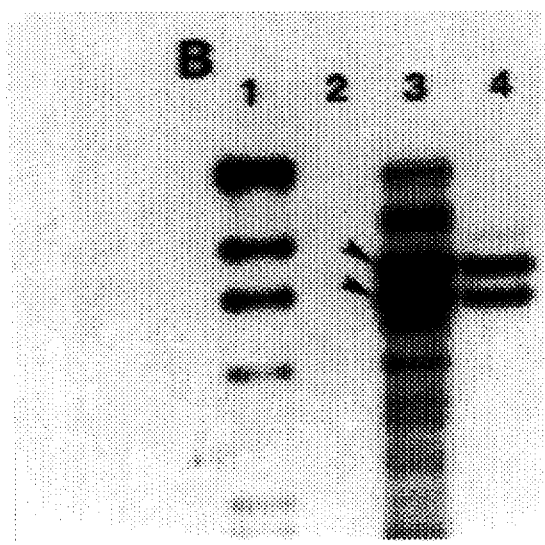

Total DNA from *B. uniformis*, *P. ruminicola* B₁4, and *P. ruminicola* transconjugants were also digested with HindIII and EcoRI restriction enzymes, and the digests blotted onto Optibind. The blot was hybridized with labelled XBU4422::pEG920 [prepared as described in Shoemaker, et al., *J. Bacteriol.*, 172:1694–1702 (1990)], a probe which detects pRDB5 and the Tc$^r$Em$^r$ 12256 element. If the apparent transconjugants were Thy$^+$Rif$^r$ mutants of *B. uniformis* 1108 (pRDB5), the Southern blot would show a number of bands, including the two bands produced from a HindIII-EcoRI digest of pRDB5. As can be seen from FIG. 2B, a mixture of bands due to pRDB5 and the Tc$^r$Em$^r$ 12256 element was seen in the *B. uniformis* donor, whereas only the bands associated with pRDB5 were seen in the transconjugant. These results indicated that the transconjugants were not revertants of the *B. uniformis* donor.

Figure 3:
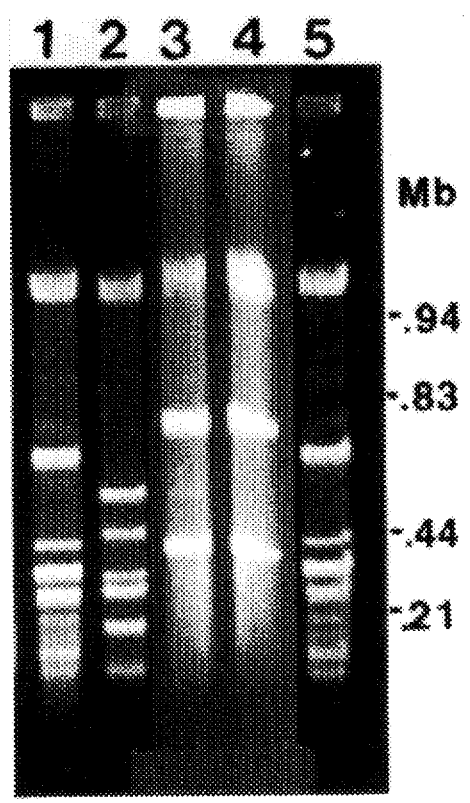
FIG. 3: Results of pulse field electrophoresis to verify the identity of *P. ruminicola* B$_1$4 Tc$^r$ transconjugants. NotI digests of DNA from the donor, *B. uniformis* 1108 carrying pRDB5, are shown in lanes 1 and 5. NotI digested DNA from *P. ruminicola* GA33 (lane 2), B$_1$4R (lane 3) and one of the B$_1$4 pRDB5 transconjugants (lane 4) are also shown. The NotI pattern of *P. ruminicola* B$_1$4 is identical to that of B$_1$4R (data not shown). The migration distances of some of the yeast chromosome size standards are shown in megabases (Mb) at the side of the gel.

The NotI restriction enzyme digest patterns of DNA from *B. uniformis*, *P. ruminicola* B₁4R, and a *P. ruminicola* B₁4 transconjugant were compared on pulsed field gels to determine whether a Tc$^r$ contaminant having properties similar to *P. ruminicola* had been isolated instead of true transconjugants. The NotI digest pattern of *P. ruminicola* B₁4 differs not only from that of *B. uniformis* 1108, but also differs from that of other *P. ruminicola* strains (data not shown). As shown in FIG. 3, the NotI restriction patterns of the *P. ruminicola* B₁4R recipient and the Tc$^r$ transconjugant were identical to each other and to that of *P. ruminicola* B₁4.

The combined data show that true *P. ruminicola* transconjugants were obtained.

No transfer of pNFD13-2 to *P. ruminicola* B₁4 was detected. Since pNFD13-2 has the same Tc$^r$ gene as pRDB5 but derives its replication region from a different plasmid, the lack of transconjugants was most likely due to failure of the pNFD13-2 replication origin (pBI143) to work in *P. ruminicola* B₁4. However, there is a 4 kbp region upstream of the Tc$^r$ gene which is present in pRDB5 but not in pNFD13-2. This region seems to have no effect on expression of the Tc$^r$ gene in *B. uniformis*, but it might affect expression in *P. ruminicola* B₁4. Since pNFD13-2 was mobilized from *B. uniformis* to *E. coli* at frequencies comparable to mobilization frequencies seen with pEDB5, it is possible that pNFD13-2 is getting into but is lost because it cannot replicate. If so, pNFD13-2 could serve as a suicide vector for introducing DNA into the chromosome of *P. ruminicola* B₁4.

Genetic manipulation of *P. ruminicola* would be easier if *E. coli* were the donor. Failure to demonstrate transfer of pRDB5 from *E. coli* to *P. ruminicola* could be due to the failure of IncP plasmids to mediate formation of mating pairs between *E. coli* and *P. ruminicola*. However, since IncP plasmids mediate mating between *E. coli* and the colonic Bacteroides strains, this seems unlikely. A more likely possibility is that the transfer frequency is lowered by the anaerobic mating conditions. Aerobic matings with the oxygen-sensitive *P. ruminicola* are not feasible. Nonetheless, it may be possible to find conditions that raise the frequency of mating and allow *P. ruminicola* to survive. Finally, restriction enzymes in *P. ruminicola* may prevent survival of pRDB5 introduced from *E. coli*.

TABLE 1

Transfer frequencies of various shuttle vectors from *B. uniformis* to either *B. ruminicola* B₁4 or *E. coli*.

| Donor strain | Frequency of transfer from *B. uniformis* to | |
|---|---|---|
| | *E. coli* | *B. ruminicola* |
| *B. uniformis* 1108 (pRDB5) | $3 \times 10^{-4a}$ | $10^{-7} - 10^{-6}$ |
| *B. uniformis* 1108 (pNFD13-2) | $1 \times 10^{-4}$ | $<10^{-9}$ |
| *B. uniformis* 1108 (pVAL1) | $1 \times 10^{-4}$ | $<10^{-9}$ |
| *B. uniformis* 1104 (pRBD3) | $1 \times 10^{-4}$ | $<10^{-9}$ |
| *B. uniformis* 1108 (pRDB5-2)$^b$ | $2 \times 10^{-4}$ | $10^{-7} - 10^{-6}$ |

$^a$Frequencies are given as transconjugants per recipient. Numbers represent the mean of at least three separate experiments.
$^b$pRDB5-2 is pRDB5 isolated from a *B. ruminicola* B₁4 transconjugant in the *B. uniformis* 1108 background.

EXAMPLE 2

The Bacteroides Tc$^r$ gene, originally derived from the Bacteroides conjugal element Tc$^r$Em$^r$-DOT [Shoemaker, et al., *J. Bacteriol.*, 171:1294–1302 (1989)], was subcloned on a 2.7 kbp fragment, and the 2.7 kbp fragment was sequenced. The complete sequence of the fragment is shown below in Chart A. Computer analysis of the DNA sequence, translation into amino acid sequence, and comparisons to amino acid sequences of other tetracycline resistance peptides were performed. The amino acid sequence of the gene product is presented below in Chart B. A promoter region functional in Bacteroides species was identified. Its sequence is shown below in Chart C. This promoter region is also strongly believed to be sufficient to initiate transcription in *P. ruminicola*.

The gene coded for a protein of the ribosome protection type of tetracycline resistance. However, the amino acid sequence coded for by the cloned gene was found to be only about 40% identical to sequences coded for by the TetM and TetO genes, two known classes of ribosome protection type tetracycline resistant genes. Accordingly, it was concluded that the Bacteroides Tc$^r$ was clearly in a separate DNA-DNA hybridization class from TetM and TetO and constituted its own DNA hybridization class. This new class of tetracycline resistance genes is designated TetQ. The experiments and analyses performed, and the Bacteroides Tc$^r$ gene and its gene product, will now be described in detail.

A. Materials and Methods

1. Strains and growth conditions

Strains used in this study are listed in Table 2. *E. coli* DH5α was obtained from Bethesda Research Laboratory. *B. thetaiotaomicron* strains BT 4001, BT4002, BT4004, BT4007 and BT4008 and *B. uniformis* BU10001 are described in Shoemaker and Salyers, *J. bacteriol.*, 170:1651–1657 (1988). *B. thetaiotaomicron* strains 5482 and 2808, *B. uniformis* strains C7-17, 3537, T1-1, *B. distasonas* strains 4243, C30-45, 6308, and *B. caccae* strains 3452A and 8608 are described in Johnson, *J. Syst. Bacteriol.*, 28:245–256 (1978). *B. fragilis* AK87 was obtained from A. Kuritza, Yale University Medical School, New Haven, CT. *E. coli* LCD44 was obtained from Dr. John Cronon, Jr., University of Illinois, Urbana, Ill.

Bacteroides strains were grown either in prereduced Trypticase (BBL Microbiology Systems) -yeast extract-glucose (TYG) [Holdeman, et al., *Anaerobe Laboratory Manual*, supra] under an 80% $N_2$/20% $CO_2$ atmosphere or on TYG agar plates in a GasPak jar. *E. coli* strains were grown in Luria broth (LB) or on LB agar plates unless otherwise indicated.

2. Plasmids

The preparation of pNFD13-2 is described above in Example 1. As discussed there, it contains a 2.7 kbp insert containing the Tc$^r$ gene of the Tc$^r$Em$^r$-DOT element. Plasmid pNFD13-6 is identical to pNFD13-2, but with the 2.7 kbp insert in the opposite orientation.

3. DNA isolation and analysis

Plasmids were isolated from *E. coli* by the Ish-Horowitz modification of the Birnboim and Doly method [Maniatis, et al., supra]. Chromosomal DNA from Bacteroides was isolated by the method of Saito and Miura, *Biochim. Biophys. Acta*, 72:619–629 (1963). Restriction digestion and ligation with T4 DNA ligase followed standard procedures (Maniatis, et al., supra). Electrophoretic resolution of restriction digests was done in 0.8–1.0% agarose slab gels in 1× or 4× GGB (1×:0.04M Tris, 0.02M sodium acetate, 0.002M EDTA). Gels were stained with ethidium bromide (1 µg/ml) and photographed. Plasmids were introduced into *E. coli* employing the transformation procedure of Lederberg and Cohen, *J. Bacteriol*, 119:1072–1074 (1974).

4. Southern hybridization

For Southern blot hybridization analysis, DNA was digested with restriction enzymes and electrophoresed on a 1% agarose gel. The DNA was transferred to Millipore HAHY nitrocellulose paper by capillary blotting (Maniatis, et al., supra). Nick translation was used to label DNA probes with [α-$^{32}$P]-dCTP [Rigby, et al., *J. Mol. Biol.*, 113:237–251 (1977)]. Probes were hybridized to DNA on the nitrocellulose paper for 24 hours at 42° C. in a hybridization solution containing 50% formamide (Maniatis, et al., supra). Following hybridization, blots were washed twice for 30 minutes each with 2× SSC (0.3M NaCl and 0.03M sodium citrate) containing 0.2% sodium dodecyl sulfate (SDS), then twice with 0.2% SDS in 0.5× SSC at 60° C. Blots were then analyzed using autoradiography.

5. Minimum Inhibitory Concentration (MIC) of tetracycline

To test for expression of the 2.7 kbp clone of the Tc$^r$ gene and its various deletion derivatives in *E. coli* and *B. thetaiotaomicron*, MIC values were determined. When *E. coli* was the host, ampicillin (100 µg/ml) or tetracycline (3 µg/ml) was added to inoculum cultures to maintain plasmids in plasmid-bearing strains. In most experiments, MIC values were determined using the tube dilution method. Cells (0.1 ml) from overnight inoculum cultures were introduced into LB broth medium containing serially incremented concentrations of tetracycline. Increments of 5 µg/ml were used. Tubes were incubated at 37° C. and scored visually for growth at 12 and 24 hours. In some experiments, the level of resistance was determined by patching cultures onto LB agar plates containing different concentrations of antibiotic and scoring growth after 24 hours.

To test for expression in Bacteroides, vectors containing various subclones of the 2.7 kbp clone of the Tc$^r$ gene were mobilized into *B. thetaiotaomicron* as described previously [Shoemaker, et al., *J. Bacteriol.*, 171:1294–1302 (1989); Shoemaker, et al., *J. Bacteriol.*, 162:626–632 (1985)], with selection for Tc$^r$. Transfer frequencies were several logs above background. Thus, failure to obtain a Tc$^r$ transconjugant was a reasonable indication that the deletion clone failed to express Tc$^r$ in Bacteroides. In Bacteroides, MIC determinations were done in TYG broth medium with serially incremented concentrations of tetracycline.

6. Maxicells

The maxicell procedure was executed as described by Sancar, et al., *J. Bacteriol*, 137:692–693 (1979), with *E. coli* LCD44 as host. Samples were solubilized by incubation in SDS or lithium dodecyl sulfate solubilizing solution at 37° C. to avoid possible aggregation. Proteins from maxicells were separated by electrophoresis on 11% highly cross-linked SDS polyacrylamide gels as described by Hashimoto, et al., *Anal. Biochem.*, 112:192–199 (1983). Following electrophoresis, gels were stained with Fast Stain (Zoion Research Inc., Allston, Mass.), dried onto filter paper under vacuum, and autoradiographed. Molecular weight markers from BRL, Gaithersburg, Md., were used for size estimation. Maxicell fractionation was performed using an adaptation of the method of Tai and Kaplan, *J. Bacteriol.*, 164:83–88 (1985).

7. In vitro transcription and translation

Proteins encoded by plasmid templates were compared using an *E. coli*-derived in vitro transcription-translation system [DeVries and Zubay, *Proc. Nat. Acad. Sci. USA*, 57:1010–1012 (1967)] in kit form (Amersham, Arlington Heights, Ill.). Radiolabeled proteins were resolved on 11% highly cross-linked SDS polyacrylamide and detected by autoradiography as described above.

8. DNA sequencing and analysis

Figure 4:
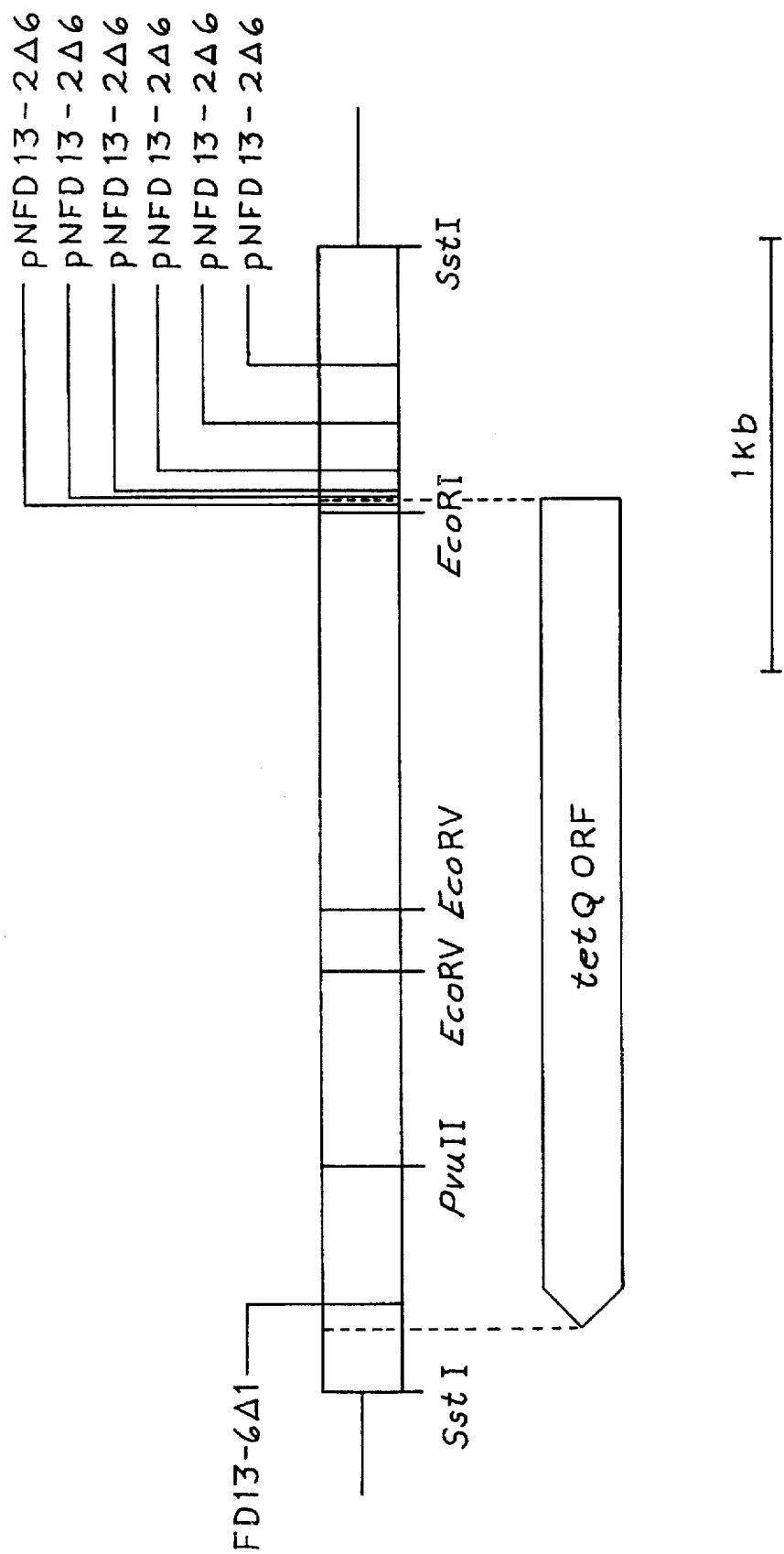
FIG. 4 is a partial restriction map of the 2.7 kbp SstI clone of the Tc$^r$ gene from *B. thetaiotaomicron* DOT. Important deletion derivatives are indicated by the labeled brackets. The orientation and extent of the large open reading frame encoding TetQ are indicated below by the arrow.

The region sequenced in this study was the 2.7 kbp SstI fragment from pNFD13-2 and pNFD13-6. Progressive unidirectional deletions were introduced into the insert DNA using an adaptation of the exonuclease III procedure of Henikoff, *Gene*, 28:351 (1984), provided in kit form (Erase-a-Base System by Promega, Madison, Wis.). (See FIG. 4) Both strands were sequenced by the dideoxy chain termination reaction with the T7 DNA polymerase variant and reagents provided in the Sequenase 2.0 kit (U.S. Biochemicals, Cleveland, Ohio). Computer analysis of DNA sequence, translation into amino acid sequence and comparisons to amino acid sequences of other tetracycline resistance peptides were performed using Genetics Computer Group (GCG) software (Devereux, et al., *Nucl. Acids Res.*, 12:387–395 (1985)) on a MicroVAX computer system. The sequences of tetracycline resistance and elongation factor genes used in this study were obtained from GenBank and are listed with accession numbers in Table 3.

B. Results

1. Expression of the Bacteroides tetracycline resistance gene in *E. coli*

The Tc$^r$ gene from *B. thetaiotaomicron* DOT was localized to a 2.7 kbp SstI fragment in the constructs ppNFD13-2 and pNFD13-6, which contained the insert in opposite orientations. Though these plasmids were originally constructed to test for expression in Bacteroides, we examined them for expression in *E. coli* because it was possible that the lac promoter adjacent to the cloned SstI fragment would drive Tc$^r$ expression in *E. coli*. Because *E. coli* carrying low copy number cosmid clones of the Tc$^r$ gene did not grow on LB plates containing 5 or 10 µg/ml tetracycline, Shoemaker, et al. had reported that the Bacteroides Tc$^r$ gene did not function in *E. coli* [Shoemaker, et al., *J. Bacteriol.*, 171:1294–1302 (1989)]. However, it was found that the 2.7 kbp SstI insert in the higher copy number pUC19-based vector, pFD160R, allowed *E. coli* to grow on LB agar plates containing 5 µg/ml tetracycline.

Following pregrowth in LB containing 100 µg/ml ampicillin, *E. coli* DH5α carrying the SstI clone had a tetracycline MIC value of 40 µg/ml for pNFD13-2 and a value of 25 µg/ml for pNFD13-6. However, when the inoculum culture was grown in LB containing sub-inhibitory tetracycline (1 µg/ml), differences in MIC between the clones diminished; the MIC values for pNFD13-2 and pNFD13-6 were 50 µg/ml and 40 µg/ml, respectively. The fact that the MIC values of both orientations were comparable indicated that the promoter being recognized was on the cloned fragment, and therefore was not the lac promoter. Moreover, addition of IPTG to the growth medium had no effect upon MIC levels. Interestingly, MIC values obtained on LB agar plates for *E. coli* bearing pNFD13-2 and pNFD13-6 were significantly lower than the values obtained in broth medium (plate MIC of 10 µg/ml for pNFD13-2).

2. Localization of the Bacteroides Tc$^r$ gene

Initially, two deletions in the 2.7 kbp SstI segment were created by digesting pNFD13-2 with EcoRV and religating to form pNFD13-2ΔRV and by digesting pNFD13-6 with EcoRI and religating to form pNFD13-6ΔRI. The MIC of DH5α bearing pNFD13-2ΔRV or pNFD13-6ΔRI was the same as that for DH5α without plasmid (2 μg/ml). Loss of resistance in both deletions indicated that the Tc$^r$ gene spanned the internal 0.9 kbp EcoRI-EcoRV region of the SstI clone. Further localization of the gene was undertaken using exonuclease III to create progressive unidirectional deletions in the 2.7 kbp SstI insert from the pFD160 polylinker. (See FIG. 4) Deletion pNFD13-2Δ3, which extended from the right to within 100 bp of the EcoRI site, did not affect resistance in *E. coli*. Deletion pNFD13-2Δ4, which extended to within 50 bp of the EcoRI site, decreased the MIC without completely eliminating resistance. Deletions into or through the EcoRI site abolished Tc$^r$ in *E. coli*. Deletion pNFD13-6Δ1, which extended 200 bp into the other end of the SstI fragment, also abolished Tc$^r$. Thus, it appeared that the genetic information essential for Tc$^r$ expression in *E. coli* spanned a 2.1 kbp region in the SstI insert DNA.

A larger region was required for Tc$^r$ expression in Bacteroides than in *E. coli*. Deletion construct pNFD13-2Δ3, which conferred full resistance on *E. coli*, did not confer resistance on Bacteroides. The largest of the exonuclease III deletions from the right which retained full Tc$^r$ activity in.was pNFD13-2Δ2. Thus, it appeared that an additional region of approximately 200 bp was required for expression in Bacteroides.

3. Size and cellular location of the Tc$^r$ gene product

Figure 5A:
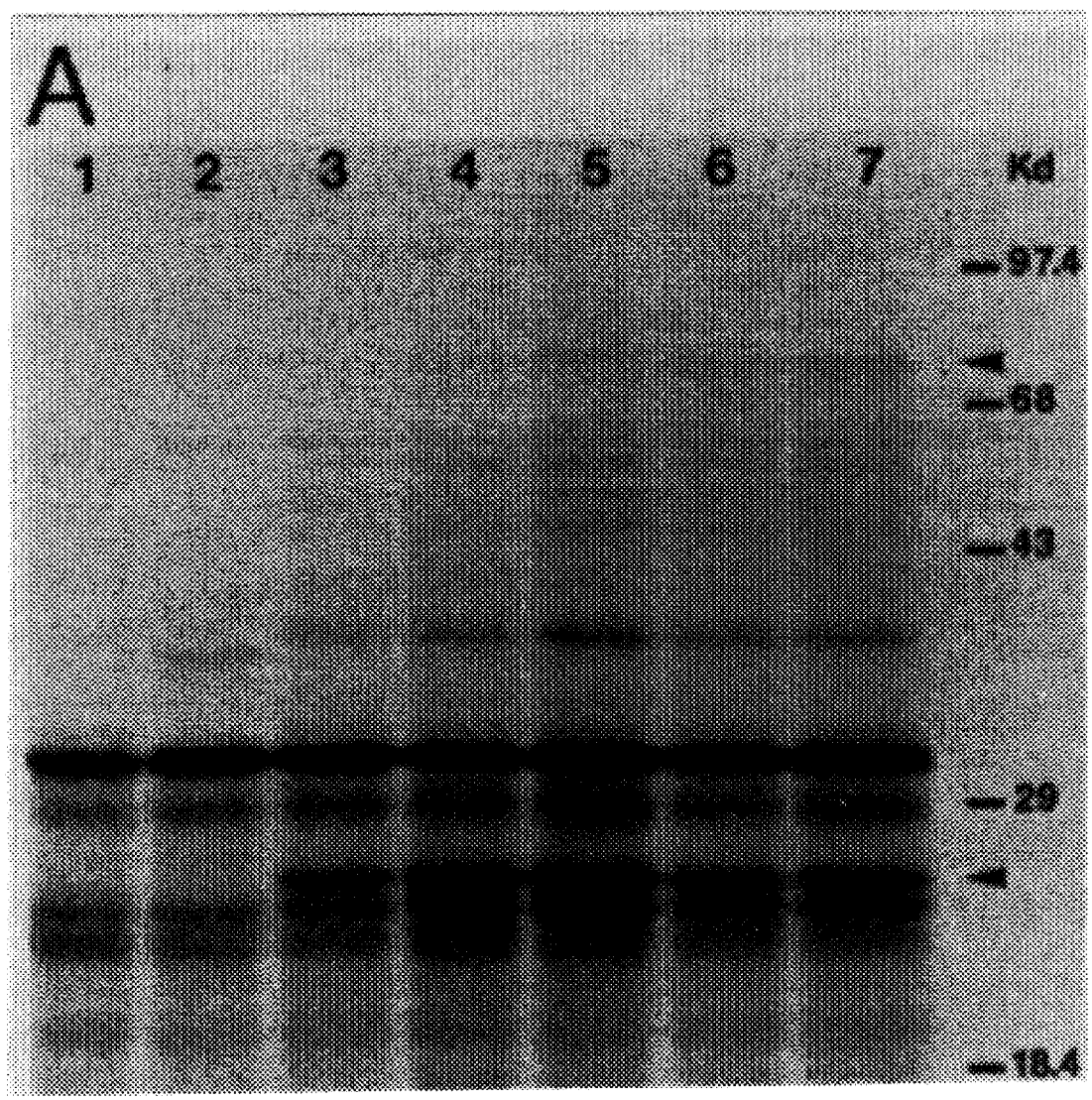
FIGS. 5A and 5B show products of the 2.7 kbp SstI clone in *E. coli*.

In maxicell experiments, two major proteins were associated with the cloned 2.7 kbp SstI fragment. These were estimated to have molecular weights of 76 and 25.5 kDa (data not shown). The two proteins were also seen when pNFD13-2 and its deletion derivatives were used as templates in an in vitro transcription-translation system. (See FIG. 5A) Appearance of the 76 kDa band coincided with Tc$^r$ expression in *E. coli*. That is, the 76 kDa band was present in deletions that still conferred resistance on *E. coli* (pNFD13-2Δ1, pNFD13-2Δ3), was consistently fainter in the deletion which conferred reduced resistance (pNFD13-2Δ4), and was missing in the Tc$^s$ deletions (pNFD13-2Δ5, pNFD13-2Δ6). By contrast, the 25.5 kDa band was produced from the Tc$^s$ deletions pNFD13-2Δ5 and pNFD13-2Δ6. The Tc$^s$ deletion in pNFD13-2ΔRV resulted in the loss of both of the major proteins associated with the SstI insert. Some additional proteins that were unique to the SstI clone were seen with the in vitro transcription-translation system, but these were also present in the Tc$^s$ deletions pNFD13-2Δ5 and pNFD13-2Δ6. Moreover, these proteins were not seen in the maxicell extracts.

Figure 5B:
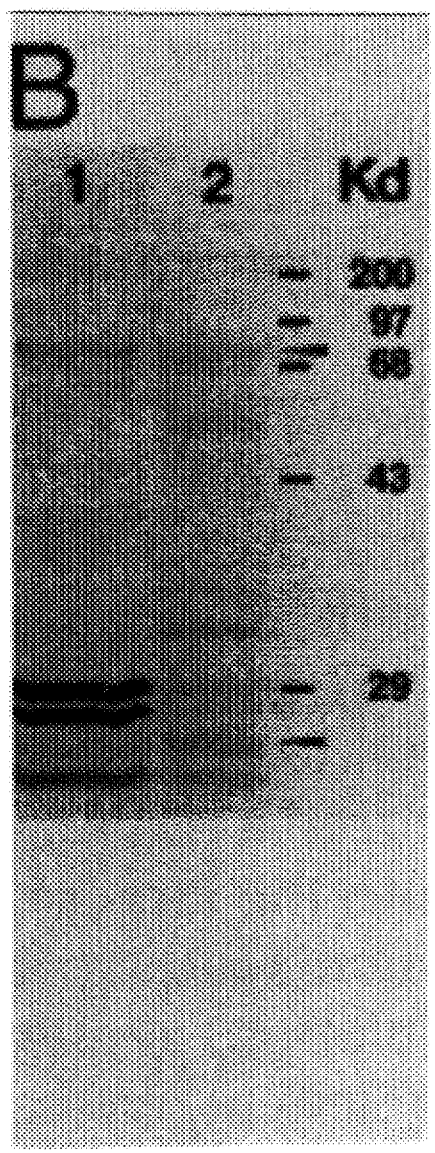

Cellular localization of the 76 kDa band by fractionation of maxicell extracts indicated that this protein partitioned predominately with the soluble fraction. (See FIG. 5B) However, a portion of the protein partitioned with the membrane fraction. The 25.5 kDa band clearly partitioned with the membrane fraction.

4. Relatedness to other Bacteroides tetracycline resistances

Tetracycline resistance has been found to be widespread among strains of colonic Bacteroides. Previous hybridization studies of the Tc$^r$ conjugal elements resident in different Tc$^r$ colonic Bacteroides isolates have revealed extensive DNA hybridization [Shoemaker, et al., *J. Bacteriol*, 171:1294–1302 (1989)]. To determine if the Tc$^r$ genes in other clinical strains were similar to the Tc$^r$ gene from *B. thetaiotaomicron* DOT, Southern hybridization was performed using the internal 0.9 kbp EcoRI-EcoRV segment of the Tc$^r$ gene to probe chromosomal DNA preparations digested with EcoRV and EcoRI. The Tc$^r$ strains analyzed were clinical isolates of *B. fragilis, B. thetaiotaomicron, B. uniformis, Bacteroides caccae*, and *Bacteroides distasonas* from the continental U.S., Hawaii and Japan. The 0.9 kbp probe hybridized with a 0.9 kbp band in all but one of the Tc$^r$ isolates probed. The only exception to this was *B. distasonas* C30-45, in which the probe hybridized to a fragment much larger than 0.9 kbp. This could be due to the modification or loss of one of the two restriction sites in C30-45. In another *B. distasonas* isolate, 6308, the probe hybridized strongly to a 0.9 kbp band. *B. fragilis* V479 exhibited weak hybridization relative to the other strains, but the cross-hybridizing band was the same 0.9 kbp size as the probe. The probe did not hybridize to DNA from Tc$^s$ type strain controls. These results indicated that the gene cloned in the 2.7 kbp SstI fragment is widespread among clinical isolates of colonic Bacteroides species. Given the stringency used in these experiments, it is estimated that the Tc$^r$ genes found in other Tc$^r$ strains of Bacteroides share at least 80% identity with the Tc$^r$ gene from *B. thetaiotaomicron* DOT.

5. DNA Sequence

The DNA sequence of the 2.7 kbp SstI fragment was obtained. The sequence of the entire fragment is presented in Chart A below.

Only one open reading frame within the SstI clone was sufficiently large to encode a protein of the estimated 76 kDa. (See FIG. 4) All other open reading frames in the fragment were less than 400 bp. The start codon of the large open reading frame was 22 bp to the right of the EcoRI site in FIG. 1. The open reading frame spanned the 0.9 kbp EcoRI-EcoRV region, which was determined to be internal to the Tc$^r$ gene. The location and extent of the open reading frame were also consistent with the exonuclease III deletion results. No additional open reading frames were found that might encode the 25.5 kDa protein seen in maxicells and in vitro transcription-translation. Presumably this protein was produced by a fusion between insert and vector DNA.

The TetQ open reading frame codes for a protein of 642 amino acids (deduced molecular weight, 72,100 Da). The amino acid sequence of the protein is given below in Chart B. The tetQ gene had 40.1 mol % G+C, compared to 42 mol% G+C of the chromosome of *B. thetaiotaomicron*, the species from which the Tc$^r$ gene was cloned [Johnson, *J. Syst. Bacteriol.*, 28:245–256 (1979)].

6. Relatedness to previously sequenced Tc$^r$ proteins

The length of the deduced Bacteroides Tc$^r$ protein was similar to the lengths of proteins encoded by tetM and tetO [Martin, et al., *Nucl. Acids Res.*, 14:7047–7058 (1986); Nesin, et al., *Antimicrob. Agents Chemother.*, in press; Sanchez-Pescador, et al., *Nucl. Acids Res.*, 16:1216–1217 (1988); LeBlanc, et al., *J. Bacteriol.*, 170:3618–3626 (1988); Manavathu, et al., *Gene*, 62:17–26 (1988)], which range from 638 amino acids to 640 amino acids. Comparisons of the Bacteroides Tc$^r$ amino acid sequence to those of TetM and TetO revealed extensive regions of similarity. (See FIG. 6) However, the amino acid sequence of the Bacteroides Tc$^r$ protein was less closely related to the amino acid sequences of TetM and TetO (40.1–40.3% identity) than these sequences are to each other (75.6–76.9% identity; Table 4). In these comparisons, clusters of identity extended over the length of the alignment, but were concentrated in the amino-terminal region. The amino acid sequence of the Bacteroides Tc$^r$ protein had no significant similarity to those of sequenced Tc$^r$ genes belonging either to the efflux or to the tetracycline detoxification classes of resistance. The results of these comparisons indicated that the Bacteroides Tc$^r$ gene was likely to be a member of the ribosome protection class of Tc$^r$, but was clearly in a different hybridization class from TeTm and TetO. Accordingly, we have designated this new class TetQ.

A hydrophobicity plot generated from the deduced amino acid sequence of TetQ was very similar to those generated for TetM and TetO. Since TeTm and TetO are thought to be soluble proteins that function in the cytoplasm [Burdett, *J. bacteriol.*, 165:564–569 (1986); Manavathu, et al., *Antimicrob. Agents Chemother.*, 34:71–77 (1990)], this suggests that TetQ is also a soluble protein. However, TetQ contained a relatively hydrophobic internal region (residues 205–247) that was not extant in Term or TetO. This could explain why a portion of the Bacteroides Tc$^r$ protein fractionated with the membrane in maxicell separations.

7. Upstream region of tetO

The DNA sequence of the upstream region of tetQ is shown in FIG. 7. An *E. coli*-like promoter sequence was found immediately upstream of the start of the open reading frame. The deletions in pNFD13-2Δ1 through pNFD13-2Δ3, which did not affect the tetracycline MIC in *E. coli*, left this promoter sequence intact. pNFD13-2Δ4, in which the −35 region of this promoter was deleted, reduced the MIC in *E. coli*. pNFD13-2Δ5, in which both the −35 and the −10 region of this promoter were deleted, abolished resistance in *E. coli*. Thus, the *E. coli*-like −10 and −35 regions probably constitute the promoter that is driving transcription in *E. coli*.

Interestingly, this region was not sufficient for expression in Bacteroides, as evidenced by the observation that pNFD13-2Δ3 did not confer resistance on Bacteroides. The largest deletion that was still active in Bacteroides (pNFD13-2Δ2) contained the *E. coli* promoter plus about an additional 150 bp. The sequence of the smallest promoter region identified as functional in Bacteroides species is presented in Chart C below.

The upstream regions of tetM and tetO genes showed remarkable sequence similarity. This region contained the putative Gram-positive ribosome binding site [Martin, et al., *Nucl. Acids Res.*, 14:7047–7058 (1986)]. A comparison of the upstream region of tetM/O to that of tetQ disclosed no detectable similarity. (See FIG. 6) The tetQ upstream region also lacked a distinguishable ribosome binding site.

8. Relatedness to Tc$^r$ of pRRI4

Plasmid pNFD13-2 labeled with p$^{32}$ was used as a probe to hybridize to pRRI4 digested with EcoRI, PvuII, HincII-EcoRV and NciI. Plasmid pRRI4 in *P. ruminicola* 223/M2/7 was obtained from Dr. Harry J. Flint, Rowett Research Institute, Bucksbum, Aberdeen, U.K. It was extracted from *P. ruminicola* 223/M2/7 by standard techniques [Maniatis, et al., supra]. A cross-hybridizing region was identified. To ascertain if this cross-hybridizing region contained the Tc$^r$ gene, a 5 kbp HincII-PvuII segment which covers this region was cloned into pFD160 and mobilized from *E. coli* into *B. uniformis*. The resulting transconjugants were Tc$^r$. Other hybridization experiments also indicated that the Tc$^r$ gene on pRRI4 was at least 80% homologous to the Tc$^r$ genes on pNFD13-2 and other Bacteroides Tc$^r$Em$^r$ elements.

Recently, sequencing of the Tc$^r$ gene on pRRI4 has been completed. Its sequence has been found to be 97% identical to that of the Tc$^r$ gene on pNFD13-2. Accordingly, it is in the TetQ class.

C. Discussion

By size and amino acid sequence similarity, the Bacteroides TetQ appeared to be a ribosome protection type of tetracycline resistance. However, TetQ clearly did not belong in either class TetM or class TetO because the amino acid identity with those classes is only 40.3–40.9%.

All Tc$^r$ Bacteroides strains that we screened had DNA which hybridized to an internal fragment of the cloned Tc$^r$ gene under conditions of high stringency. Thus, TetQ is probably the predominant Tc$^r$ among the colonic Bacteroides. In fact, recent evidence indicates that Tc$^r$ determinants from colonic and oral Bacteroides have high similarity [Guiney and Bouic, *J. Bacteriol.*, 172:495–497 (1990)]. This suggests that TetQ may be ubiquitous in the genus Bacteroides. Also, at least one *P. ruminicola* Tc$^r$ gene is of the TetQ class.

Previously sequenced ribosome protection Tc$^r$ genes were remarkable for their sequence similarity (Table 4). For instance, the TetO found in *Campylobacter jejuni* shared 98.1% intraclass amino acid identity with the TetO found in *Streptococcus mutans*. The *C. jejuni* TetO shared 75.1–76.8% interclass amino acid identity with the TetM's found in Staphylococcus, Streptococcus, and Ureaplasma. Genes that are similar enough to cross-hybridize with tetM and tetO on Southern blots have been found in Clostridium, Eikenella, Fusobacterium, Gardnerella, Hemophilus, Kingella, Mycoplasma, Neisseria, and Veillonella [Salyers, et al., *Mol. Microbiol.*, 4:151–156 (1989)].

The amino-terminal regions of TetM and TetO have high amino acid similarity to the amino-terminal region of the elongation factors [Sanchez-Pescador, et al., *Nucl. Acids Res.*, 16, 1218 (1988); Manavathu et al., *Antimicrob. Agents Chemother.*, 34:71–77 (1990)]. This region is responsible for guanosine nucleotide binding by one elongation factor (EF-Tu) [Jacquet and Parmeggiani, *The EMBO J.*, 7:2861–2867 (1988); Jurnak, *Science*, 230:32–36 (1985)], and is conserved in GTP-binding proteins [Halliday, *J. Nucleotide Prot. Phosphoryl. Res.*, 9:435–448 (1984)]. Though TetQ is the most diverged ribosome protection Tc$^r$, it maintains high amino acid conservation in this GDP/GTP-binding domain. (See FIG. 6) This indicates that this functional domain my be involved directly in the ribosome protection resistance mechanism. Manavathu, et al., *Antimicrob. Agents Chemother.*, 34:71–77 (1990), suggested that TetO by have the potential to bind GTP, but no such binding has yet been demonstrated.

The upstream regions of tetM and tetO genes, which are virtually identical, contain a Gram-positive ribosome binding site. The mol % G+C of tetQ (40.1%) is similar to that of tetM and tetO, but is also similar the mol % G+C of chromosomal DNA from colonic Bacteroides [39–46%; Johnson, *J. Syst. Bacteriol.*, 28:245–256 (1978)]. By contrast, the upstream region of tetQ is completely different from that of tetM and tetO.

TABLE 2

Strains Used In Connection with Sequencing Of Tc$^r$

| Strain or Plasmid | Relevant Phenotype |
|---|---|
| *E. coli* strains | |
| DH5α | RecA Δ (argF-lacA) U169 ø80d1acΔM15 |
| LCD44 | RecA MetE Tc$^s$ derivative of RK5173. |
| Bacteroides strains | |
| *B. thetaoitaomicron* | |
| 5482 | |
| BT4001 | Tc$^s$ Em$^s$; Spontaneous Rif$^r$ derivative of *B. thetaiotaomicron* 5482 |
| BT4002 | Tc$^r$ |
| BT4004 | Tc$^r$ |
| BT4007 | Tc$^r$ Em$^r$ |
| BT4008 | Tc$^r$ Em$^r$ |
| 2808 | Tc$^r$ |
| *B. uniformis* | |
| BU1001 | Tc$^s$; Rif$^r$ derivative of *B. uniformis* 0061 |
| C7–17 | Tc$^r$ |
| 3537 | Tc$^r$ |
| T1–1 | Tc$^r$ |
| *B. distasonas* | |
| 4243 | Tc$^s$ |
| C30–45 | Tc$^r$ |
| 6308 | Tc$^r$ |
| *B. caccae* | |
| 3452A | Tc$^s$ |
| 8608 | Tc$^r$ |
| *B. fragilis* | |
| AK87 | Tc$^r$ |

*Resistance phenotype expressed in *E. coli* is indicated in parenthesis.

TABLE 3

GenBank Access Codes For Sequences

| Source organism | Gene product | GenBank LOCUS | GenBank Access. |
|---|---|---|---|
| *Staphylococcus aureus* | TetM | Statetm | M21136 |
| *Streptococcus faecalis* | TetM | Str1545tr | X04388 |

TABLE 3-continued

GenBank Access Codes For Sequences

| Source organism | Gene product | GenBank LOCUS | GenBank Access. |
|---|---|---|---|
| *Ureaplasma urealyticum* | TetM | X06901 | X06901 |
| *Campylobacter jejuni* | TetO | Cajtrccra | M18896 |
| *Streptococcus mutans* | TetO | Stateosm | M20925 |
| *Escherichia coli* | EF-Tu | Ecotgtufb | J01717 |
| | EF-G | Ecostra | X00415 |
| *Micrococcus luteus* | EF-Tu | M17788 | M17788 |
| | EF-G | M17788 | M17788 |
| *Spirulina platensis* | EF-Tu | X15646 | X15646 |
| | EF-G | X15646 | X15646 |
| *Thermos thermorphilus* | EF-Tu | Tthtuf1 | X05977 |
| | EF-G | X16278 | X16278 |
| *Thermotoga maritima* | EF-Tu | Tmoeftu | M27479 |
| *Euglena gracilis* chloroplast | EF-Tu | Egrcpeftu | X00044 |
| *Methanococcus vannielii* | EF-1 | Mvatuf | X05698 |
| | EF-2 | Mvafus | X12384 |
| *Saccharomyces cerevisiae* | EF-1α | Yscefla | X00779 |
| *Mucor racemonsus* | EF-1α | Mratefla | J02605 |
| *Dictyostelium discoideum* | EF-2 | Ddief2 | M26017 |
| *Drosophila melanogaster* | EF-2 | X15805 | X15805 |
| *Xenopus laevis* | EF-1α | Xeleflal | M25697 |
| *Mesocricetus sp.* | EF-2 | Hamef2 | M13708 |
| *Mus musculus* | EF-1α | M22432 | M22432 |
| *Rattus norvegicus* | EF-2 | Ratef2r | Y07504 |
| *Homo sapiens* | EF-1α | Humefla | X03558 |
| | EF-2 | Humef2ab | M30456 |

TABLE 4

Percent amino acid similarity and percent amino acid identity between deduced peptide sequences of ribosome protection tetracycline resistance genes

| | percent similarity | | | | | |
|---|---|---|---|---|---|---|
| | 1 | 2 | 3 | 4 | 5 | 6 |
| 1. *S. aureus* TetM | — | 95.3 | 98.1 | 85.3 | 85.9 | 62.5 |
| 2. *S. pneumoniae* TetM | 92.2 | — | 96.7 | 85.7 | 86.1 | 61.1 |
| 3. *U. urealyticum* TetM | 96.6 | 95.0 | — | 85.7 | 86.3 | 62.5 |
| 4. *C. jejuni* TetO | 75.1 | 76.8 | 76.0 | — | 98.4 | 60.5 |
| 5. *S. mutans* TetO | 75.6 | 76.9 | 76.4 | 98.1 | — | 60.8 |
| 6. *B. thetaiotaomicron* TetQ | 41.2 | 41.0 | 41.2 | 41.0 | 41.0 | — | percent identity

Chart A

```
GAGCTCTAAA TTTAAATATA AACAACGAAT TATCTCCTTA ACGTACGTTT    50

TCGTTCCATT GGCCCTCAAA CCCCGTTATA TACATTCATG TCCATTTATG    100
```

-continued

```
TAAAAAATCC TGCTGACCTT GTTTATGTCT TGTCAGTCAC CATTTGCAAA        150

ACCATATTTG ACCCTCAAAG AGGCTGAATT TGATAAGCAA CTTGCTACAT        200

ACTCATAATA AGGAGCTAAA TAGAACACGA ATGGGAAATA CTCAAATGCC        250

AAACTAAAGA AGATATTGGC CAAAATAAAC GCTATACCGA GAGAGAAACT        300

TGATTTTTCA ACTTCCTAAA ACAGTGTTGT TCAAACATTT CTACTTATTT        350

GTACTTACCA GTTGAACCTA CGTTTCCCTA ATAAAATGTC TATGGTAAAA        400

AGTTAAAAAA TCCTCCTACT TTTGTTAGAT ATATTTTTTT GTGTAATTTT        450

GTAATCGTTA TGCGGCAGTA ATAATATACA TATTAATACG AGTTATTAAT        500

CCTGTAGTTC TCATATGCTA CGAGGAGGTA TTAAAAGGTG CGTTTCGACA        550

ATGCATCTAT TGTAGTATAT TATTGCTTAA TCCAA ATG AAT ATT ATA        597
                                       Met Asn Ile Ile

AAT TTA GGA ATT CTT GCT CAC ATT GAT GCA GGA AAA ACT TCC        639
Asn Leu Gly Ile Leu Ala His Ile Asp Ala Gly Lys Thr Ser
 5                   10                  15

GTA ACC GAG AAT CTG CTG TTT GCC AGT GGA GCA ACG GAA AAG        681
Val Thr Glu Asn Leu Leu Phe Ala Ser Gly Ala Thr Glu Lys
     20                  25                  30

TGC GGC TGT GTG GAT AAT GGT GAC ACC ATA ACG GAC TCT ATG        723
Cys Gly Cys Val Asp Asn Gly Asp Thr Ile Thr Asp Ser Met
         35                  40                  45

GAT ATA GAG AAA CGT AGA GGA ATT ACT GTT CGG GCT TCT ACG        765
Asp Ile Glu Lys Arg Arg Gly Ile Thr Val Arg Ala Ser Thr
             50                  55                  60

ACA TCT ATT ATC TGG AAT GGT GTG AAA TGC AAT ATC ATT GAC        807
Thr Ser Ile Ile Trp Asn Gly Val Lys Cys Asn Ile Ile Asp
                 65                  70

ACT CCG GGA CAC ATG GAT TTT ATT GCG GAA GTG GAG CGG ACA        849
Thr Pro Gly His Met Asp Phe Ile Ala Glu Val Glu Arg Thr
75                  80                  85

TTC AAA ATG CTT GAT GGA GCA GTC CTC ATC TTA TCC GCA AAG        891
Phe Lys Met Leu Asp Gly Ala Val Leu Ile Leu Ser Ala Lys
     90                  95                  100

GAA GGC ATA CAA GCG CAG ACA AAG TTG CTG TTC AAT ACT TTA        933
Glu Gly Ile Gln Ala Gln Thr Lys Leu Leu Phe Asn Thr Leu
         105                 110                 115

CAG AAG CTG CAA ATC CCG ACA ATT ATA TTT ATC AAT AAG ATT        975
Gln Lys Leu Gln Ile Pro Thr Ile Ile Phe Ile Asn Lys Ile
             120                 125                 130

GAC CGA GCC GGT GTG AAT TTG GAG CGT TTG TAT CTG GAT ATA        1017
Asp Arg Ala Gly Val Asn Leu Glu Arg Leu Tyr Leu Asp Ile
                 135                 140

AAA GCA AAT CTG TCT CAA GAT GTC CTG TTT ATG CAA AAT GTT        1059
Lys Ala Asn Leu Ser Gln Asp Val Leu Phe Met Gln Asn Val
145                 150                 155

GTC GAT GGA TCG GTT TAT CCG GTT TGC TCC CAA ACA TAT ATA        1101
Val Asp Gly Ser Val Tyr Pro Val Cys Ser Gln Thr Tyr Ile
     160                 165                 170

AAG GAA GAA TAC AAA GAA TTT GTA TGC AAC CAT GAC GAC AAT        1143
Lys Glu Glu Tyr Lys Glu Phe Val Cys Asn His Asp Asp Asn
         175                 180                 185
```

```
ATA TTA GAA CGA TAT TTG GCG GAT AGC GAA ATT TCA CCG GCT      1185
Ile Leu Glu Arg Tyr Leu Ala Asp Ser Glu Ile Ser Pro Ala
        190                 195                     200

GAT TAT TGG AAT ACG ATA ATC GCT CTT GTG GCA AAA GCC AAA      1227
Asp Tyr Trp Asn Thr Ile Ile Ala Leu Val Ala Lys Ala Lys
                205                 210

GTC TAT CCG GTG CTA CAT GGA TCA GCA ATG TTC AAT ATC GGT      1269
Val Tyr Pro Val Leu His Gly Ser Ala Met Phe Asn Ile Gly
215                     220                 225

ATC AAT GAG TTG TTG GAC GCC ATC ACT TCT TTT ATA CTT CCT      1311
Ile Asn Glu Leu Leu Asp Ala Ile Thr Ser Phe Ile Leu Pro
        230                 235                 240

CCG GCA TCG GTC TCA AAC AGA CTT TCA TCT TAT CTT TAT AAG      1353
Pro Ala Ser Val Ser Asn Arg Leu Ser Ser Tyr Leu Tyr Lys
            245                 250                 255

ATA GAG CAT GAC CCC AAA GGA CAT AAA AGA AGT TTT CTA AAA      1395
Ile Glu His Asp Pro Lys Gly His Lys Arg Ser Phe Leu Lys
                260                 265                 270

ATA ATT GAC GGA AGT CTG AGA CTT CGA GAC GTT GTA AGA ATC      1437
Ile Ile Asp Gly Ser Leu Arg Leu Arg Asp Val Val Arg Ile
                275                 280

AAC GAT TCG GAA AAA TTC ATC AAG ATT AAA AAT CTA AAA ACT      1479
Asn Asp Ser Glu Lys Phe Ile Lys Ile Lys Asn Leu Lys Thr
285                 290                 295

ATC AAT CAG GGC AGA GAG ATA AAT GTT GAT GAA GTG GGC GCC      1521
Ile Asn Gln Gly Arg Glu Ile Asn Val Asp Glu Val Gly Ala
        300                 305                 310

AAT GAT ATC GCG ATT GTA GAG GAT ATG GAT GAT TTT CGA ATC      1563
Asn Asp Ile Ala Ile Val Glu Asp Met Asp Asp Phe Arg Ile
            315                 320                 325

GGA AAT TAT TTA GGT GCT GAA CCT TGT TTG ATT CAA GGA TTA      1605
Gly Asn Tyr Leu Gly Ala Glu Pro Cys Leu Ile Gln Gly Leu
                330                 335                 340

TCG CAT CAG CAT CCC GCT CTC AAA TCC TCC GTC CGG CCA GAC      1647
Ser His Gln His Pro Ala Leu Lys Ser Ser Val Arg Pro Asp
                    345                 350

AGG CCC GAA GAG AGA AGC AAG GTG ATA TCC GCT CTG AAT ACA      1689
Arg Pro Glu Glu Arg Ser Lys Val Ile Ser Ala Leu Asn Thr
355                 360                 365

TTG TGG ATT GAA GAC CCG TCT TTG TCC TTT TCC ATA AAC TCA      1731
Leu Trp Ile Glu Asp Pro Ser Leu Ser Phe Ser Ile Asn Ser
    370                 375                 380

TAT AGT GAT GAA TTG GAA ATC TCG TTA TAT GGT TTA ACC CAA      1773
Tyr Ser Asp Glu Leu Glu Ile Ser Leu Tyr Gly Leu Thr Gln
        385                 390                 395

AAG GAA ATC ATA CAG ACA TTG CTG GAA GAA CGA TTT TCC GTA      1815
Lys Glu Ile Ile Gln Thr Leu Leu Glu Glu Arg Phe Ser Val
            400                 405                 410

AAG GTC CAT TTT GAT GAG ATC AAG ACT ATA TAC AAA GAA GGA      1857
Lys Val His Phe Asp Glu Ile Lys Thr Ile Tyr Lys Glu Arg
                415                 420

CCT GTA AAA AAG GTC AAT AAG ATT TAA CAG ATC GAA GTG CCG      1899
Pro Val Lys Lys Val Asn Lys Ile Ile Gln Ile Glu Val Pro
425                 430                 435

CCC AAC CCT TAT TGG GCC ACA ATA GGG CTG ACT CTT GAT CCC      1941
Pro Asn Pro Tyr Trp Ala Thr Ile Gly Leu Thr Leu Asp Pro
    440                 445                 450

TTA CCG TTA GGG ACA GGG TTG CAA ATC GAA AGT GAC ATC TCC      1983
Leu Pro Leu Gly Thr Gly Leu Gln Ile Glu Ser Asp Ile Ser
        455                 460                 465

TAT GGT TAT CTG AAC CAT TCT TTT CAA AAT GCC GTT TTT GAA      2025
Tyr Gly Tyr Leu Asn His Ser Phe Gln Asn Ala Val Phe Glu
            470                 475                 480
```

```
GGG ATT CGT ATG TCT TGC CAA TCC GGG TTA CAT GGA TGG GAA              2067
Gly Ile Arg Met Ser Cys Gln Ser Gly Leu His Gly Trp Glu
            485                     490

GTG ACT GAT CTG AAA GTA ACT TTT ACT CAA GCC GAG TAT TAT              2109
Val Thr Asp Leu Lys Val Thr Phe Thr Gln Ala Glu Tyr Tyr
495                 500                 505

AGC CCG GTA AGT ACA CCT GCT GAT TTC AGA CAG CTG ACC CCT              2151
Ser Pro Val Ser Thr Pro Ala Asp Phe Arg Gln Leu Thr Pro
    510                 515                 520

TAT GTC TTC AGG CTG GCC TTG CAA CAG TCA GGT GTG GAC ATT              2193
Tyr Val Phe Arg Leu Ala Leu Gln Gln Ser Gly Val Asp Ile
        525                 530                 535

CTC GAA CCG ATG CTC TAT TTT GAG TTG CAG ATA CCC CAA GCG              2235
Leu Glu Pro Met Leu Tyr Phe Glu Leu Gln Ile Pro Gln Ala
            540                 545                 550

GCA AGT TCC AAA GCT ATT ACA GAT TTG CAA AAA ATG ATG TCT              2277
Ala Ser Ser Lys Ala Ile Thr Asp Leu Gln Lys Met Met Ser
                555                 560

GAG ATT GAA GAC ATC AGT TGC AAT AAT GAG TGG TGT CAT ATT              2319
Glu Ile Glu Asp Ile Ser Cys Asn Asn Glu Trp Cys His Ile
565                 570                 575

AAA GGG AAA GTT CCA TTA AAT ACA AGT AAA GAC TAT GCA TCA              2361
Lys Gly Lys Val Pro Leu Asn Thr Ser Lys Asp Tyr Ala Ser
    580                 585                 590

GAA GTA AGT TCA TAC ACT AAG GGC TTA GGC ATT TTT ATG GTT              2403
Glu Val Ser Ser Tyr Thr Lys Gly Leu Gly Ile Phe Met Val
        595                 600                 605

AAG CCA TGC GGG TAT CAA ATA ACA AAA GGC GGT TAT TCT GAT              2445
Lys Pro Cys Gly Tyr Gln Ile Thr Lys Gly Gly Tyr Ser Asp
            610                 615                 620

AAT ATC CGC ATG AAC GAA AAA GAT AAA CTT TTA TTC ATG TTC              2487
Asn Ile Arg Met Asn Glu Lys Asp Lys Leu Leu Phe Met Phe
                625                 630

CAA AAA TCA ATG TCA TCA AAA TAATGGAGCG GTCAGGAAAT                    2528
Gln Lys Ser Met Ser Ser Lys
635                 640

TTCTATAAGG CAATACAGTT GGGATATATA CTTATCTCCA TTCTTATCGG               2578

ATGTATGGCA TATAATAGCC TCTATGAATG GCAGGAGATA GAAGCATTAG               2628

AACTTGGCAA TAAAAAAATA GACGAGCTC                                      2657
                                    [seq id no 2]
```

Chart B

```
Met Asn Ile Ile Asn Leu Gly Ile Leu Ala His Ile Asp Ala Gly
                5                   10                  15

Lys Thr Ser Val Thr Glu Asn Leu Leu Phe Ala Ser Gly Ala Thr
                20                  25                  30

Glu Lys Cys Gly Cys Val Asp Asn Gly Asp Thr Ile Thr Asp Ser
                35                  40                  45

Met Asp Ile Glu Lys Arg Arg Gly Ile Thr Val Arg Ala Ser Thr
                50                  55                  60

Thr Ser Ile Ile Trp Asn Gly Val Lys Cys Asn Ile Ile Asp Thr
                65                  70                  75

Pro Gly His Met Asp Phe Ile Ala Glu Val Glu Arg Thr Phe Lys
                80                  85                  90

Met Leu Asp Gly Ala Val Leu Ile Leu Ser Ala Lys Glu Gly Ile
                95                  100                 105
```

-continued

| | | | | | | | | | | | |
|---|---|---|---|---|---|---|---|---|---|---|---|
| Gln | Ala | Gln | Thr | Lys 110 | Leu | Leu | Phe | Asn | Thr 115 | Leu | Gln | Lys | Leu | Gln 120 |
| Ile | Pro | Thr | Ile | Ile 125 | Phe | Ile | Asn | Lys | Ile 130 | Asp | Arg | Ala | Gly | Val 135 |
| Asn | Leu | Glu | Arg | Leu 140 | Tyr | Leu | Asp | Ile | Lys 145 | Ala | Asn | Leu | Ser | Gln 150 |
| Asp | Val | Leu | Phe | Met 155 | Gln | Asn | Val | Val | Asp 160 | Gly | Ser | Val | Tyr | Pro 165 |
| Val | Cys | Ser | Gln | Thr 170 | Tyr | Ile | Lys | Glu | Glu 175 | Tyr | Lys | Glu | Phe | Val 180 |
| Cys | Asn | His | Asp | Asp 185 | Asn | Ile | Leu | Glu | Arg 190 | Tyr | Leu | Ala | Asp | Ser 195 |
| Glu | Ile | Ser | Pro | Ala 200 | Asp | Tyr | Trp | Asn | Thr 205 | Ile | Ile | Ala | Leu | Val 210 |
| Ala | Lys | Ala | Lys | Val 215 | Tyr | Pro | Val | Leu | His 220 | Gly | Ser | Ala | Met | Phe 225 |
| Asn | Ile | Gly | Ile | Asn 230 | Glu | Leu | Leu | Asp | Ala 235 | Ile | Thr | Ser | Phe | Ile 240 |
| Leu | Pro | Pro | Ala | Ser 245 | Val | Ser | Asn | Arg | Leu 250 | Ser | Ser | Tyr | Leu | Tyr 255 |
| Lys | Ile | Glu | His | Asp 260 | Pro | Lys | Gly | His | Lys 265 | Arg | Ser | Phe | Leu | Lys 270 |
| Ile | Ile | Asp | Gly | Ser 275 | Leu | Arg | Leu | Arg | Asp 280 | Val | Val | Arg | Ile | Asn 285 |
| Asp | Ser | Glu | Lys | Phe 290 | Ile | Lys | Ile | Lys | Asn 295 | Leu | Lys | Thr | Ile | Asn 300 |
| Gln | Gly | Arg | Glu | Ile 305 | Asn | Val | Asp | Glu | Val 310 | Gly | Ala | Asn | Asp | Ile 315 |
| Ala | Ile | Val | Glu | Asp 320 | Met | Asp | Asp | Phe | Arg 325 | Ile | Gly | Asn | Tyr | Leu 330 |
| Gly | Ala | Glu | Pro | Cys 335 | Leu | Ile | Gln | Gly | Leu 340 | Ser | His | Gln | His | Pro 345 |
| Ala | Leu | Lys | Ser | Ser 350 | Val | Arg | Pro | Asp | Arg 355 | Pro | Glu | Glu | Arg | Ser 360 |
| Lys | Val | Ile | Ser | Ala 365 | Leu | Asn | Thr | Leu | Trp 370 | Ile | Glu | Asp | Pro | Ser 375 |
| Leu | Ser | Phe | Ser | Ile 380 | Asn | Ser | Tyr | Ser | Asp 385 | Glu | Leu | Glu | Ile | Ser 390 |
| Leu | Tyr | Gly | Leu | Thr 395 | Gln | Lys | Glu | Ile | Ile 400 | Gln | Thr | Leu | Leu | Glu 405 |
| Glu | Arg | Phe | Ser | Val 410 | Lys | Val | His | Phe | Asp 415 | Glu | Ile | Lys | Thr | Ile 420 |
| Tyr | Lys | Glu | Arg | Pro 425 | Val | Lys | Lys | Val | Asn 430 | Lys | Ile | Ile | Gln | Ile 435 |
| Glu | Val | Pro | Pro | Asn 440 | Pro | Tyr | Trp | Ala | Thr 445 | Ile | Gly | Leu | Thr | Leu 450 |
| Glu | Pro | Leu | Pro | Leu 455 | Gly | Thr | Gly | Leu | Gln 460 | Ile | Glu | Ser | Asp | Ile 465 |
| Ser | Tyr | Gly | Tyr | Leu 470 | Asn | His | Ser | Phe | Gln 475 | Asn | Ala | Val | Phe | Glu 480 |
| Gly | Ile | Arg | Met | Ser 485 | Cys | Gln | Ser | Gly | Leu 490 | His | Gly | Trp | Glu | Val 495 |
| Thr | Asp | Leu | Lys | Val 500 | Thr | Phe | Thr | Gln | Ala 505 | Glu | Tyr | Tyr | Ser | Pro 510 |
| Val | Ser | Tyr | Pro | Ala 515 | Asp | Phe | Arg | Gln | Leu 520 | Thr | Pro | Tyr | Val | Phe 525 |

-continued

| | | | | | | | | | | | | |
|---|---|---|---|---|---|---|---|---|---|---|---|---|
|Arg|Leu|Ala|Leu|Gln 530|Gln|Ser|Gly|Val|Asp 535|Ile|Leu|Glu|Pro|Met 540|
|Leu|Tyr|Phe|Glu|Leu 545|Gln|Ile|Pro|Gln|Ala 550|Ala|Ser|Ser|Lys|Ala 555|
|Ile|Thr|Asp|Leu|Gln 560|Lys|Met|Met|Ser|Glu 565|Ile|Glu|Asp|Ile|Ser 570|
|Cys|Asn|Asn|Glu|Trp 575|Cys|His|Ile|Lys|Gly 580|Lys|Val|Pro|Leu|Asn 585|
|Thr|Ser|Lys|Asp|Tyr 590|Ala|Ser|Glu|Val|Ser 595|Ser|Tyr|Thr|Lys|Gly 600|
|Leu|Gly|Ile|Phe|Met 605|Val|Lys|Pro|Cys|Gly 610|Tyr|Gln|Ile|Thr|Lys 615|
|Gly|Gly|Tyr|Ser|Asp 620|Asn|Ile|Arg|Met|Asn 625|Glu|Lys|Asp|Lys|Leu 630|
|Leu|Phe|Met|Phe|Gln 635|Lys|Ser|Met|Ser|Ser 640|Lys| | | | |

[seq id no 3]

Chart C

```
AAAAATCCTC CTACTTTTGT TAGATATATT TTTTTGTGTA ATTTTGTAAT        50

CGTTATGCGG CAGTAATAAT ATACATATTA ATACGAGTTA TTAATCCTGT       100

AGTTCTCATA TGCTACGAGG AGGTATTAAA AGGTGCGTTT CGACAATGCA       150

TCTATTGTAG TATATTATTG CTTAATCCAA,                            180
```
[seq id no 1]

---

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 180 base pairs
        ( B ) TYPE: nucleic acid
        ( C ) STRANDEDNESS: double stranded
        ( D ) TOPOLOGY: circular ( x i ) SEQUENCE DESCRIPTION: SEQ ID NO:1:

```
AAAAATCCTC CTACTTTTGT TAGATATATT TTTTTGTGTA ATTTTGTAAT        50

CGTTATGCGG CAGTAATAAT ATACATATTA ATACGAGTTA TTAATCCTGT       100

AGTTCTCATA TGCTACGAGG AGGTATTAAA AGGTGCGTTT CGACAATGCA       150

TCTATTGTAG TATATTATTG CTTAATCCAA                             180
```

( 2 ) INFORMATION FOR SEQ ID NO:2:

( i ) SEQUENCE CHARACTERISTICS:
        ( A ) LENGTH: 2657 base pairs
        ( B ) TYPE: nucleic acid
        ( C ) STRANDEDNESS: double stranded
        ( D ) TOPOLOGY: circular ( x i ) SEQUENCE DESCRIPTION: SEQ ID NO:2:

```
GAGCTCTAAA TTTAAATATA AACAACGAAT TATCTCCTTA ACGTACGTTT        50
```

-continued

```
TCGTTCCATT GGCCCTCAAA CCCCGTTATA TACATTCATG TCCATTTATG      100

TAAAAAATCC TGCTGACCTT GTTTATGTCT TGTCAGTCAC CATTTGCAAA      150

ACCATATTTG ACCCTCAAAG AGGCTGAATT TGATAAGCAA CTTGCTACAT      200

ACTCATAATA AGGAGCTAAA TAGAACACGA ATGGGAAATA CTCAAATGCC      250

AAACTAAAGA AGATATTGGC CAAAATAAAC GCTATACCGA GAGAGAAACT      300

TGATTTTTCA ACTTCCTAAA ACAGTGTTGT TCAAACATTT CTACTTATTT      350

GTACTTACCA GTTGAACCTA CGTTTCCCTA ATAAATGTC  TATGGTAAAA      400

AGTTAAAAAA TCCTCCTACT TTTGTTAGAT ATATTTTTTT GTGTAATTTT      450

GTAATCGTTA TGCGGCAGTA ATAATATACA TATTAATACG AGTTATTAAT      500

CCTGTAGTTC TCATATGCTA CGAGGAGGTA TTAAAAGGTG CGTTTCGACA      550

ATGCATCTAT TGTAGTATAT TATTGCTTAA TCCAA ATG AAT ATT ATA      597
                                       Met Asn Ile Ile

AAT TTA GGA ATT CTT GCT CAC ATT GAT GCA GGA AAA ACT TCC     639
Asn Leu Gly Ile Leu Ala His Ile Asp Ala Gly Lys Thr Ser
 5              10                  15

GTA ACC GAG AAT CTG CTG TTT GCC AGT GGA GCA ACG GAA AAG     681
Val Thr Glu Asn Leu Leu Phe Ala Ser Gly Ala Thr Glu Lys
 20              25                  30

TGC GGC TGT GTG GAT AAT GGT GAC ACC ATA ACG GAC TCT ATG     723
Cys Gly Cys Val Asp Asn Gly Asp Thr Ile Thr Asp Ser Met
         35              40                  45

GAT ATA GAG AAA CGT AGA GGA ATT ACT GTT CGG GCT TCT ACG     765
Asp Ile Glu Lys Arg Arg Gly Ile Thr Val Arg Ala Ser Thr
             50                  55                  60

ACA TCT ATT ATC TGG AAT GGT GTG AAA TGC AAT ATC ATT GAC     807
Thr Ser Ile Ile Trp Asn Gly Val Lys Cys Asn Ile Ile Asp
                 65                  70

ACT CCG GGA CAC ATG GAT TTT ATT GCG GAA GTG GAG CGG ACA     849
Thr Pro Gly His Met Asp Phe Ile Ala Glu Val Glu Arg Thr
 75              80                  85

TTC AAA ATG CTT GAT GGA GCA GTC CTC ATC TTA TCC GCA AAG     891
Phe Lys Met Leu Asp Gly Ala Val Leu Ile Leu Ser Ala Lys
 90              95                  100

GAA GGC ATA CAA GCG CAG ACA AAG TTG CTG TTC AAT ACT TTA     933
Glu Gly Ile Gln Ala Gln Thr Lys Leu Leu Phe Asn Thr Leu
         105             110                 115

CAG AAG CTG CAA ATC CCG ACA ATT ATA TTT ATC AAT AAG ATT     975
Gln Lys Leu Gln Ile Pro Thr Ile Ile Phe Ile Asn Lys Ile
             120                 125                 130

GAC CGA GCC GGT GTG AAT TTG GAG CGT TTG TAT CTG GAT ATA    1017
Asp Arg Ala Gly Val Asn Leu Glu Arg Leu Tyr Leu Asp Ile
                 135                 140

AAA GCA AAT CTG TCT CAA GAT GTC CTG TTT ATG CAA AAT GTT    1059
Lys Ala Asn Leu Ser Gln Asp Val Leu Phe Met Gln Asn Val
 145             150                 155

GTC GAT GGA TCG GTT TAT CCG GTT TGC TCC CAA ACA TAT ATA    1101
Val Asp Gly Ser Val Tyr Pro Val Cys Ser Gln Thr Tyr Ile
 160             165                 170

AAG GAA GAA TAC AAA GAA TTT GTA TGC AAC CAT GAC GAC AAT    1143
Lys Glu Glu Tyr Lys Glu Phe Val Cys Asn His Asp Asp Asn
         175             180                 185

ATA TTA GAA CGA TAT TTG GCG GAT AGC GAA ATT TCA CCG GCT    1185
Ile Leu Glu Arg Tyr Leu Ala Asp Ser Glu Ile Ser Pro Ala
             190                 195                 200

GAT TAT TGG AAT ACG ATA ATC GCT CTT GTG GCA AAA GCC AAA    1227
```

-continued

|  |  |  |  |  |  |  |  |  |  |  |  |  |  |  |
|---|---|---|---|---|---|---|---|---|---|---|---|---|---|---|
| Asp | Tyr | Trp | Asn | Thr 205 | Ile | Ile | Ala | Leu | Val 210 | Ala | Lys | Ala | Lys |  |

| GTC | TAT | CCG | GTG | CTA | CAT | GGA | TCA | GCA | ATG | TTC | AAT | ATC | GGT | 1269 |
|---|---|---|---|---|---|---|---|---|---|---|---|---|---|---|
| Val 215 | Tyr | Pro | Val | Leu 220 | His | Gly | Ser | Ala | Met 225 | Phe | Asn | Ile | Gly |  |

| ATC | AAT | GAG | TTG | TTG | GAC | GCC | ATC | ACT | TCT | TTT | ATA | CTT | CCT | 1311 |
|---|---|---|---|---|---|---|---|---|---|---|---|---|---|---|
| Ile | Asn 230 | Glu | Leu | Leu | Asp | Ala 235 | Ile | Thr | Ser | Phe | Ile 240 | Leu | Pro |  |

| CCG | GCA | TCG | GTC | TCA | AAC | AGA | CTT | TCA | TCT | TAT | CTT | TAT | AAG | 1353 |
|---|---|---|---|---|---|---|---|---|---|---|---|---|---|---|
| Pro | Ala | Ser 245 | Val | Ser | Asn | Arg | Leu 250 | Ser | Ser | Tyr | Leu | Tyr 255 | Lys |  |

| ATA | GAG | CAT | GAC | CCC | AAA | GGA | CAT | AAA | AGA | AGT | TTT | CTA | AAA | 1395 |
|---|---|---|---|---|---|---|---|---|---|---|---|---|---|---|
| Ile | Glu | His | Asp 260 | Pro | Lys | Gly | His | Lys 265 | Arg | Ser | Phe | Leu | Lys 270 |  |

| ATA | ATT | GAC | GGA | AGT | CTG | AGA | CTT | CGA | GAC | GTT | GTA | AGA | ATC | 1437 |
|---|---|---|---|---|---|---|---|---|---|---|---|---|---|---|
| Ile | Ile | Asp | Gly | Ser 275 | Leu | Arg | Leu | Arg | Asp 280 | Val | Val | Arg | Ile |  |

| AAC | GAT | TCG | GAA | AAA | TTC | ATC | AAG | ATT | AAA | AAT | CTA | AAA | ACT | 1479 |
|---|---|---|---|---|---|---|---|---|---|---|---|---|---|---|
| Asn Asp 285 | Ser | Glu | Lys | Phe 290 | Ile | Lys | Ile | Lys | Asn 295 | Leu | Lys | Thr |  |  |

| ATC | AAT | CAG | GGC | AGA | GAG | ATA | AAT | GTT | GAT | GAA | GTG | GGC | GCC | 1521 |
|---|---|---|---|---|---|---|---|---|---|---|---|---|---|---|
| Ile | Asn | Gln 300 | Gly | Arg | Glu | Ile | Asn 305 | Val | Asp | Glu | Val | Gly 310 | Ala |  |

| AAT | GAT | ATC | GCG | ATT | GTA | GAG | GAT | ATG | GAT | GAT | TTT | CGA | ATC | 1563 |
|---|---|---|---|---|---|---|---|---|---|---|---|---|---|---|
| Asn | Asp | Ile | Ala 315 | Ile | Val | Glu | Asp | Met 320 | Asp | Asp | Phe | Arg | Ile 325 |  |

| GGA | AAT | TAT | TTA | GGT | GCT | GAA | CCT | TGT | TTG | ATT | CAA | GGA | TTA | 1605 |
|---|---|---|---|---|---|---|---|---|---|---|---|---|---|---|
| Gly | Asn | Tyr | Leu 330 | Gly | Ala | Glu | Pro | Cys 335 | Leu | Ile | Gln | Gly | Leu 340 |  |

| TCG | CAT | CAG | CAT | CCC | GCT | CTC | AAA | TCC | TCC | GTC | CGG | CCA | GAC | 1647 |
|---|---|---|---|---|---|---|---|---|---|---|---|---|---|---|
| Ser | His | Gln | His | Pro 345 | Ala | Leu | Lys | Ser | Ser 350 | Val | Arg | Pro | Asp |  |

| AGG | CCC | GAA | GAG | AGA | AGC | AAG | GTG | ATA | TCC | GCT | CTG | AAT | ACA | 1689 |
|---|---|---|---|---|---|---|---|---|---|---|---|---|---|---|
| Arg 355 | Pro | Glu | Glu | Arg | Ser 360 | Lys | Val | Ile | Ser | Ala 365 | Leu | Asn | Thr |  |

| TTG | TGG | ATT | GAA | GAC | CCG | TCT | TTG | TCC | TTT | TCC | ATA | AAC | TCA | 1731 |
|---|---|---|---|---|---|---|---|---|---|---|---|---|---|---|
| Leu | Trp 370 | Ile | Glu | Asp | Pro | Ser 375 | Leu | Ser | Phe | Ser | Ile 380 | Asn | Ser |  |

| TAT | AGT | GAT | GAA | TTG | GAA | ATC | TCG | TTA | TAT | GGT | TTA | ACC | CAA | 1773 |
|---|---|---|---|---|---|---|---|---|---|---|---|---|---|---|
| Tyr | Ser | Asp 385 | Glu | Leu | Glu | Ile | Ser 390 | Leu | Tyr | Gly | Leu | Thr 395 | Gln |  |

| AAG | GAA | ATC | ATA | CAG | ACA | TTG | CTG | GAA | GAA | CGA | TTT | TCC | GTA | 1815 |
|---|---|---|---|---|---|---|---|---|---|---|---|---|---|---|
| Lys | Glu | Ile | Ile 400 | Gln | Thr | Leu | Leu | Glu 405 | Glu | Arg | Phe | Ser | Val 410 |  |

| AAG | GTC | CAT | TTT | GAT | GAG | ATC | AAG | ACT | ATA | TAC | AAA | GAA | GGA | 1857 |
|---|---|---|---|---|---|---|---|---|---|---|---|---|---|---|
| Lys | Val | His | Phe | Asp 415 | Glu | Ile | Lys | Thr | Ile 420 | Tyr | Lys | Glu | Arg |  |

| CCT | GTA | AAA | AAG | GTC | AAT | AAG | ATT | TAA | CAG | ATC | GAA | GTG | CCG | 1899 |
|---|---|---|---|---|---|---|---|---|---|---|---|---|---|---|
| Pro 425 | Val | Lys | Lys | Val | Asn 430 | Lys | Ile | Ile | Gln | Ile 435 | Glu | Val | Pro |  |

| CCC | AAC | CCT | TAT | TGG | GCC | ACA | ATA | GGG | CTG | ACT | CTT | GAT | CCC | 1941 |
|---|---|---|---|---|---|---|---|---|---|---|---|---|---|---|
| Pro | Asn 440 | Pro | Tyr | Trp | Ala | Thr 445 | Ile | Gly | Leu | Thr | Leu 450 | Glu | Pro |  |

| TTA | CCG | TTA | GGG | ACA | GGG | TTG | CAA | ATC | GAA | AGT | GAC | ATC | TCC | 1983 |
|---|---|---|---|---|---|---|---|---|---|---|---|---|---|---|
| Leu | Pro | Leu | Gly 455 | Thr | Gly | Leu | Gln | Ile 460 | Glu | Ser | Asp | Ile | Ser 465 |  |

| TAT | GGT | TAT | CTG | AAC | CAT | TCT | TTT | CAA | AAT | GCC | GTT | TTT | GAA | 2025 |
|---|---|---|---|---|---|---|---|---|---|---|---|---|---|---|
| Tyr | Gly | Tyr | Leu 470 | Asn | His | Ser | Phe | Gln 475 | Asn | Ala | Val | Phe | Glu 480 |  |

| GGG | ATT | CGT | ATG | TCT | TGC | CAA | TCC | GGG | TTA | CAT | GGA | TGG | GAA | 2067 |
|---|---|---|---|---|---|---|---|---|---|---|---|---|---|---|

-continued

```
            Gly  Ile  Arg  Met  Ser  Cys  Gln  Ser  Gly  Leu  His  Gly  Trp  Glu
                            485                      490

GTG  ACT  GAT  CTG  AAA  GTA  ACT  TTT  ACT  CAA  GCC  GAG  TAT  TAT           2109
Val  Thr  Asp  Leu  Lys  Val  Thr  Phe  Thr  Gln  Ala  Glu  Tyr  Tyr
495                      500                      505

AGC  CCG  GTA  AGT  ACA  CCT  GCT  GAT  TTC  AGA  CAG  CTG  ACC  CCT           2151
Ser  Pro  Val  Ser  Tyr  Pro  Ala  Asp  Phe  Arg  Gln  Leu  Thr  Pro
     510                      515                      520

TAT  GTC  TTC  AGG  CTG  GCC  TTG  CAA  CAG  TCA  GGT  GTG  GAC  ATT           2193
Tyr  Val  Phe  Arg  Leu  Ala  Leu  Gln  Gln  Ser  Gly  Val  Asp  Ile
          525                      530                      535

CTC  GAA  CCG  ATG  CTC  TAT  TTT  GAG  TTG  CAG  ATA  CCC  CAA  GCG           2235
Leu  Glu  Pro  Met  Leu  Tyr  Phe  Glu  Leu  Gln  Ile  Pro  Gln  Ala
               540                      545                      550

GCA  AGT  TCC  AAA  GCT  ATT  ACA  GAT  TTG  CAA  AAA  ATG  ATG  TCT           2277
Ala  Ser  Ser  Lys  Ala  Ile  Thr  Asp  Leu  Gln  Lys  Met  Met  Ser
                    555                      560

GAG  ATT  GAA  GAC  ATC  AGT  TGC  AAT  AAT  GAG  TGG  TGT  CAT  ATT           2319
Glu  Ile  Glu  Asp  Ile  Ser  Cys  Asn  Asn  Glu  Trp  Cys  His  Ile
565                      570                      575

AAA  GGG  AAA  GTT  CCA  TTA  AAT  ACA  AGT  AAA  GAC  TAT  GCA  TCA           2361
Lys  Gly  Lys  Val  Pro  Leu  Asn  Thr  Ser  Lys  Asp  Tyr  Ala  Ser
     580                      585                      590

GAA  GTA  AGT  TCA  TAC  ACT  AAG  GGC  TTA  GGC  ATT  TTT  ATG  GTT           2403
Glu  Val  Ser  Ser  Tyr  Thr  Lys  Gly  Leu  Gly  Ile  Phe  Met  Val
          595                      600                      605

AAG  CCA  TGC  GGG  TAT  CAA  ATA  ACA  AAA  GGC  GGT  TAT  TCT  GAT           2445
Lys  Pro  Cys  Gly  Tyr  Gln  Ile  Thr  Lys  Gly  Gly  Tyr  Ser  Asp
               610                      615                      620

AAT  ATC  CGC  ATG  AAC  GAA  AAA  GAT  AAA  CTT  TTA  TTC  ATG  TTC           2487
Asn  Ile  Arg  Met  Asn  Glu  Lys  Asp  Lys  Leu  Leu  Phe  Met  Phe
                    625                      630

CAA  AAA  TCA  ATG  TCA  TCA  AAA  TAATGGAGCG  GTCAGGAAAT                      2528
Gln  Lys  Ser  Met  Ser  Ser  Lys
635                      640

TTCTATAAGG  CAATACAGTT  GGGATATATA  CTTATCTCCA  TTCTTATCGG                     2578

ATGTATGGCA  TATAATAGCC  TCTATGAATG  GCAGGAGATA  GAAGCATTAG                     2628

AACTTGGCAA  TAAAAAAATA  GACGAGCTC                                              2657
```

( 2 ) INFORMATION FOR SEQ ID NO:3:

( i ) SEQUENCE CHARACTERISTICS:
        ( A ) LENGTH: 641 amino acids
        ( B ) TYPE: amino acid
        ( C ) STRANDEDNESS:
        ( D ) TOPOLOGY: unknown ( x i ) SEQUENCE DESCRIPTION: SEQ ID NO:3:

```
Met  Asn  Ile  Ile  Asn  Leu  Gly  Ile  Leu  Ala  His  Ile  Asp  Ala  Gly
                    5                       10                      15

Lys  Thr  Ser  Val  Thr  Glu  Asn  Leu  Leu  Phe  Ala  Ser  Gly  Ala  Thr
                    20                      25                      30

Glu  Lys  Cys  Gly  Cys  Val  Asp  Asn  Gly  Asp  Thr  Ile  Thr  Asp  Ser
                    35                      40                      45

Met  Asp  Ile  Glu  Lys  Arg  Arg  Gly  Ile  Thr  Val  Arg  Ala  Ser  Thr
                    50                      55                      60

Thr  Ser  Ile  Ile  Trp  Asn  Gly  Val  Lys  Cys  Asn  Ile  Ile  Asp  Thr
                    65                      70                      75

Pro  Gly  His  Met  Asp  Phe  Ile  Ala  Glu  Val  Glu  Arg  Thr  Phe  Lys
```

-continued

|   |   |   |   | 80 |   |   |   |   | 85 |   |   |   |   | 90 |
|---|---|---|---|---|---|---|---|---|---|---|---|---|---|---|

Met Leu Asp Gly Ala Val Leu Ile Leu Ser Ala Lys Glu Gly Ile
                    95                 100                 105

Gln Ala Gln Thr Lys Leu Leu Phe Asn Thr Leu Gln Lys Leu Gln
                   110                 115                 120

Ile Pro Thr Ile Ile Phe Ile Asn Lys Ile Asp Arg Ala Gly Val
                   125                 130                 135

Asn Leu Glu Arg Leu Tyr Leu Asp Ile Lys Ala Asn Leu Ser Gln
                   140                 145                 150

Asp Val Leu Phe Met Gln Asn Val Val Asp Gly Ser Val Tyr Pro
                   155                 160                 165

Val Cys Ser Gln Thr Tyr Ile Lys Glu Glu Tyr Lys Glu Phe Val
                   170                 175                 180

Cys Asn His Asp Asp Asn Ile Leu Glu Arg Tyr Leu Ala Asp Ser
                   185                 190                 195

Glu Ile Ser Pro Ala Asp Tyr Trp Asn Thr Ile Ile Ala Leu Val
                   200                 205                 210

Ala Lys Ala Lys Val Tyr Pro Val Leu His Gly Ser Ala Met Phe
                   215                 220                 225

Asn Ile Gly Ile Asn Glu Leu Leu Asp Ala Ile Thr Ser Phe Ile
                   230                 235                 240

Leu Pro Pro Ala Ser Val Ser Asn Arg Leu Ser Ser Tyr Leu Tyr
                   245                 250                 255

Lys Ile Glu His Asp Pro Lys Gly His Lys Arg Ser Phe Leu Lys
                   260                 265                 270

Ile Ile Asp Gly Ser Leu Arg Leu Arg Asp Val Val Arg Ile Asn
                   275                 280                 285

Asp Ser Glu Lys Phe Ile Lys Ile Lys Asn Leu Lys Thr Ile Asn
                   290                 295                 300

Gln Gly Arg Glu Ile Asn Val Asp Glu Val Gly Ala Asn Asp Ile
                   305                 310                 315

Ala Ile Val Glu Asp Met Asp Asp Phe Arg Ile Gly Asn Tyr Leu
                   320                 325                 330

Gly Ala Glu Pro Cys Leu Ile Gln Gly Leu Ser His Gln His Pro
                   335                 340                 345

Ala Leu Lys Ser Ser Val Arg Pro Asp Arg Pro Glu Glu Arg Ser
                   350                 355                 360

Lys Val Ile Ser Ala Leu Asn Thr Leu Trp Ile Glu Asp Pro Ser
                   365                 370                 375

Leu Ser Phe Ser Ile Asn Ser Tyr Ser Asp Glu Leu Glu Ile Ser
                   380                 385                 390

Leu Tyr Gly Leu Thr Gln Lys Glu Ile Ile Gln Thr Leu Leu Glu
                   395                 400                 405

Glu Arg Phe Ser Val Lys Val His Phe Asp Glu Ile Lys Thr Ile
                   410                 415                 420

Tyr Lys Glu Arg Pro Val Lys Lys Val Asn Lys Ile Ile Gln Ile
                   425                 430                 435

Glu Val Pro Pro Asn Pro Tyr Trp Ala Thr Ile Gly Leu Thr Leu
                   440                 445                 450

Glu Pro Leu Pro Leu Gly Thr Gly Leu Gln Ile Glu Ser Asp Ile
                   455                 460                 465

Ser Tyr Gly Tyr Leu Asn His Ser Phe Gln Asn Ala Val Phe Glu
                   470                 475                 480

| | | | | | | | | | | | | |
|---|---|---|---|---|---|---|---|---|---|---|---|---|
| Gly | Ile | Arg | Met | Ser 485 | Cys | Gln | Ser | Gly 490 | Leu | His | Gly | Trp | Glu | Val 495 |

```
Gly  Ile  Arg  Met  Ser  Cys  Gln  Ser  Gly  Leu  His  Gly  Trp  Glu  Val
                    485                      490                      495

Thr  Asp  Leu  Lys  Val  Thr  Phe  Thr  Gln  Ala  Glu  Tyr  Tyr  Ser  Pro
                    500                      505                      510

Val  Ser  Tyr  Pro  Ala  Asp  Phe  Arg  Gln  Leu  Thr  Pro  Tyr  Val  Phe
                    515                      520                      525

Arg  Leu  Ala  Leu  Gln  Gln  Ser  Gly  Val  Asp  Ile  Leu  Glu  Pro  Met
                    530                      535                      540

Leu  Tyr  Phe  Glu  Leu  Gln  Ile  Pro  Gln  Ala  Ala  Ser  Ser  Lys  Ala
                    545                      550                      555

Ile  Thr  Asp  Leu  Gln  Lys  Met  Met  Ser  Glu  Ile  Glu  Asp  Ile  Ser
                    560                      565                      570

Cys  Asn  Asn  Glu  Trp  Cys  His  Ile  Lys  Gly  Lys  Val  Pro  Leu  Asn
                    575                      580                      585

Thr  Ser  Lys  Asp  Tyr  Ala  Ser  Glu  Val  Ser  Ser  Tyr  Thr  Lys  Gly
                    590                      595                      600

Leu  Gly  Ile  Phe  Met  Val  Lys  Pro  Cys  Gly  Tyr  Gln  Ile  Thr  Lys
                    605                      610                      615

Gly  Gly  Tyr  Ser  Asp  Asn  Ile  Arg  Met  Asn  Glu  Lys  Asp  Lys  Leu
                    620                      625                      630

Leu  Phe  Met  Phe  Gln  Lys  Ser  Met  Ser  Ser  Lys
                    635                      640
```

( 2 ) INFORMATION FOR SEQ ID NO:4:

( i ) SEQUENCE CHARACTERISTICS:
        ( A ) LENGTH: 2106 base pairs
        ( B ) TYPE: nucleic acid
        ( C ) STRANDEDNESS: double stranded
        ( D ) TOPOLOGY: circular ( x i ) SEQUENCE DESCRIPTION: SEQ ID NO:4:

```
AAAAATCCTC  CTACTTTTGT  TAGATATATT  TTTTTGTGTA  ATTTTGTAAT              50

CGTTATGCGG  CAGTAATAAT  ATACATATTA  ATACGAGTTA  GGAATCCTGT             100

AGTTCTCATA  TGCTACGAGG  AGGTATTAAA  AGGTGCGTTT  CGACAATGCA             150

TCTATTGTAG  TATATTATTG  CTTAATCCAA  ATG  AAT  ATT  ATA                 192
                                    Met  Asn  Ile  Ile

AAT  TTA  GGA  ATT  CTT  GCT  CAC  ATT  GAT  GCA  GGA  AAA  ACT  TCC   234
Asn  Leu  Gly  Ile  Leu  Ala  His  Ile  Asp  Ala  Gly  Lys  Thr  Ser
 5                  10                       15

GTA  ACC  GAG  AAT  CTG  CTG  TTT  GCC  AGT  GGA  GCA  ACG  GAA  AAG   276
Val  Thr  Glu  Asn  Leu  Leu  Phe  Ala  Ser  Gly  Ala  Thr  Glu  Lys
          20                       25                       30

TGC  GGC  TGT  GTG  GAT  AAT  GGT  GAC  ACC  ATA  ACG  GAC  TCT  ATG   318
Cys  Gly  Cys  Val  Asp  Asn  Gly  Asp  Thr  Ile  Thr  Asp  Ser  Met
               35                       40                       45

GAT  ATA  GAG  AAA  CGT  AGA  GGA  ATT  ACT  GTT  CGG  GCT  TCT  ACG   360
Asp  Ile  Glu  Lys  Arg  Arg  Gly  Ile  Thr  Val  Arg  Ala  Ser  Thr
                    50                       55                       60

ACA  TCT  ATT  ATC  TGG  AAT  GGT  GTG  AAA  TGC  AAT  ATC  ATT  GAC   402
Thr  Ser  Ile  Ile  Trp  Asn  Gly  Val  Lys  Cys  Asn  Ile  Ile  Asp
                    65                       70

ACT  CCG  GGA  CAC  ATG  GAT  TTT  ATT  GCG  GAA  GTG  GAG  CGG  ACA   444
Thr  Pro  Gly  His  Met  Asp  Phe  Ile  Ala  Glu  Val  Glu  Arg  Thr
 75                      80                       85

TTC  AAA  ATG  CTT  GAT  GGA  GCA  GTC  CTC  ATC  TTA  TCC  GCA  AAG   486
Phe  Lys  Met  Leu  Asp  Gly  Ala  Val  Leu  Ile  Leu  Ser  Ala  Lys
           90                       95                      100
```

```
GAA GGC ATA CAA GCG CAG ACA AAG TTG CTG TTC AAT ACT TTA        528
Glu Gly Ile Gln Ala Gln Thr Lys Leu Leu Phe Asn Thr Leu
        105             110                 115

CAG AAG CTG CAA ATC CCG ACA ATT ATA TTT ATC AAT AAG ATT        570
Gln Lys Leu Gln Ile Pro Thr Ile Ile Phe Ile Asn Lys Ile
        120             125                 130

GAC CGA GCC GGT GTG AAT TTG GAG CGT TTG TAT CTG GAT ATA        612
Asp Arg Ala Gly Val Asn Leu Glu Arg Leu Tyr Leu Asp Ile
                135             140

AAA GCA AAT CTG TCT CAA GAT GTC CTG TTT ATG CAA AAT GTT        654
Lys Ala Asn Leu Ser Gln Asp Val Leu Phe Met Gln Asn Val
145             150             155

GTC GAT GGA TCG GTT TAT CCG GTT TGC TCC CAA ACA TAT ATA        696
Val Asp Gly Ser Val Tyr Pro Val Cys Ser Gln Thr Tyr Ile
        160             165             170

AAG GAA GAA TAC AAA GAA TTT GTA TGC AAC CAT GAC GAC AAT        738
Lys Glu Glu Tyr Lys Glu Phe Val Cys Asn His Asp Asp Asn
                175             180             185

ATA TTA GAA CGA TAT TTG GCG GAT AGC GAA ATT TCA CCG GCT        780
Ile Leu Glu Arg Tyr Leu Ala Asp Ser Glu Ile Ser Pro Ala
                190             195             200

GAT TAT TGG AAT ACG ATA ATC GCT CTT GTG GCA AAA GCC AAA        822
Asp Tyr Trp Asn Thr Ile Ile Ala Leu Val Ala Lys Ala Lys
                205             210

GTC TAT CCG GTG CTA CAT GGA TCA GCA ATG TTC AAT ATC GGT        864
Val Tyr Pro Val Leu His Gly Ser Ala Met Phe Asn Ile Gly
215             220             225

ATC AAT GAG TTG TTG GAC GCC ATC ACT TCT TTT ATA CTT CCT        906
Ile Asn Glu Leu Leu Asp Ala Ile Thr Ser Phe Ile Leu Pro
        230             235             240

CCG GCA TCG GTC TCA AAC AGA CTT TCA TCT TAT CTT TAT AAG        948
Pro Ala Ser Val Ser Asn Arg Leu Ser Ser Tyr Leu Tyr Lys
        245             250             255

ATA GAG CAT GAC CCC AAA GGA CAT AAA AGA AGT TTT CTA AAA        990
Ile Glu His Asp Pro Lys Gly His Lys Arg Ser Phe Leu Lys
                260             265             270

ATA ATT GAC GGA AGT CTG AGA CTT CGA GAC GTT GTA AGA ATC       1032
Ile Ile Asp Gly Ser Leu Arg Leu Arg Asp Val Val Arg Ile
                275             280

AAC GAT TCG GAA AAA TTC ATC AAG ATT AAA AAT CTA AAA ACT       1074
Asn Asp Ser Glu Lys Phe Ile Lys Ile Lys Asn Leu Lys Thr
285             290             295

ATC AAT CAG GGC AGA GAG ATA AAT GTT GAT GAA GTG GGC GCC       1116
Ile Asn Gln Gly Arg Glu Ile Asn Val Asp Glu Val Gly Ala
        300             305             310

AAT GAT ATC GCG ATT GTA GAG GAT ATG GAT GAT TTT CGA ATC       1158
Asn Asp Ile Ala Ile Val Glu Asp Met Asp Asp Phe Arg Ile
        315             320             325

GGA AAT TAT TTA GGT GCT GAA CCT TGT TTG ATT CAA GGA TTA       1200
Gly Asn Tyr Leu Gly Ala Glu Pro Cys Leu Ile Gln Gly Leu
        330             335             340

TCG CAT CAG CAT CCC GCT CTC AAA TCC TCC GTC CGG CCA GAC       1242
Ser His Gln His Pro Ala Leu Lys Ser Ser Val Arg Pro Asp
                345             350

AGG CCC GAA GAG AGA AGC AAG GTG ATA TCC GCT CTG AAT ACA       1284
Arg Pro Glu Glu Arg Ser Lys Val Ile Ser Ala Leu Asn Thr
355             360             365

TTG TGG ATT GAA GAC CCG TCT TTG TCC TTT TCC ATA AAC TCA       1326
Leu Trp Ile Glu Asp Pro Ser Leu Ser Phe Ser Ile Asn Ser
        370             375             380
```

| | | | | | | | | | | | | | |
|---|---|---|---|---|---|---|---|---|---|---|---|---|---|
| TAT | AGT | GAT | GAA | TTG | GAA | ATC | TCG | TTA | TAT | GGT | TTA | ACC | CAA | 1368 |
| Tyr | Ser | Asp<br>385 | Glu | Leu | Glu | Ile | Ser<br>390 | Leu | Tyr | Gly | Leu | Thr<br>395 | Gln | |
| AAG | GAA | ATC | ATA | CAG | ACA | TTG | CTG | GAA | GAA | CGA | TTT | TCC | GTA | 1410 |
| Lys | Glu | Ile | Ile<br>400 | Gln | Thr | Leu | Leu | Glu | Glu<br>405 | Arg | Phe | Ser | Val<br>410 | |
| AAG | GTC | CAT | TTT | GAT | GAG | ATC | AAG | ACT | ATA | TAC | AAA | GAA | GGA | 1452 |
| Lys | Val | His | Phe | Asp<br>415 | Glu | Ile | Lys | Thr | Ile<br>420 | Tyr | Lys | Glu | Arg | |
| CCT | GTA | AAA | AAG | GTC | AAT | AAG | ATT | TAA | CAG | ATC | GAA | GTG | CCG | 1494 |
| Pro<br>425 | Val | Lys | Lys | Val<br>430 | Asn | Lys | Ile | Ile | Gln<br>435 | Ile | Glu | Val | Pro | |
| CCC | AAC | CCT | TAT | TGG | GCC | ACA | ATA | GGG | CTG | ACT | CTT | GAT | CCC | 1536 |
| Pro | Asn<br>440 | Pro | Tyr | Trp | Ala | Thr | Ile<br>445 | Gly | Leu | Thr | Leu | Glu<br>450 | Pro | |
| TTA | CCG | TTA | GGG | ACA | GGG | TTG | CAA | ATC | GAA | AGT | GAC | ATC | TCC | 1578 |
| Leu | Pro | Leu<br>455 | Gly | Thr | Gly | Leu | Gln<br>460 | Ile | Glu | Ser | Asp | Ile<br>465 | Ser | |
| TAT | GGT | TAT | CTG | AAC | CAT | TCT | TTT | CAA | AAT | GCC | GTT | TTT | GAA | 1620 |
| Tyr | Gly | Tyr | Leu<br>470 | Asn | His | Ser | Phe | Gln<br>475 | Asn | Ala | Val | Phe | Glu<br>480 | |
| GGG | ATT | CGT | ATG | TCT | TGC | CAA | TCC | GGG | TTA | CAT | GGA | TGG | GAA | 1662 |
| Gly | Ile | Arg | Met | Ser<br>485 | Cys | Gln | Ser | Gly | Leu<br>490 | His | Gly | Trp | Glu | |
| GTG | ACT | GAT | CTG | AAA | GTA | ACT | TTT | ACT | CAA | GCC | GAG | TAT | TAT | 1704 |
| Val<br>495 | Thr | Asp | Leu | Lys | Val<br>500 | Thr | Phe | Thr | Gln | Ala<br>505 | Glu | Tyr | Tyr | |
| AGC | CCG | GTA | AGT | ACA | CCT | GCT | GAT | TTC | AGA | CAG | CTG | ACC | CCT | 1746 |
| Ser | Pro | Val<br>510 | Ser | Tyr | Pro | Ala | Asp<br>515 | Phe | Arg | Gln | Leu | Thr<br>520 | Pro | |
| TAT | GTC | TTC | AGG | CTG | GCC | TTG | CAA | CAG | TCA | GGT | GTG | GAC | ATT | 1788 |
| Tyr | Val | Phe<br>525 | Arg | Leu | Ala | Leu | Gln<br>530 | Gln | Ser | Gly | Val | Asp<br>535 | Ile | |
| CTC | GAA | CCG | ATG | CTC | TAT | TTT | GAG | TTG | CAG | ATA | CCC | CAA | GCG | 1830 |
| Leu | Glu | Pro | Met<br>540 | Leu | Tyr | Phe | Glu | Leu<br>545 | Gln | Ile | Pro | Gln | Ala<br>550 | |
| GCA | AGT | TCC | AAA | GCT | ATT | ACA | GAT | TTG | CAA | AAA | ATG | ATG | TCT | 1872 |
| Ala | Ser | Ser | Lys | Ala<br>555 | Ile | Thr | Asp | Leu | Gln<br>560 | Lys | Met | Met | Ser | |
| GAG | ATT | GAA | GAC | ATC | AGT | TGC | AAT | AAT | GAG | TGG | TGT | CAT | ATT | 1914 |
| Glu<br>565 | Ile | Glu | Asp | Ile | Ser<br>570 | Cys | Asn | Asn | Glu | Trp<br>575 | Cys | His | Ile | |
| AAA | GGG | AAA | GTT | CCA | TTA | AAT | ACA | AGT | AAA | GAC | TAT | GCA | TCA | 1956 |
| Lys | Gly<br>580 | Lys | Val | Pro | Leu | Asn<br>585 | Thr | Ser | Lys | Asp | Tyr<br>590 | Ala | Ser | |
| GAA | GTA | AGT | TCA | TAC | ACT | AAG | GGC | TTA | GGC | ATT | TTT | ATG | GTT | 1998 |
| Glu | Val | Ser<br>595 | Ser | Tyr | Thr | Lys | Gly<br>600 | Leu | Gly | Ile | Phe | Met<br>605 | Val | |
| AAG | CCA | TGC | GGG | TAT | CAA | ATA | ACA | AAA | GGC | GGT | TAT | TCT | GAT | 2040 |
| Lys | Pro | Cys | Gly<br>610 | Tyr | Gln | Ile | Thr | Lys<br>615 | Gly | Gly | Tyr | Ser | Asp<br>620 | |
| AAT | ATC | CGC | ATG | AAC | GAA | AAA | GAT | AAA | CTT | TTA | TTC | ATG | TTC | 2082 |
| Asn | Ile | Arg | Met | Asn<br>625 | Glu | Lys | Asp | Lys | Leu<br>630 | Leu | Phe | Met | Phe | |
| CAA | AAA | TCA | ATG | TCA | TCA | AAA | TAA | | | | | | | 2106 |
| Gln | Lys | Ser<br>635 | Met | Ser | Ser<br>640 | Lys | | | | | | | | |

( 2 ) INFORMATION FOR SEQ ID NO:5:

( i ) SEQUENCE CHARACTERISTICS:
  ( A ) LENGTH: 1926 base pairs
  ( B ) TYPE: nucleic acid
  ( C ) STRANDEDNESS: double stranded
  ( D ) TOPOLOGY: circular ( x i ) SEQUENCE DESCRIPTION: SEQ ID NO:5:

```
ATG AAT ATT ATA AAT TTA GGA ATT CTT GCT CAC ATT GAT GCA           42
Met Asn Ile Ile Asn Leu Gly Ile Leu Ala His Ile Asp Ala
              5                   10

GGA AAA ACT TCC GTA ACC GAG AAT CTG CTG TTT GCC AGT GGA           84
Gly Lys Thr Ser Val Thr Glu Asn Leu Leu Phe Ala Ser Gly
 15                  20                  25

GCA ACG GAA AAG TGC GGC TGT GTG GAT AAT GGT GAC ACC ATA          126
Ala Thr Glu Lys Cys Gly Cys Val Asp Asn Gly Asp Thr Ile
     30                  35                  40

ACG GAC TCT ATG GAT ATA GAG AAA CGT AGA GGA ATT ACT GTT          168
Thr Asp Ser Met Asp Ile Glu Lys Arg Arg Gly Ile Thr Val
             45                  50                  55

CGG GCT TCT ACG ACA TCT ATT ATC TGG AAT GGT GTG AAA TGC          210
Arg Ala Ser Thr Thr Ser Ile Ile Trp Asn Gly Val Lys Cys
                 60                  65                  70

AAT ATC ATT GAC ACT CCG GGA CAC ATG GAT TTT ATT GCG GAA          252
Asn Ile Ile Asp Thr Pro Gly His Met Asp Phe Ile Ala Glu
                     75                  80

GTG GAG CGG ACA TTC AAA ATG CTT GAT GGA GCA GTC CTC ATC          294
Val Glu Arg Thr Phe Lys Met Leu Asp Gly Ala Val Leu Ile
 85                  90                  95

TTA TCC GCA AAG GAA GGC ATA CAA GCG CAG ACA AAG TTG CTG          336
Leu Ser Ala Lys Glu Gly Ile Gln Ala Gln Thr Lys Leu Leu
    100                 105                 110

TTC AAT ACT TTA CAG AAG CTG CAA ATC CCG ACA ATT ATA TTT          378
Phe Asn Thr Leu Gln Lys Leu Gln Ile Pro Thr Ile Ile Phe
            115                 120                 125

ATC AAT AAG ATT GAC CGA GCC GGT GTG AAT TTG GAG CGT TTG          420
Ile Asn Lys Ile Asp Arg Ala Gly Val Asn Leu Glu Arg Leu
                130                 135                 140

TAT CTG GAT ATA AAA GCA AAT CTG TCT CAA GAT GTC CTG TTT          462
Tyr Leu Asp Ile Lys Ala Asn Leu Ser Gln Asp Val Leu Phe
                    145                 150

ATG CAA AAT GTT GTC GAT GGA TCG GTT TAT CCG GTT TGC TCC          504
Met Gln Asn Val Val Asp Gly Ser Val Tyr Pro Val Cys Ser
155                 160                 165

CAA ACA TAT ATA AAG GAA GAA TAC AAA GAA TTT GTA TGC AAC          546
Gln Thr Tyr Ile Lys Glu Glu Tyr Lys Glu Phe Val Cys Asn
        170                 175                 180

CAT GAC GAC AAT ATA TTA GAA CGA TAT TTG GCG GAT AGC GAA          588
His Asp Asp Asn Ile Leu Glu Arg Tyr Leu Ala Asp Ser Glu
                185                 190                 195

ATT TCA CCG GCT GAT TAT TGG AAT ACG ATA ATC GCT CTT GTG          630
Ile Ser Pro Ala Asp Tyr Trp Asn Thr Ile Ile Ala Leu Val
                    200                 205                 210

GCA AAA GCC AAA GTC TAT CCG GTG CTA CAT GGA TCA GCA ATG          672
Ala Lys Ala Lys Val Tyr Pro Val Leu His Gly Ser Ala Met
                        215                 220

TTC AAT ATC GGT ATC AAT GAG TTG TTG GAC GCC ATC ACT TCT          714
Phe Asn Ile Gly Ile Asn Glu Leu Leu Asp Ala Ile Thr Ser
225                 230                 235

TTT ATA CTT CCT CCG GCA TCG GTC TCA AAC AGA CTT TCA TCT          756
Phe Ile Leu Pro Pro Ala Ser Val Ser Asn Arg Leu Ser Ser
    240                 245                 250
```

-continued

| | | | | | | | | | | | | | | |
|---|---|---|---|---|---|---|---|---|---|---|---|---|---|---|
| TAT | CTT | TAT | AAG | ATA | GAG | CAT | GAC | CCC | AAA | GGA | CAT | AAA | AGA | 798 |
| Tyr | Leu | Tyr | Lys | Ile | Glu | His | Asp | Pro | Lys | Gly | His | Lys | Arg | |
| | | 255 | | | | 260 | | | | | 265 | | | |
| AGT | TTT | CTA | AAA | ATA | ATT | GAC | GGA | AGT | CTG | AGA | CTT | CGA | GAC | 840 |
| Ser | Phe | Leu | Lys | Ile | Ile | Asp | Gly | Ser | Leu | Arg | Leu | Arg | Asp | |
| | | | 270 | | | | 275 | | | | | 280 | | |
| GTT | GTA | AGA | ATC | AAC | GAT | TCG | GAA | AAA | TTC | ATC | AAG | ATT | AAA | 882 |
| Val | Val | Arg | Ile | Asn | Asp | Ser | Glu | Lys | Phe | Ile | Lys | Ile | Lys | |
| | | | | 285 | | | | 290 | | | | | | |
| AAT | CTA | AAA | ACT | ATC | AAT | CAG | GGC | AGA | GAG | ATA | AAT | GTT | GAT | 924 |
| Asn | Leu | Lys | Thr | Ile | Asn | Gln | Gly | Arg | Glu | Ile | Asn | Val | Asp | |
| 295 | | | | | 300 | | | | | 305 | | | | |
| GAA | GTG | GGC | GCC | AAT | GAT | ATC | GCG | ATT | GTA | GAG | GAT | ATG | GAT | 966 |
| Glu | Val | Gly | Ala | Asn | Asp | Ile | Ala | Ile | Val | Glu | Asp | Met | Asp | |
| | 310 | | | | | 315 | | | | | 320 | | | |
| GAT | TTT | CGA | ATC | GGA | AAT | TAT | TTA | GGT | GCT | GAA | CCT | TGT | TTG | 1008 |
| Asp | Phe | Arg | Ile | Gly | Asn | Tyr | Leu | Gly | Ala | Glu | Pro | Cys | Leu | |
| | | 325 | | | | 330 | | | | | 335 | | | |
| ATT | CAA | GGA | TTA | TCG | CAT | CAG | CAT | CCC | GCT | CTC | AAA | TCC | TCC | 1050 |
| Ile | Gln | Gly | Leu | Ser | His | Gln | His | Pro | Ala | Leu | Lys | Ser | Ser | |
| | | | 340 | | | | 345 | | | | | 350 | | |
| GTC | CGG | CCA | GAC | AGG | CCC | GAA | GAG | AGA | AGC | AAG | GTG | ATA | TCC | 1092 |
| Val | Arg | Pro | Asp | Arg | Pro | Glu | Glu | Arg | Ser | Lys | Val | Ile | Ser | |
| | | | | 355 | | | | 360 | | | | | | |
| GCT | CTG | AAT | ACA | TTG | TGG | ATT | GAA | GAC | CCG | TCT | TTG | TCC | TTT | 1134 |
| Ala | Leu | Asn | Thr | Leu | Trp | Ile | Glu | Asp | Pro | Ser | Leu | Ser | Phe | |
| 365 | | | | | 370 | | | | | 375 | | | | |
| TCC | ATA | AAC | TCA | TAT | AGT | GAT | GAA | TTG | GAA | ATC | TCG | TTA | TAT | 1176 |
| Ser | Ile | Asn | Ser | Tyr | Ser | Asp | Glu | Leu | Glu | Ile | Ser | Leu | Tyr | |
| | | 380 | | | | 385 | | | | | 390 | | | |
| GGT | TTA | ACC | CAA | AAG | GAA | ATC | ATA | CAG | ACA | TTG | CTG | GAA | GAA | 1218 |
| Gly | Leu | Thr | Gln | Lys | Glu | Ile | Ile | Gln | Thr | Leu | Leu | Glu | Glu | |
| | | | 395 | | | | 400 | | | | | 405 | | |
| CGA | TTT | TCC | GTA | AAG | GTC | CAT | TTT | GAT | GAG | ATC | AAG | ACT | ATA | 1260 |
| Arg | Phe | Ser | Val | Lys | Val | His | Phe | Asp | Glu | Ile | Lys | Thr | Ile | |
| | | | 410 | | | | 415 | | | | | 420 | | |
| TAC | AAA | GAA | GGA | CCT | GTA | AAA | AAG | GTC | AAT | AAG | ATT | TAA | CAG | 1302 |
| Tyr | Lys | Glu | Arg | Pro | Val | Lys | Lys | Val | Asn | Lys | Ile | Ile | Gln | |
| | | | | 425 | | | | 430 | | | | | | |
| ATC | GAA | GTG | CCG | CCC | AAC | CCT | TAT | TGG | GCC | ACA | ATA | GGG | CTG | 1344 |
| Ile | Glu | Val | Pro | Pro | Asn | Pro | Tyr | Trp | Ala | Thr | Ile | Gly | Leu | |
| 435 | | | | | 440 | | | | | 445 | | | | |
| ACT | CTT | GAT | CCC | TTA | CCG | TTA | GGG | ACA | GGG | TTG | CAA | ATC | GAA | 1386 |
| Thr | Leu | Asp | Pro | Leu | Pro | Leu | Gly | Thr | Gly | Leu | Gln | Ile | Glu | |
| | | 450 | | | | 455 | | | | | 460 | | | |
| AGT | GAC | ATC | TCC | TAT | GGT | TAT | CTG | AAC | CAT | TCT | TTT | CAA | AAT | 1428 |
| Ser | Asp | Ile | Ser | Tyr | Gly | Tyr | Leu | Asn | His | Ser | Phe | Gln | Asn | |
| | | | 465 | | | | 470 | | | | | 475 | | |
| GCC | GTT | TTT | GAA | GGG | ATT | CGT | ATG | TCT | TGC | CAA | TCC | GGG | TTA | 1470 |
| Ala | Val | Phe | Glu | Gly | Ile | Arg | Met | Ser | Cys | Gln | Ser | Gly | Leu | |
| | | | 480 | | | | 485 | | | | | 490 | | |
| CAT | GGA | TGG | GAA | GTG | ACT | GAT | CTG | AAA | GTA | ACT | TTT | ACT | CAA | 1512 |
| His | Gly | Trp | Glu | Val | Thr | Asp | Leu | Lys | Val | Thr | Phe | Thr | Gln | |
| | | | | 495 | | | | 500 | | | | | | |
| GCC | GAG | TAT | TAT | AGC | CCG | GTA | AGT | ACA | CCT | GCT | GAT | TTC | AGA | 1554 |
| Ala | Glu | Tyr | Tyr | Ser | Pro | Val | Ser | Tyr | Pro | Ala | Asp | Phe | Arg | |
| 505 | | | | | 510 | | | | | 515 | | | | |
| CAG | CTG | ACC | CCT | TAT | GTC | TTC | AGG | CTG | GCC | TTG | CAA | CAG | TCA | 1596 |
| Gln | Leu | Thr | Pro | Tyr | Val | Phe | Arg | Leu | Ala | Leu | Gln | Gln | Ser | |
| | | 520 | | | | 525 | | | | | 530 | | | |

| | | | | | | | | | | | | | | |
|---|---|---|---|---|---|---|---|---|---|---|---|---|---|---|
| GGT | GTG | GAC | ATT | CTC | GAA | CCG | ATG | CTC | TAT | TTT | GAG | TTG | CAG | 1638 |
| Gly | Val | Asp | Ile | Leu | Glu | Pro | Met | Leu | Tyr | Phe | Glu | Leu | Gln | |
| | | 535 | | | | | 540 | | | | | 545 | | |
| ATA | CCC | CAA | GCG | GCA | AGT | TCC | AAA | GCT | ATT | ACA | GAT | TTG | CAA | 1680 |
| Ile | Pro | Gln | Ala | Ala | Ser | Ser | Lys | Ala | Ile | Thr | Asp | Leu | Gln | |
| | | | 550 | | | | | 555 | | | | | 560 | |
| AAA | ATG | ATG | TCT | GAG | ATT | GAA | GAC | ATC | AGT | TGC | AAT | AAT | GAG | 1722 |
| Lys | Met | Met | Ser | Glu | Ile | Glu | Asp | Ile | Ser | Cys | Asn | Asn | Glu | |
| | | | | 565 | | | | | 570 | | | | | |
| TGG | TGT | CAT | ATT | AAA | GGG | AAA | GTT | CCA | TTA | AAT | ACA | AGT | AAA | 1764 |
| Trp | Cys | His | Ile | Lys | Gly | Lys | Val | Pro | Leu | Asn | Thr | Ser | Lys | |
| 575 | | | | | 580 | | | | | 585 | | | | |
| GAC | TAT | GCA | TCA | GAA | GTA | AGT | TCA | TAC | ACT | AAG | GGC | TTA | GGC | 1806 |
| Asp | Tyr | Ala | Ser | Glu | Val | Ser | Ser | Tyr | Thr | Lys | Gly | Leu | Gly | |
| | | 590 | | | | | 595 | | | | | 600 | | |
| ATT | TTT | ATG | GTT | AAG | CCA | TGC | GGG | TAT | CAA | ATA | ACA | AAA | GGC | 1848 |
| Ile | Phe | Met | Val | Lys | Pro | Cys | Gly | Tyr | Gln | Ile | Thr | Lys | Gly | |
| | | 605 | | | | | 610 | | | | | 615 | | |
| GGT | TAT | TCT | GAT | AAT | ATC | CGC | ATG | AAC | GAA | AAA | GAT | AAA | CTT | 1890 |
| Gly | Tyr | Ser | Asp | Asn | Ile | Arg | Met | Asn | Glu | Lys | Asp | Lys | Leu | |
| | | | 620 | | | | | 625 | | | | | 630 | |
| TTA | TTC | ATG | TTC | CAA | AAA | TCA | ATG | TCA | TCA | AAA | TAA | | | 1926 |
| Leu | Phe | Met | Phe | Gln | Lys | Ser | Met | Ser | Ser | Lys | | | | |
| | | | | 635 | | | | | 640 | | | | | |

We claim:

1. An engineered *Prevotella ruminicola* comprising expressible foreign DNA, said DNA introduced into the *Prevotella ruminicola* by a method comprising the steps of:
   (a) transforming an *Escherichia coli* with a shuttle vector comprising:
      (i) a mobilization region which permits transfer of the shuttle vector from *Escherichia coli* to a colonic Bacteroides species;
      (ii) a mobilization region which permits transfer of the shuttle vector from the colonic Bacteroides species to a *P. ruminicola*; and
      (iii) heterologous DNA operatively linked to a promoter functional in the *P. ruminicola*;
   (b) contacting the *E. coli* with a colonic Bacteroides species under conditions sufficient so that the shuttle vector is transferred from the *E. coli* to the colonic Bacteroides species; and
   (c) contacting the colonic Bacteroides species with the *P. ruminicola* under conditions sufficient so that the shuttle vector is transferred from the colonic Bacteroides species to the *P. ruminicola*.

2. The *P. ruminicola* of claim 1 wherein the foreign DNA is under control of a promoter which comprises the sequence:

| | | | | | |
|---|---|---|---|---|---|
| AAAAATCCTC | CTACTTTTGT | TAGATATATT | TTTTTGTGTA | ATTTTGTAAT | 50 |
| CGTTATGCGG | CAGTAATAAT | ATACATATTA | ATACGAGTTA | TTAATCCTGT | 100 |
| AGTTCTCATA | TGCTACGAGG | AGGTATTAAA | AGGTGCGTTT | CGACAATGCA | 150 |
| TCTATTGTAG | TATATTATTG | CTTAATCCAA | (Seq ID No: 1) | | 180 |

3. The *P. ruminicola* of claim 1 wherein the foreign DNA is under control of the promoter of a TetQ gene having the nucleotide sequence of SEQ ID NO:1.

4. An isolated tetracycline resistance gene of the TetQ class, or fragments thereof that confer tetracycline resistance, the gene containing no more than 2700 deoxyribonucleotides per DNA strand.

5. The gene of claim 4 which comprises the following sequence:

```
AAAAATCCTC CTACTTTTGT TAGATATATT TTTTTGTGTA ATTTTGTAAT      50

CGTTATGCGG CAGTAATAAT ATACATATTA ATACGAGTTA GGAATCCTGT     100

AGTTCTCATA TGCTACGAGG AGGTATTAAA AGGTGCGTTT CGACAATGCA     150

TCTATTGTAG TATATTATTG CTTAATCCAA ATG AAT ATA ATA           192
                                  Met Asn Ile Ile

AAT TTA GGA ATT CTT GCT CAC ATT GAT GCA GGA AAA ACT TCC    234
Asn Leu Gly Ile Leu Ala His Ile Asp Ala Gly Lys Thr Ser
 5              10                  15

GTA ACC GAG AAT CTG CTG TTT GCC AGT GGA GCA ACG GAA AAG    276
Val Thr Glu Asn Leu Leu Phe Ala Ser Gly Ala Thr Glu Lys
        20              25                  30

TGC GGC TGT GTG GAT AAT GGT GAC ACC ATA ACG GAC TCT ATG    318
Cys Gly Cys Val Asp Asn Gly Asp Thr Ile Thr Asp Ser Met
            35              40                  45

GAT ATA GAG AAA CGT AGA GGA ATT ACT GTT CGG GCT TCT ACG    360
Asp Ile Glu Lys Arg Arg Gly Ile Thr Val Arg Ala Ser Thr
                50                  55                  60

ACA TCT ATT ATC TGG AAT GGT GTG AAA TGC AAT ATC ATT GAC    402
Thr Ser Ile Ile Trp Asn Gly Val Lys Cys Asn Ile Ile Asp
                    65                  70

ACT CCG GGA CAC ATG GAT TTT ATT GCG GAA GTG GAG CGG ACA    444
Thr Pro Gly His Met Asp Phe Ile Ala Glu Val Glu Arg Thr
 75              80                  85

TTC AAA ATG CTT GAT GGA GCA GTC CTC ATC TTA TCC GCA AAG    486
Phe Lys Met Leu Asp Gly Ala Val Leu Ile Leu Ser Ala Lys
        90              95                  100

GAA GGC ATA CAA GCG CAG ACA AAG TTG CTG TTC AAT ACT TTA    528
Glu Gly Ile Gln Ala Gln Thr Lys Leu Leu Phe Asn Thr Leu
            105             110                 115

CAG AAG CTG CAA ATC CCG ACA ATT ATA TTT ATC AAT AAG ATT    570
Gln Lys Leu Gln Ile Pro Thr Ile Ile Phe Ile Asn Lys Ile
                120                 125                 130

GAC CGA GCC GGT GTG AAT TTG GAG CGT TTG TAT CTG GAT ATA    612
Asp Arg Ala Gly Val Asn Leu Glu Arg Leu Tyr Leu Asp Ile
                    135                 140

AAA GCA AAT CTG TCT CAA GAT GTC CTG TTT ATG CAA AAT GTT    654
Lys Ala Asn Leu Ser Gln Asp Val Leu Phe Met Gln Asn Val
145             150                 155

GTC GAT GGA TCG GTT TAT CCG GTT TGC TCC CAA ACA TAT ATA    696
Val Asp Gly Ser Val Tyr Pro Val Cys Ser Gln Thr Tyr Ile
        160                 165                 170

AAG GAA GAA TAC AAA GAA TTT GTA TGC AAC CAT GAC GAC AAT    738
Lys Glu Glu Tyr Lys Glu Phe Val Cys Asn His Asp Asp Asn
            175                 180                 185

ATA TTA GAA CGA TAT TTG GCG GAT AGC GAA ATT TCA CCG GCT    780
Ile Leu Glu Arg Tyr Leu Ala Asp Ser Glu Ile Ser Pro Ala
                190                 195                 200

GAT TAT TGG AAT ACG ATA ATC GCT CTT GTG GCA AAA GCC AAA    822
Asp Tyr Trp Asn Thr Ile Ile Ala Leu Val Ala Lys Ala Lys
                    205                 210

GTC TAT CCG GTG CTA CAT GGA TCA GCA ATG TTC AAT ATC GGT    864
Val Tyr Pro Val Leu His Gly Ser Ala Met Phe Asn Ile Gly
215             220                 225

ATC AAT GAG TTG TTG GAC GCC ATC ACT TCT TTT ATA CTT CCT    906
Ile Asn Glu Leu Leu Asp Ala Ile Thr Ser Phe Ile Leu Pro
        230                 235                 240

CCG GCA TCG GTC TCA AAC AGA CTT TCA TCT TAT CTT TAT AAG    948
Pro Ala Ser Val Ser Asn Arg Leu Ser Ser Tyr Leu Tyr Lys
            245                 250                 255
```

```
ATA GAG CAT GAC CCC AAA GGA CAT AAA AGA AGT TTT CTA AAA          990
Ile Glu His Asp Pro Lys Gly His Lys Arg Ser Phe Leu Lys
        260                 265                     270

ATA ATT GAC GGA AGT CTG AGA CTT CGA GAC GTT GTA AGA ATC         1032
Ile Ile Asp Gly Ser Leu Arg Leu Arg Asp Val Val Arg Ile
            275                 280

AAC GAT TCG GAA AAA TTC ATC AAG ATT AAA AAT CTA AAA ACT         1074
Asn Asp Ser Glu Lys Phe Ile Lys Ile Lys Asn Leu Lys Tyr
285                 290             295

ATC AAT CAG GGC AGA GAG ATA AAT GTT GAT GAA GTG GGC GCC         1116
Ile Asn Gln Gly Arg Glu Ile Asn Val Asp Glu Val Gly Ala
    300                 305                 310

AAT GAT ATC GCG ATT GTA GAG GAT ATG GAT GAT TTT CGA ATC         1158
Asn Asp Ile Ala Ile Val Glu Asp Met Asp Asp Phe Arg Ile
        315             320             325

GGA AAT TAT TTA GGT GCT GAA CCT TGT TTG ATT CAA GGA TTA         1200
Gly Asn Tyr Leu Gly Ala Glu Pro Cys Leu Ile Gln Gly Leu
            330             335                 340

TCG CAT CAG CAT CCC GCT CTC AAA TCC TCC GTC CGG CCA GAC         1242
Ser His Gln His Pro Ala Leu Lys Ser Ser Val Arg Pro Asp
                345             350

AGG CCC GAA GAG AGA AGC AAG GTG ATA TCC GCT CTG AAT ACA         1284
Arg Pro Glu Glu Arg Ser Lys Val Ile Ser Ala Leu Asn Thr
355                 360             365

TTG TGG ATT GAA GAC CCG TCT TTG TCC TTT TCC ATA AAC TCA         1326
Leu Trp Ile Glu Asp Pro Ser Leu Ser Phe Ser Ile Asn Ser
    370                 375             380

TAT AGT GAT GAA TTG GAA ATC TCG TTA TAT GGT TTA ACC CAA         1368
Tyr Ser Asp Glu Leu Glu Ile Ser Leu Tyr Gly Leu Thr Gln
        385             390             395

AAG GAA ATC ATA CAG ACA TTG CTG GAA GAA CGA TTT TCC GTA         1410
Lys Glu Ile Ile Gln Thr Leu Leu Glu Glu Arg Phe Ser Val
            400             405                 410

AAG GTC CAT TTT GAT GAG ATC AAG ACT ATA TAC AAA GAA GGA         1452
Lys Val His Phe Asp Glu Ile Lys Thr Ile Tyr Lys Glu Arg
                415             420

CCT GTA AAA AAG GTC AAT AAG ATT TAA CAG ATC GAA GTG CCG         1494
Pro Val Lys Lys Val Asn Lys Ile Ile Gln Ile Glu Val Pro
425                 430             435

CCC AAC CCT TAT TGG GCC ACA ATA GGG CTG ACT CTT GAT CCC         1536
Pro Asn Pro Tyr Trp Ala Thr Ile Gly Leu Thr Leu Asp Pro
    440                 445             450

TTA CCG TTA GGG ACA GGG TTG CAA ATC GAA AGT GAC ATC TCC         1578
Leu Pro Ile Gly Thr Gly Leu Gln Ile Glu Ser Asp Ile Ser
        455             460             465

TAT GGT TAT CTG AAC CAT TCT TTT CAA AAT GCC GTT TTT GAA         1620
Tyr Gly Tyr Leu Asn His Ser Phe Gln Asn Ala Val Phe Arg
            470             475                 480

GGG ATT CGT ATG TCT TGC CAA TCC GGG TTA CAT GGA TGG GAA         1662
Gly Ile Arg Met Ser Cys Gln Ser Gly Leu His Gly Trp Glu
                485             490

GTG ACT GAT CTG AAA GTA ACT TTT ACT CAA GCC GAG TAT TAT         1704
Val Thr Asp Leu Lys Val Thr Phe Thr Gln Ala Glu Tyr Tyr
495                 500             505

AGC CCG GTA AGT ACA CCT GCT GAT TTC AGA CAG CTG ACC CCT         1746
Ser Pro Val Ser Tyr Pro Ala Asp Phe Arg Gln Leu Thr Pro
    510                 515             520

TAT GTC TTC AGG CTG GCC TTG CAA CAG TCA GGT GTG GAC ATT         1788
Tyr Val Phe Arg Leu Ala Leu Gln Gln Ser Gly Val Asp Ile
        525             530             535

CTC GAA CCG ATG CTC TAT TTT GAG TTG CAG ATA CCC CAA GCG         1830
Leu Glu Pro Met Leu Tyr Phe Glu Leu Gln Ile Pro Gln Ala
            540             545                 550
```

| | | | | | | | | | | | | |
|---|---|---|---|---|---|---|---|---|---|---|---|---|
| GCA | AGT | TCC | AAA | GCT | ATT | ACA | GAT | TTG | CAA | AAA | ATG ATG TCT | 1872 |
| Ala | Ser | Ser | Lys | Ala | Ile | Thr | Asp | Leu | Gln | Lys | Met Met Ser | |
| | | | | 555 | | | | | 560 | | | |
| GAG | ATT | GAA | GAC | ATC | AGT | TGC | AAT | AAT | GAG | TGG | TGT CAT ATT | 1914 |
| Glu | Ile | Glu | Asp | Ile | Ser | Cys | Asn | Asn | Glu | Trp | Cys His Ile | |
| 565 | | | | | 570 | | | | | 575 | | |
| AAA | GGG | AAA | GTT | CCA | TTA | AAT | ACA | AGT | AAA | GAC | TAT GCA TCA | 1956 |
| Lys | Gly | Lys | Val | Pro | Leu | Asn | Thr | Ser | Lys | Asp | Tyr Ala Ser | |
| | 580 | | | | | 585 | | | | | 590 | |
| GAA | GTA | AGT | TCA | TAC | ACT | AAG | GGC | TTA | GGC | ATT | TTT ATG GTT | 1998 |
| Glu | Val | Ser | Ser | Tyr | Thr | Lys | Gly | Leu | Gly | Ile | Phe Met Val | |
| | | 595 | | | | | 600 | | | | 605 | |
| AAG | CCA | TGC | GGG | TAT | CAA | ATA | ACA | AAA | GGC | GGT | TAT TCT GAT | 2040 |
| Lys | Pro | Cys | Gly | Tyr | Gln | Ile | Thr | Lys | Gly | Gly | Tyr Ser Asp | |
| | | | 610 | | | | | 615 | | | | 620 |
| AAT | ATC | CGC | ATG | AAC | GAA | AAA | GAT | AAA | CTT | TTA | TTC ATG TTC | 2082 |
| Asn | Ile | Arg | Met | Asn | Glu | Lys | Asp | Lys | Leu | Leu | Phe Met Phe | |
| | | | | 625 | | | | | 630 | | | |
| CAA | AAA | TCA | ATG | TCA | TCA | AAA | TAA | | | | | 2106 |
| Gln | Lys | Ser | Met | Ser | Ser | Lys | | | | | | |
| 635 | | | | | 640 | | | | | | | |

(Seq. ID NO:4)

that confer tetracycline resistance.

6. An isolated promoter functional in *Prevotolla ruminicola* which is the promoter of a TetQ gene having the nucleotide sequence of SEQ ID NO:1.

7. An isolated DNA molecule containing no more than 2700 deoxyribonucleotides per strand and having a DNA sequence encoding the following amino acid sequence:

Met Asn Ile Ile Asn Leu Gly Ile Leu Ala His Ile Ile Asp Ala Gly
                 5                  10                 15
Lys Thr Ser Val Thr Glu Asn Leu Leu Phe Ala Ser Gly Ala Thr
        20                  25                  30
Glu Lys Cys Gly Cys Val Asp Asn Gly Asp Thr Ile Thr Asp Ser
        35                  40                  45
Met Asp Ile Glu Lys Arg Arg Gly Ile Thr Val Arg Ala Ser Thr
        50                  55                  60
Thr Ser Ile Ile Trp Asn Gly Val Lys Cys Asn Ile Ile Asp Thr
        65                  70                  75
Pro Gly His Met Asp Phe Ile Ala Glu Val Glu Arg Thr Phe Lys
        80                  85                  90
Met Leu Asp Gly Ala Val Leu Ile Leu Ser Ala Lys Glu Gly Ile
        95                  100                 105
Gln Ala Gln Thr Lys Leu Leu Phe Asn Thr Leu Gln Lys Leu Gln
        110                 115                 120
Ile Pro Thr Ile Ile Phe Ile Asn Lys Ile Asp Arg Ala Gly Val
        125                 130                 135
Asn Leu Glu Arg Leu Tyr Leu Asp Ile Lys Ala Asn Leu Ser Gln
        140                 145                 150
Asp Val Leu Phe Met Gln Asn Val Val Asp Gly Ser Val Tyr Pro
        155                 160                 165
Val Cys Ser Gln Thr Tyr Ile Lys Glu Tyr Lys Glu Phe Val
        170                 175                 180
Cys Asn His Asp Asp Asn Ile Leu Glu Arg Tyr Leu Ala Asp Ser
        185                 190                 195
Glu Ile Ser Pro Ala Asp Tyr Trp Asn Thr Ile Ile Ala Leu Val
        200                 205                 210
Ala Lys Ala Lys Val Tyr Pro Val Leu His Gly Ser Ala Met Phe
        215                 220                 225
Asn Ile Gly Ile Asn Glu Leu Leu Asp Ala Ile Thr Ser Phe Ile
        230                 235                 240
Leu Pro Pro Ala Ser Val Ser Asn Arg Leu Ser Ser Tyr Leu Tyr
        245                 250                 255
Lys Ile Glu His Asp Pro Lys Gly His Lys Arg Ser Phe Leu Lys
        260                 265                 270
Ile Ile Asp Gly Ser Leu Arg Leu Arg Asp Val Val Arg Ile Asn
        275                 280                 285
Asp Ser Glu Lys Phe Ile Lys Ile Lys Asn Leu Lys Thr Ile Asn
        290                 295                 300
Gln Gly Arg Glu Ile Asn Val Asp Glu Val Gly Ala Asn Asp Ile
        305                 310                 315
Ala Ile Val Glu Asp Met Asp Asp Phe Arg Ile Gly Asn Tyr Leu
        320                 325                 330
Gly Ala Glu Pro Cys Leu Ile Gln Gly Leu Ser His Gln His Pro
        335                 340                 345
Ala Leu Lys Ser Ser Val Arg Pro Asp Arg Pro Glu Glu Arg Ser
        350                 355                 360
Lys Val Ile Ser Ala Leu Asn Thr Leu Trp Ile Glu Asp Pro Ser
        365                 370                 375
Leu Ser Phe Ser Ile Asn Ser Tyr Ser Asp Glu Leu Glu Ile Ser
        380                 385                 390
Leu Tyr Gly Leu Thr Gln Lys Glu Ile Gln Thr Leu Leu Glu
        395                 400                 405
Glu Arg Phe Ser Val Lys Val His Phe Asp Glu Ile Lys Thr Ile
        410                 415                 420
Tyr Lys Glu Arg Pro Val Lys Lys Val Asn Lys Ile Ile Gln Ile
        425                 430                 435
Glu Val Pro Pro Asn Pro Tyr Trp Ala Thr Ile Gly Leu Thr Leu
        440                 445                 450
Glu Pro Leu Pro Leu Gly Thr Gly Leu Gln Ile Glu Ser Asp Ile
        455                 460                 465
Ser Tyr Gly Tyr Leu Asn His Ser Phe Gln Asn Ala Val Phe Glu
        470                 475                 480
Gly Ile Arg Met Ser Cys Gln Ser Gly Leu His Gly Trp Glu Val
        485                 490                 495
Thr Asp Leu Lys Val Thr Phe Thr Gln Ala Glu Tyr Tyr Ser Pro
        500                 505                 510
Val Ser Tyr Pro Ala Asp Phe Arg Gln Leu Thr Pro Tyr Val Phe
        515                 520                 525
Arg Leu Ala Leu Gln Gln Ser Gly Val Asp Ile Leu Glu Pro Met
        530                 535                 540
Leu Tyr Phe Glu Leu Gln Ile Pro Gln Ala Ala Ser Ser Lys Ala
        545                 550                 555
Cys Asn Asn Glu Trp Cys His Ile Lys Gly Lys Val Pro Leu Asn
        575                 580                 585
Thr Ser Lys Asp Tyr Ala Ser Glu Val Ser Ser Tyr Thr Lys Gly
        590                 595                 600
Leu Gly Ile Phe Met Val Lys Pro Cys Gly Tyr Gln Ile Thr Lys
        605                 610                 615
Gly Gly Tyr Ser Asp Asn Ile Arg Met Asn Glu Lys Asp Lys Leu
        620                 625                 630
Leu Phe Met Phe Gln Lys Ser Met Ser Ser Lys (Seq. ID NO: 3).
        635                 640

8. The DNA sequence of claim 7 which is:

```
ATG AAT ATT ATA AAT TTA GGA ATT CTT GCT CAC ATT GAT GCA    42
Met Asn Ile Ile Asn Leu Gly Ile Leu Ala His Ile Asp Ala
                  5                      10
GGA AAA ACT TCC GTA ACC GAG AAT CTG CTG TTT GCC AGT GGA    84
Gly Lys Thr Ser Val Thr Glu Asn Leu Leu Phe Ala Ser Gly
 15              20                  25
GCA ACG GAA AAG TGC GGC TGT GTG GAT AAT GGT GAC ACC ATA   126
Ala Thr Glu Lys Cys Gly Cys Val Asp Asn Gly Asp Thr Ile
         30              35              40
ACG GAC TCT ATG GAT ATA GAG AAA CGT AGA GGA ATT ACT GTT   168
Thr Asp Ser Met Asp Ile Glu Lys Arg Arg Gly Ile Thr Val
             45              50                      55
CGG GCT TCT ACG ACA TCT ATT ATC TGG AAT GGT GTG AAA TGC   210
Arg Ala Ser Thr Thr Ser Ile Ile Trp Asn Gly Val Lys Cys
                 60              65                   70
AAT ATC ATT GAC ACT CCG GGA CAC ATG GAT TTT ATT GCG GAA   252
Asn Ile Ile Asp Thr Pro Gly His Met Asp Phe Ile Ala Glu
                 75              80
GTG GAG CGG ACA TTC AAA ATG CTT GAT GGA GCA GTC CTC ATC   294
Val Glu Arg Thr Phe Lys Met Leu Asp Gly Ala Val Leu Ile
 85              90              95
TTA TCC GCA AAG GAA GGC ATA CAA GCG CAG ACA AAG TTG CTG   336
Leu Ser Ala Lys Glu Gly Ile Gln Ala Gln Thr Lys Leu Leu
    100                 105             110
TTC AAT ACT TTA CAG AAG CTG CAA ATC CCG ACA ATT ATA TTT   378
Phe Asn Thr Leu Gln Lys Leu Gln Ile Pro Thr Ile Ile Phe
        115                 120                 125
ATC AAT AAG ATT GAC CGA GCC GGT GTG AAT TTG GAG CGT TTG   420
Ile Asn Lys Ile Asp Arg Ala Gly Val Asn Leu Glu Arg Leu
            130                 135                 140
TAT CTG GAT ATA AAA GCA AAT CTG TCT CAA GAT GTC CTG TTT   462
Tyr Leu Asp Ile Lys Ala Asn Leu Ser Gln Asp Val Leu Phe
                145                 150
ATG CAA AAT GTT GTC GAT GGA TCG GTT TAT CCG GTT TGC TCC   504
Met Gln Asn Val Val Asp Gly Ser Val Tyr Pro Val Cys Ser
155                 160                 165
CAA ACA TAT ATA AAG GAA GAA TAC AAA GAA TTT GTA TGC AAC   546
Gln Thr Tyr Ile Lys Glu Glu Tyr Lys Glu Phe Val Cys Asn
    170                 175                 180
CAT GAC GAC AAT ATA TTA GAA CGA TAT TTG GCG GAT AGC GAA   588
His Asp Asp Asn Ile Leu Glu Arg Tyr Leu Ala Asp Ser Glu
        185                 190                 195
ATT TCA CCG GCT GAT TAT TGG AAT ACG ATA ATC GCT CTT GTG   630
Ile Ser Pro Ala Asp Tyr Trp Asn Thr Ile Ile Ala Leu Val
            200                 205                 210
GCA AAA GCC AAA GTC TAT CCG GTG CTA CAT GGA TCA GCA ATG   672
Ala Lys Ala Lys Val Tyr Pro Val Leu His Gly Ser Ala Met
                215                 220
TTC AAT ATC GGT ATC AAT GAG TTG TTG GAC GCC ATC ACT TCT   714
Phe Asn Ile Gly Ile Asn Glu Leu Leu Asp Ala Ile Thr Ser
225                 230                 235
TTT ATA CTT CCT CCG GCA TCG GTC TCA AAC AGA CTT TCA TCT   756
Phe Ile Leu Pro Pro Ala Ser Val Ser Asn Arg Leu Ser Ser
    240                 245                 250
TAT CTT TAT AAG ATA GAG CAT GAC CCC AAA GGA CAT AAA AGA   798
Tyr Leu Tyr Lys Ile Glu His Asp Pro Lys Gly His Lys Arg
        255                 260                 265
AGT TTT CTA AAA ATA ATT GAC GGA AGT CTG AGA CTT CGA GAC   840
Ser Phe Leu Lys Ile Ile Asp Gly Ser Leu Arg Leu Arg Asp
            270                 275                 280
GTT GTA AGA ATC AAC GAT TCG GAA AAA TTC ATC AAG ATT AAA   882
Val Val Arg Ile Asn Asp Ser Glu Lys Phe Ile Lys Ile Lys
                285                 290
AAT CTA AAA ACT ATC AAT CAG GGC AGA GAG ATA AAT GTT GAT   924
Asn Leu Lys Thr Ile Asn Gln Gly Arg Glu Ile Asn Val Asp
295                 300                 305
GAA GTG GGC GCC AAT GAT ATC GCG ATT GTA GAG GAT ATG GAT   966
Glu Val Gly Ala Asn Asp Ile Ala Ile Val Glu Asp Met Asp
    310                 315                 320
GAT TTT CGA ATC GGA AAT TAT TTA GGT GCT GAA CCT TGT TTG  1008
Asp Phe Arg Ile Gly Asn Tyr Leu Gly Ala Glu Pro Cys Leu
        325                 330                 335
ATT CAA GGA TTA TCG CAT CAG CAT CCC GCT CTC AAA TCC TCC  1050
Ile Gln Gly Leu Ser His Gln His Pro Ala Leu Lys Ser Ser
            340                 345                 350
GTC CGG CCA GAC AGG CCC GAA GAG AGA AGC AAG GTG ATA TCC  1092
Val Arg Pro Asp Arg Pro Glu Glu Arg Ser Lys Val Ile Ser
                355                 360
GCT CTG AAT ACA TTG TGG ATT GAA GAC CCG TCT TTG TCC TTT  1134
Ala Leu Asn Thr Leu Trp Ile Glu Asp Pro Ser Leu Ser Phe
365                 370                 375
TCC ATA AAC TCA TAT AGT GAT GAA TTG GAA ATC TCG TTA TAT  1176
Ser Ile Asn Ser Tyr Ser Asp Glu Leu Glu Ile Ser Leu Tyr
    380                 385                 390
```

```
GGT TTA ACC CAA AAG GAA ATC ATA CAG ACA TTG CTG GAA GAA  1218
Gly Leu Thr Gln Lys Glu Ile Ile Gln Thr Leu Leu Glu Glu
        395                 400                 405
CGA TTT TCC GTA AAG GTC CAT TTT GAT GAG ATC AAG ACT ATA  1260
Arg Phe Ser Val Lys Val His Phe Asp Glu Ile Lys Thr Ile
            410                 415                 420
TAC AAA GAA GGA CCT GTA AAA AAG GTC AAT AAG ATT TAA CAG  1302
Tyr Lys Glu Arg Pro Val Lys Lys Val Asn Lys Ile Ile Gln
                425                 430
ATC GAA GTG CCG CCC AAC CCT TAT TGG GCC ACA ATA GGG CTG  1344
Ile Glu Val Pro Pro Asn Pro Tyr Trp Ala Thr Ile Gly Leu
435                 440                 445
ACT CTT GAT CCC TTA CCG TTA GGG ACA GGG TTG CAA ATC GAA  1386
Thr Leu Asp Pro Leu Pro Leu Gly Thr Gly Leu Gln Ile Glu
        450                 455                 460
AGT GAC ATC TCC TAT GGT TAT CTG AAC CAT TCT TTT CAA AAT  1428
Ser Asp Ile Ser Tyr Gly Tyr Leu Asn His Ser Phe Gln Asn
            465                 470                 475
GCC GTT TTT GAA GGG ATT CGT ATG TCT TGC CAA TCC GGG TTA  1470
Ala Val Phe Glu Gly Ile Arg Met Ser Cys Gln Ser Gly Leu
                480                 485                 490
CAT GGA TGG GAA GTG ACT GAT CTG AAA GTA ACT TTT ACT CAA  1512
His Gly Trp Glu Val Thr Asp Leu Lys Val Thr Phe Thr Gln
                    495                 500
GCC GAG TAT TAT AGC CCG GTA AGT ACA CCT GCT GAT TTC AGA  1554
Ala Glu Tyr Tyr Ser Pro Val Ser Tyr Pro Ala Asp Phe Arg
505                 510                 515
CAG CTG ACC CCT TAT GTC TTC AGG CTG GCC TTG CAA CAG TCA  1596
Gln Leu Thr Pro Tyr Val Phe Arg Leu Ala Leu Gln Gln Ser
    520                 525                 530
GGT GTG GAC ATT CTC GAA CCG ATG CTC TAT TTT GAG TTG CAG  1638
Gly Val Asp Ile Leu Glu Pro Met Leu Tyr Phe Glu Leu Gln
        535                 540                 545
ATA CCC CAA GCG GCA AGT TCC AAA GCT ATT ACA GAT TTG CAA  1680
Ile Pro Gln Ala Ala Ser Ser Lys Ala Ile Thr Asp Leu Gln
            550                 555                 560
AAA ATG ATG TCT GAG ATT GAA GAC ATC AGT TGC AAT AAT GAG  1722
Lys Met Met Ser Glu Ile Glu Asp Ile Ser Cys Asn Asn Glu
                565                 570
TGG TGT CAT ATT AAA GGG AAA GTT CCA TTA AAT ACA AGT AAA  1764
Trp Cys His Ile Lys Gly Lys Val Pro Leu Asn Thr Ser Lys
575                 580                 585
GAC TAT GCA TCA GAA GTA AGT TCA TAC ACT AAG GGC TTA GGC  1806
Asp Tyr Ala Ser Glu Val Ser Ser Tyr Thr Lys Gly Leu Gly
    590                 595                 600
ATT TTT ATG GTT AAG CCA TGC GGG TAT CAA ATA ACA AAA GGC  1848
Ile Phe Met Val Lys Pro Cys Gly Tyr Gln Ile Thr Lys Gly
        605                 610                 615
GGT TAT TCT GAT AAT ATC CGC ATG AAC GAA AAA GAT AAA CTT  1890
Gly Tyr Ser Asp Asn Ile Arg Met Asn Glu Lys Asp Lys Leu
            620                 625                 630
TTA TTC ATG TTC CAA AAA TCA ATG TCA TCA AAA TAA           1926
Leu Phe Met Phe Gln Lys Ser Met Ser Ser Lys
                635                 640
(Seq. ID No: 5).
```

9. A vector for expressing foreign DNA in *Prevotella ruminicola*, the foreign DNA being operatively linked to an isolated promoter of a TetQ gene having the nucleotide sequence of SEQ ID NO:1.

10. A vector for expressing foreign DNA in *Prevotella ruminicola* which comprises a selection marker which is an isolated TetQ gene and a Prevotella origin of replication.

* * * * *